(12) United States Patent
Kan et al.

(10) Patent No.: US 10,093,906 B2
(45) Date of Patent: Oct. 9, 2018

(54) CYTOCHROME C PROTEIN VARIANTS FOR CATALYZING CARBON-SILICON BOND FORMATION

(71) Applicant: California Institute of Technology, Pasadena, CA (US)

(72) Inventors: Sek Bik Jennifer Kan, Pasadena, CA (US); Russell D. Lewis, Pasadena, CA (US); Kai Chen, Pasadena, CA (US); Frances H. Arnold, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/422,360

(22) Filed: Feb. 1, 2017

(65) Prior Publication Data

US 2017/0218346 A1   Aug. 3, 2017

Related U.S. Application Data

(60) Provisional application No. 62/290,211, filed on Feb. 2, 2016, provisional application No. 62/365,797, filed on Jul. 22, 2016, provisional application No. 62/409,137, filed on Oct. 17, 2016.

(51) Int. Cl.
  *C12N 9/02*   (2006.01)
  *C07F 7/08*   (2006.01)

(52) U.S. Cl.
  CPC .......... *C12N 9/0042* (2013.01); *C07F 7/0818* (2013.01); *C07F 7/0829* (2013.01); *C07F 7/0896* (2013.01); *C12N 9/0071* (2013.01); *C12Y 106/02004* (2013.01); *C12Y 114/14001* (2013.01)

(58) Field of Classification Search
  None
  See application file for complete search history.

(56) References Cited

U.S. PATENT DOCUMENTS

2015/0267232 A1   9/2015   Coelho et al.

FOREIGN PATENT DOCUMENTS

WO   2017136466   8/2017

OTHER PUBLICATIONS

Buck, et al., "Asymmetric rhodium carbene insertion into the Si—H bond: Identification of new dirhodium(II) carboxylate catalysts using parallel synthesis techniques." Tetrahedron Asymmetry, 2003, vol. 14, pp. 791-816.
Buck, et al., "Asymmetric Rhodium Carbenoid Insertion into the Si—H Bond", Tetrahedron Lett., 1996, vol. 37, No. 42, pp. 7631-7634.
Buck, et al., Parallel synthesis techniques in the identification of new chiral dirhodium(II) carboxylates for asymmetric carbenoid insertion reactions. Tetrahedron Lett., 1998, vol. 39, pp. 7181-7184.
Chen, et al., "Rhodium(I)-Catalyzed Highly Enantioselective Insertion of Carbenoid into Si—H: Efficient Access to Functional Chiral Silanes", J. Am. Chem. Soc., 2016, vol. 138, pp. 1498-1501.
Dakin, et al, "Speciation and Mechanistic Studies of Chiral Copper(I) Schiff Base Precursors Mediating Asymmetric Carbenoid Insertion Reactions of Diazoacetates into the Si—H Bond of Silanes".Organometallics, 2000, vol. 19, pp. 2896-2908.
Dakin, et al., "Carbenoid Insertions into the Silicon-Hydrogen Bond Catalyzed by Chiral Copper(I) Schiff Base Complexes", Tetrahedron Lett., 1998, vol. 39, pp. 8947-8950.
Davies, et al., "Rhodium (II) (S)-N-(arylsulfonyl)prolinate catalyzed asymmetric insertions of vinyl- and phenylcarbenoids into the Si—H bond", Tetrahedron Lett., 1997, vol. 38, No. 10, pp. 1741-1744.
Doyle, et al., "Reactivity Enhancement for Chiral Dirhodium(II) Tetrakis(Carboxamidates)". Adv. Synth. Catal., 2001, vol. 343, No. 1, pp. 112-117.
Ge, et al., "A method for the catalytic enantioselective synthesis of 6-silylated 2-cyclohexenones". Tetrahedron Lett. 2006, vol. 47, pp. 2319-2321.
Hrdina, et al., "Synthesis, Structural Analysis, and Catalytic Properties of Tetrakis(binaphthyl or octahydrobinaphthyl phosphate) Dirhodium(II,II) Complexes". Organometallics, 2013, vol. 32, pp. 473-479.
Hyde, et al., "Coppercatalyzed Insertion into Heteroatom-Hydrogen Bonds with Trifluorodiazoalkanes" Angew. Chem. Int. Ed. 2016, vol. 55, pp. 3785-3789.
Jonathan, et al., "The effect of replacing the axial methionine ligand with a lysine residue in cytochrome c-550 from Paracoccus versutus assessed by X-ray crystallography and unfolding", Leiden Institute of Chemistry, Leiden University, Gorlaeus Laboratories, Leiden, the Netherlands, Mar. 15, 2005, pp. 2441-2455.
Kan, et al., "Directed evolution of cytochrome C for carbon-silicon bond formation: Bringing silicon to life", Science, Nov. 2016, vol. 354, No. 6315, pp. 1048-1051.
Kan, et al., "Supplemental Materials for Directed evolution of cytochrome C for carbon-silicon bond formation: Bringing silicon to life", Science, Nov. 2016, vol. 354, No. 1048, pp. 1-111.
Kitagaki, et al., "Enantioselective Si—H insertion of methyl phenyldiazoacetate catalyzed by dirhodium(II) carboxylates incorporating N-phthaloyl-(S)-amino acids as chiral bridging ligands" Tetrahedron Asymmetry, 2000, vol. 11, pp. 3855-3859.

(Continued)

*Primary Examiner* — Hope Robinson
(74) *Attorney, Agent, or Firm* — Kilpatrick Townsend & Stockton LLP

(57) ABSTRACT

The present invention provides compositions and methods for catalyzing the formation of carbon-silicon bonds using heme proteins. In certain aspects, the present invention provides heme proteins, including variants and fragments thereof, that are capable of carrying out in vitro and in vivo carbene insertion reactions for the formation of carbon-silicon bonds. In other aspects, the present invention provides methods for producing an organosilicon product, the method comprising providing a silicon-containing reagent, a carbene precursor, and a heme protein; and combining the components under conditions sufficient to produce an organosilicon product. Host cells expressing the heme proteins are also provided by the present invention.

19 Claims, 16 Drawing Sheets
Specification includes a Sequence Listing.

(56) References Cited

OTHER PUBLICATIONS

PCT/US2017/016083, "International Search Report and Written Opinion", dated Jul. 10, 2017, 11 pages.
PCT/US2017/016083, "Invitation to Pay Add'l Fees and Partial Search Rpt", May 9, 2017, 4 pages.
Sambasivan, et al,, "Metallopeptides for Asymmetric Dirhodium Catalysis" J.Am. Chem. Soc., 2010, vol. 132, pp. 9289-9291.
UniprotKB accession No. B3FQS5, [retrieved on May 4, 2017 from http://www.uniprot.org/uniprot/B3FQS5.txt?version=32], Jul. 22, 2008, 1 page.
Wang, et al., "Highly enantioselective intermolecular carbene insertion to C—H and Si—H bonds catalyzed by a chiral iridium(III) complex of a D4-symmetric Halterman porphyrin ligand". Chem. Commun., 2012, vol. 48, pp. 4299-4301.
Wu, et al., "Total Synthesis of (−)-Virginiamycin M2: Application of Crotylsilanes Accessed by Enantioselective Rh(II) or Cu(I) Promoted Carbenoid Si—H Insertion". J. Org. Chem., 2011, vol. 76, pp. 9900-9918.
Yasutomi, et al., "Iridium(III)-Catalyzed Enantioselective Si—H Bond Insertion and Formation of an Enantioenriched Silicon Center", J. Am. Chem. Soc., 2010, vol. 132, pp. 4510-4511.
Zhang, et al., "Copper-Catalyzed Highly Enantioselective Carbenoid Insertion into Si—H Bonds". Angew. Chem. Int. Ed., 2008, vol. 47, pp. 8496-8498.

| R | $k_R / k_H$ | $\log(k_R / k_H)$ | σ |
|---|---|---|---|
| H | 1 | 0 | 0 |
| MeO | 1.3 | 0.13 | −0.27 |
| NH$_2$ | 3.2 | 0.50 | −0.66 |
| Cl | 0.78 | −0.11 | 0.23 |
| CO$_2$Me | 0.47 | −0.32 | 0.45 |

CYTOCHROME C PROTEIN VARIANTS FOR CATALYZING CARBON-SILICON BOND FORMATION

CROSS-REFERENCES TO RELATED APPLICATIONS

The present application claims priority to U.S. Provisional Application No. 62/290,211 filed on Feb. 2, 2016; U.S. Provisional Application No. 62/365,797 filed on Jul. 22, 2016; and U.S. Provisional Application No. 62/409,137 filed on Oct. 17, 2016, the disclosures of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with government support under Grant No. CBET1403077 awarded by the National Science Foundation and under Grant No. GM007616 awarded by the National Institutes of Health. The government has certain rights in the invention.

REFERENCE TO A SEQUENCE LISTING

The Sequence Listing written in file SequenceListing_086544-020330US-1025419.txt created on Mar. 10, 2017, 3,274 bytes, machine format IBM-PC, MS-Windows operating system, is hereby incorporated by reference in its entirety for all purposes.

BACKGROUND OF THE INVENTION

Organic compounds containing carbon-silicon bonds are of great interest in the fields of synthetic chemistry, drug discovery, nuclear medicine, biotechnology, and materials science. As a result, chemical methods available for introducing silicon to the carbon framework of organic molecules have improved in recent years. Among these methods, however, only a small fraction are suitable for the preparation of chiral organosilicon compounds. One approach for asymmetric carbon-silicon bond formation is via carbenoid insertion into silicon-hydrogen bonds, which can be achieved using chiral rhodium, iridium, or copper catalysts. While these transition metal catalysts have demonstrated utility in preparing highly selective products, their turnovers are poor (i.e., none exceeds a total turnover number of 100), and the elaborate catalyst structures required to control selectivity are lengthy and expensive to synthesize. Moreover, most of these processes rely on the use of chlorinated solvents and cryogenic conditions to achieve the desired reaction outcomes. Accordingly, there is a need in the art for new methods of synthesis of organosilicon compounds, in particular methods that can carry out the production of these compounds with high efficiency, low cost, and reduced dependence on harsh chemical reagents and reaction conditions. The present invention satisfies this need, and provides related advantages as well.

BRIEF SUMMARY OF THE INVENTION

In a first aspect, the invention provides a cytochrome c protein variant, or a fragment thereof, that is capable of enantioselectively catalyzing the formation of a carbon-silicon bond. In some embodiments, the cytochrome c protein variant comprises a mutation at an axial heme coordination residue. In other embodiments, the cytochrome c protein variant comprises one or more mutations selected from the group consisting of V75, M100, and M103 relative to the amino acid sequence set forth in SEQ ID NO:1. In some instances, the one or more mutations comprise a V75 mutation and an M100 mutation relative to the amino acid sequence set forth in SEQ ID NO:1. In other instances, the one or more mutations comprise a M100 mutation and an M103 mutation relative to the amino acid sequence set forth in SEQ ID NO:1. In yet other instances, the one or more mutations comprise a V75 mutation, a M100 mutation, and an M103 mutation relative to the amino acid sequence set forth in SEQ ID NO:1. In particular instances, the V75 mutation is a V75T mutation. In other instances, the M100 mutation is an M100D or M100E mutation. In still other instances, the M103 mutation is an M103E mutation.

In other embodiments, the heme cofactor of the cytochrome c protein variant is a non-native cofactor.

In some embodiments, the cytochrome c protein variant has a higher total turnover number (TTN) compared to the wild-type protein. In some instances, the TTN is greater than about 70. In particular instances, the TTN is greater than about 1,800.

In other embodiments, the cytochrome c protein variant has a higher turnover frequency (TOF) compared to the wild-type protein. In some instances, the TOF is at least about 2-fold greater than the wild-type protein. In particular instances, the TOF is at least about 7-fold greater than the wild-type protein. In some instances, the TOF is at least about 10 min$^{-1}$. In particular instances, the TOF is at least about 45 min$^{-1}$.

In some embodiments, the cytochrome c protein variant produces an organosilicon product with a % ee of at least about 75%. In some instances, the cytochrome c protein variant produces an organosilicon product with a % ee of at least about 95%. In particular instances, the cytochrome c protein variant produces an organosilicon product with a % ee of at least about 99%.

In a second aspect, the invention provides a cell comprising a cytochrome c protein variant, or a fragment thereof, of the present invention. In some embodiments, the cell is a bacterial, archaeal, yeast, or fungal cell. In some instances, the bacterial cell is an *Escherichia coli* cell.

In a third aspect, the invention provides a method for producing an organosilicon product. In some embodiments, the method comprises combining a silicon-containing reagent, a carbene precursor, and a heme protein, a fragment thereof, or a variant thereof, under conditions sufficient to produce an organosilicon product. In particular embodiments, the heme protein or fragment thereof is selected from the group consisting of a cytochrome protein, a globin protein, a myoglobin protein, a hemoglobin protein, a peroxidase, a catalase, and a combination thereof. In some instances, the globin protein is from *Methylacidiphilum infernorum*. In other instances, the cytochrome protein is a cytochrome c protein, a cytochrome P450 protein, or a combination thereof. In some instances, the cytochrome P450 protein is a cytochrome P450 BM3 (CYP102A1) protein. In particular instances, the cytochrome c protein is selected from the group consisting of *Rhodothermus marinus* (Rma) cytochrome c, *Rhodopila globiformis* cytochrome c, *Hydrogenobacter thermophilus* cytochrome c, *Saccharomyces cerevisiae* cytochrome c, horse heart cytochrome c, bovine heart cytochrome c, and a combination thereof.

In some embodiments, the heme protein, fragment thereof, or variant thereof can enantioselectively catalyze the formation of a carbon-silicon bond. In other embodiments, the heme protein variant comprises a mutation at an axial heme coordination residue. In some embodiments, the heme variant is a *Rhodothermus marinus* (Rma) cytochrome c protein variant comprising one or more mutations selected from the group consisting of V75, M100, and M103 relative to the amino acid sequence set forth in SEQ ID NO:1. In some instances, the one or more mutations comprise a V75 mutation and an M100 mutation relative to the amino acid sequence set forth in SEQ ID NO:1. In other instances, the one or more mutations comprise an M100 mutation and an M103 mutation relative to the amino acid sequence set forth in SEQ ID NO:1. In particular instances, the one or more mutations comprise a V75 mutation, an M100 mutation, and an M103 mutation relative to the amino acid sequence set forth in SEQ ID NO:1. In some instances, the V75 mutation is a V75T mutation. In other instances, the M100 mutation is an M100D or M100E mutation. In still other instances, the M103 mutation is an M103E mutation.

In other embodiments, the heme protein cofactor is a non-native cofactor.

In some other embodiments, the heme protein is a variant that has a higher TTN compared to the wild-type protein. In some instances, the TTN is greater than about 70. In particular instances, the TTN is greater than about 1,800.

In other embodiments, the heme protein has a TOF that is at least about 10 min$^{-1}$. In some instances, the TOF is at least about 45 min$^{-1}$. In some embodiments, the heme protein is a variant that has a TOF that is higher compared to the TOF of the wild-type protein. In some instances, the TOF is at least about 2-fold greater than the wild-type protein. In particular instances, the TOF is at least about 7-fold greater than the wild-type protein.

In still other embodiments, the heme protein, fragment thereof, or variant thereof produces an organosilicon product with a % ee of at least about 75%. In some instances, the % ee is at least about 95%. In particular instances, the % ee is at least about 99%.

In some embodiments, the silicon-containing reagent is a compound according to Formula I:

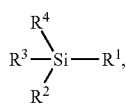

wherein $R^1$, $R^2$, $R^3$ and $R^4$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, hydroxy, alkoxy, $SR^7$, $N(R^8)_2$, $B(R^9)_2$, $Si(R^9)_3$, $P(R^9)_3$, $C(O)OR^7$, $C(O)SR^7$, $C(O)N(R^7)_2$, $C(O)R^7$, $C(O)ON(R^7)_2$ and $C(O)NR^7OR^8$; and wherein $R^7$, $R^8$, and $R^9$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, and optionally substituted 6- to 10-membered heterocyclyl.

In some instances, $R^2$ is selected from the group consisting of optionally substituted $C_{1-18}$ alkyl, optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl. In other instances, $R^3$ and $R^4$ are $C_{1-6}$ alkyl.

In other embodiments, the carbene precursor is a diazo substrate according to Formula II:

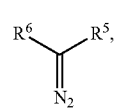

wherein $R^5$ and $R^6$ are independently selected from the group consisting of H, optionally substituted $C_{1-18}$ alkyl, optionally substituted C haloalkyl, optionally substituted $C_{2-18}$ alkenyl, optionally substituted $C_{2-18}$ alkynyl, optionally substituted $C_{6-10}$ aryl, optionally substituted 6- to 10-membered heteroaryl, optionally substituted 6- to 10-membered heterocyclyl, cyano, halo, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$; and wherein each $R^7$, $R^8$, and $R^9$ is independently selected from the group consisting of H and optionally substituted $C_{1-6}$ alkyl.

In some instances, $R^5$ is $C(O)OR^7$. In other instances, $R^6$ is selected from the group consisting of optionally substituted $C_{1-18}$ alkyl, optionally substituted $C_{1-18}$ haloalkyl, and optionally substituted $C_{2-18}$ alkenyl.

In some embodiments, the organosilicon product is a compound according to Formula III:

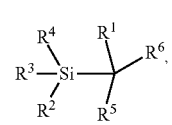

wherein $R^1$, $R^2$, $R^3$ and $R^4$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, hydroxy, alkoxy, $SR^7$, $N(R^8)_2$, $B(R^9)_2$, $Si(R^9)_3$, $P(R^9)_3$, $C(O)OR^7$, $C(O)SR^7$, $C(O)N(R^7)_2$, $C(O)R^7$, $C(O)ON(R^7)_2$ and $C(O)NR^7R^8$. $R^5$ and $R^6$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$ and $P(O)(OR7)_2$. $R^7$, $R^8$, and $R^9$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, and optionally substituted 6- to 10-membered heterocyclyl.

In some instances, $R^2$ is selected from the group consisting of optionally substituted $C_{1-18}$ alkyl, optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl. In other instances, $R^3$ and $R^4$ are $C_{1-6}$ alkyl. In yet other instances, $R^5$ is $C(O)OR^7$. In other instances, $R^6$ is selected from the group consisting of optionally substituted $C_{1-18}$ alkyl, optionally substituted $C_{1-18}$haloalkyl, and optionally substituted $C_{2-18}$ alkenyl.

In other embodiments, a reducing agent is combined with the silicon-containing reagent and carbene precursor. In some embodiments, the organosilicon product is produced in vitro. In still other embodiments, the heme protein, fragment thereof, or variant thereof is expressed in a cell and the organosilicon product is produced in vivo. In some instances, the cell is a bacterial cell, archaeal cell, yeast cell, or fungal cell. In particular instances, the bacterial cell is an *Escherichia coli* cell. In some embodiments, the organosilicon product is produced under anaerobic conditions. In other embodiments, the organosilicon product is produced under aerobic conditions.

In a fourth aspect, the invention provides a reaction mixture for producing an organosilicon product. In some embodiments, the reaction mixture comprises a silicon-containing reagent, a carbene precursor, and a heme protein, a fragment thereof, or a variant thereof. In particular embodiments, the heme protein or fragment thereof is selected from the group consisting of a cytochrome protein, a globin protein, a myoglobin protein, a hemoglobin protein, a peroxidase, a catalase, and a combination thereof. In some instances, the globin protein is selected from the group consisting of *Methylacidiphilum infernorum* globin protein, sperm whale globin protein, *Rhodothermus marinus* (Rma) globin protein, *Bacillus subtilis* globin protein, *Pyrobaculum ferrireducens* globin protein, *Aeropyrum pernix* globin protein, *Campylobacter jejuni* globin protein, and a combination thereof. In other instances, the cytochrome protein is a cytochrome c protein, a cytochrome P450 protein, or a combination thereof. In some instances, the cytochrome P450 protein is a cytochrome P450 BM3 (CYP102A1) protein. In particular instances, the cytochrome c protein is selected from the group consisting of *Rhodothermus marinus* (Rma) cytochrome c, *Rhodopila globiformis* cytochrome c, *Hydrogenobacter thermophilus* cytochrome c, *Saccharomyces cerevisiae* cytochrome c, horse heart cytochrome c, bovine heart cytochrome c, and a combination thereof.

In some embodiments, the heme protein, fragment thereof, or variant thereof can enantioselectively catalyze the formation of a carbon-silicon bond. In other embodiments, the heme protein variant comprises a mutation at an axial heme coordination residue. In some embodiments, the heme variant is a *Rhodothermus marinus* (Rma) cytochrome c protein variant comprising one or more mutations selected from the group consisting of V75, M100, and M103 relative to the amino acid sequence set forth in SEQ ID NO:1. In some instances, the one or more mutations comprise a V75 mutation and an M100 mutation relative to the amino acid sequence set forth in SEQ ID NO:1. In other instances, the one or more mutations comprise an M100 mutation and an M103 mutation relative to the amino acid sequence set forth in SEQ ID NO:1. In particular instances, the one or more mutations comprise a V75 mutation, an M100 mutation, and an M103 mutation relative to the amino acid sequence set forth in SEQ ID NO:1. In some instances, the V75 mutation is a V75T mutation. In other instances, the M100 mutation is an M100D or M100E mutation. In still other instances, the M103 mutation is an M103E mutation.

In other embodiments, the heme protein cofactor is a non-native cofactor.

In some other embodiments, the heme protein is a variant that has a higher TTN compared to the wild-type protein. In some instances, the TTN is greater than about 70. In particular instances, the TTN is greater than about 1,800.

In other embodiments, the heme protein has a TOF that is at least about 10 min$^{-1}$. In some instances, the TOF is at least about 45 min$^{-1}$. In some embodiments, the heme protein is a variant that has a TOF that is higher compared to the TOF of the wild-type protein. In some instances, the TOF is at least about 2-fold greater than the wild-type protein. In particular instances, the TOF is at least about 7-fold greater than the wild-type protein.

In still other embodiments, the heme protein, fragment thereof, or variant thereof produces an organosilicon product with a % ee of at least about 75%. In some instances, the % ee is at least about 95%. In particular instances, the % ee is at least about 99%.

In some embodiments, the silicon-containing reagent is a compound according to Formula I:

wherein $R^1$ is H and $R^2$, $R^3$, and $R^4$ are independently selected from the group consisting of H, optionally substituted $C_{1-18}$ alkyl, optionally substituted $C_{2-18}$ alkenyl, optionally substituted $C_{2-18}$ alkynyl, optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl; provided that at least one of $R^2$, $R^3$, and $R^4$ is other than H.

In some instances, $R^2$ is selected from the group consisting of optionally substituted $C_{1-18}$ alkyl, optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl. In other instances, $R^3$ and $R^4$ are $C_{1-6}$ alkyl.

In other embodiments, the carbene precursor is a diazo substrate according to Formula II:

wherein $R^5$ and $R^6$ are independently selected from the group consisting of H, optionally substituted $C_{1-18}$ alkyl, optionally substituted C haloalkyl, optionally substituted $C_{2-18}$ alkenyl, optionally substituted $C_{2-18}$ alkynyl, optionally substituted $C_{6-10}$ aryl, optionally substituted 6- to 10-membered heteroaryl, optionally substituted 6- to 10-membered heterocyclyl, cyano, halo, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$; and wherein each $R^7$, $R^8$, and $R^9$ is independently selected from the group consisting of H and optionally substituted $C_{1-6}$ alkyl.

In some instances, $R^5$ is $C(O)OR^7$. In other instances, $R^6$ is selected from the group consisting of optionally substituted $C_{1-18}$ alkyl, optionally substituted $C_{1-18}$ haloalkyl, and optionally substituted $C_{2-18}$ alkenyl.

In some embodiments, the organosilicon product is a compound according to Formula III:

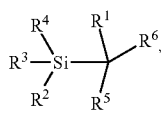

(III)

wherein $R^1$ is H; $R^2$, $R^3$, and $R^4$ are independently selected from the group consisting of H, optionally substituted $C_{1-18}$ alkyl, optionally substituted $C_{2-18}$ alkenyl, optionally substituted $C_{2-18}$ alkynyl, optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl; provided that at least one of $R^2$, $R^3$, and $R^4$ is other than H; and $R^5$ and $R^6$ are independently selected from the group consisting of H, optionally substituted $C_{1-18}$ alkyl, optionally substituted $C_{1-18}$ haloalkyl, optionally substituted $C_{2-18}$ alkenyl, optionally substituted $C_{2-18}$ alkynyl, optionally substituted $C_{6-10}$ aryl, optionally substituted 6- to 10-membered heteroaryl, optionally substituted 6- to 10-membered heterocyclyl, cyano, halo, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7R^8$, $C(O)C(O)OR^7$, and $P(O)(OR^7)_2$; wherein each $R^7$, $R^8$, and $R^9$ is independently selected from the group consisting of H and optionally substituted $C_{1-6}$ alkyl.

In some instances, $R^2$ is selected from the group consisting of optionally substituted $C_{1-18}$ alkyl, optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl. In other instances, $R^3$ and $R^4$ are $C_{1-6}$ alkyl. In yet other instances, $R^5$ is $C(O)OR^7$. In other instances, $R^6$ is selected from the group consisting of optionally substituted $C_{1-18}$ alkyl, optionally substituted $C_{1-18}$ haloalkyl, and optionally substituted $C_{2-18}$ alkenyl.

In other embodiments, the reaction mixture further comprises a reducing agent. In some embodiments, the organosilicon product is produced in vitro. In still other embodiments, the heme protein, fragment thereof, or variant thereof is expressed in a cell and the organosilicon product is produced in vivo. In some instances, the cell is a bacterial cell, archaeal cell, yeast cell, or fungal cell. In particular instances, the bacterial cell is an *Escherichia coli* cell. In some embodiments, the organosilicon product is produced under anaerobic conditions. In other embodiments, the organosilicon product is produced under aerobic conditions.

Other objects, features, and advantages of the present invention will be apparent to one of skill in the art from the following detailed description and figures.

BRIEF DESCRIPTION OF THE DRAWINGS

FIG. 5A shows carbon-silicon bond formation catalyzed by heme and purified heme proteins. Various P450s and myoglobin also catalyzed the formation of carbon-silicon bonds, but the reactions were not enantioselective. FIG. 5B shows a surface representation of the heme-binding pocket of wild-type Rma cyt c (PDB ID: 3CP5). FIG. 5C shows the "active site" structure of wild-type Rma cyt c showing a covalently bound heme cofactor ligated by axial ligands H49 and M100. Amino acid residues M100, V75 and M103 residing close to the heme iron were subjected to site-saturation mutagenesis. FIG. 5D shows the results of directed evolution of Rma cyt c for carbon-silicon bond formation (reaction shown in FIG. 5A). Experiments were performed using lysates of *E. coli* expressing Rma cyt c variant ($OD_{600}$=15; heat-treated at 75° C. for 10 minutes), 10 mM silane, 10 mM diazo ester, 10 mM $Na_2S_2O_4$, 5 vol % MeCN, M9-N buffer (pH 7.4) at room temperature under anaerobic conditions for 1.5 h. Reactions were performed in triplicate. FIG. 5E shows carbon-silicon bond forming rates over four generations of Rma cyt c.

FIG. 8A shows that chemoselectivity for carbene Si—H insertion over N—H insertion increased dramatically during the directed evolution of Rma cyt c. Reaction conditions as described in FIG. 7 were used. Reactions were performed in duplicate using heat-treated lysates of *E. coli* expressing Rma cyt c with protein concentration normalized across variants. Product distribution was quantified after 2 hours of reaction time (i.e., before complete conversion, no double insertion product was observed under these conditions). FIG. 8B shows the in vivo synthesis of organosilicon compound 22.

FIG. 9A shows the calibration curve for wild-type Rma cyt c. FIG. 9B shows the calibration curve for Rma cyt c V75T M100D M103E.

FIG. 13A shows a reaction in which a carbon-silicon bond is formed. FIG. 13B shows the active site structure of wild-type Rma cyt c showing residues V75, M100, and M103 (PDB ID: 3CP5). FIG. 13C shows the binding mode for the iron-carbenoid, where the carbenoid forms in a way that takes the place of the axial methionine. The silane approaches from the more solvent-exposed side in the wild-type protein, which explains the observed stereochemistry of the organosilicon product. The V75T, M100D, and M103E mutations may promote reactivity by improving solvent and substrate access to the iron center.

FIG. 14A shows a schematic of the reaction. FIG. 14B shows TTN as a function of time. Experiments were performed using 3 μM purified Rma cyt c V75T M100D M103E, 10 mM silane, 10 mM diazo ester, 10 mM Na$_2$S$_2$O$_4$, 5 vol % MeCN, M9-N buffer at room temperature under anaerobic conditions. Reactions were performed in duplicate. TTNs shown are the average of two experiments.

FIG. 16A shows the chemical reaction. FIG. 16B shows a Hammett plot that shows a small build-up of positive charge on the silane in the reaction transition state. This observation is similar to that reported for carbene insertion into Si—H bond catalyzed by copper (ρ=−0.54) (Dakin et al, *Organometallics* 19:2896-2908 (2000)) and rhodium (ρ=−0.31) (Landais et al. *Tetrahedron Lett.* 38:229-232 (1997)).

DETAILED DESCRIPTION OF THE INVENTION

I. Introduction

Figure 1:
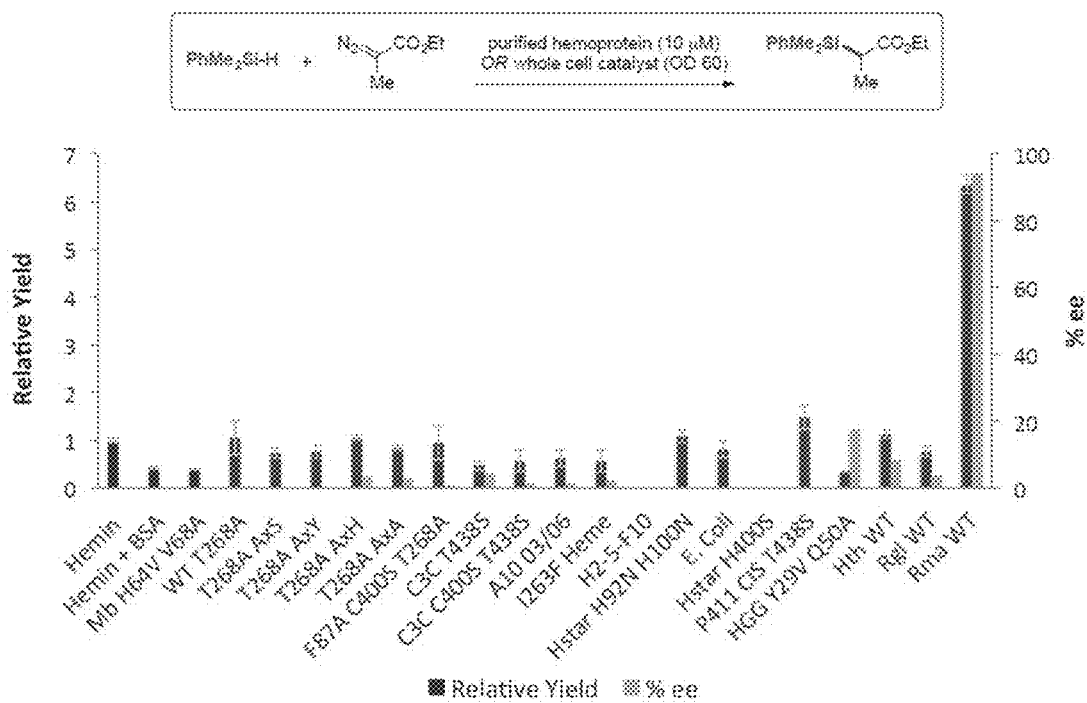
FIG. 1 shows the relative yield and % ee of organosilicon products afforded by various heme proteins. Myoglobin protein tested: Mb H64V V68A. Cytochrome P450 proteins tested: WT T268A, T268A AxS, T268A AxY, T268A AxH, T268A AxA, F87A C400S T268A, C3C T438S, C3C C400S T438S, A10 03/06, P-I263F Heme, H2-5-F10, Hstar H92N H100N, Hstar H400S, and P411 CIS T438S. Globin tested: HGG Y29V Q50A. Cytochrome c proteins tested: Hth WT, Rgl WT and Rma WT.

Enzymes are environmentally friendly and cost-effective alternatives to transition metal catalysts. These genetically encoded catalysts can achieve exquisite selectivity with efficiency that is difficult or impossible to achieve using small molecule catalysts. In nature, however, biologically synthesized carbon-silicon bonds, either in vitro or in vivo, are not known, despite silicon being the second most abundant element in the Earth's crust.

The present invention is based, in part, on the discovery that various heme proteins catalyze the in vitro and in vivo formation of carbon-silicon bonds. In addition, the present invention is based, in part, on the use of directed protein evolution to improve the ability of heme proteins to construct carbon-silicon chemical bonds. As such, the present invention provides, among other things, engineered heme proteins that catalyze carbon-silicon bond formation with a high total turnover number and high enantioselectivity.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the reagent" includes reference to one or more reagents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The terms "heme protein variant" and "heme enzyme variant" include any heme-containing enzyme comprising at least one amino acid mutation with respect to wild-type and also include any chimeric protein comprising recombined sequences or blocks of amino acids from two, three, or more different heme-containing enzymes.

The term "whole cell catalyst" includes cells expressing heme-containing enzymes, wherein the whole cell catalyst displays carbon-silicon bond formation activity.

The term "carbene precursor" includes molecules that can be decomposed in the presence of metal (or enzyme) catalysts to structures that contain at least one divalent carbon with only 6 valence shell electrons and that can be transferred to a silicon-hydrogen bond, a silicon-carbon bond, a silicon-sulfur bond, a silicon-nitrogen bond, a silicon-boron bond, a silicon-silicon bond, or a silicon-phosphorus bond to form various carbon ligated products. Examples of carbene precursors include, but are not limited to, diazo reagents, diazirene reagents, and epoxide reagents.

As used herein, the term "anaerobic", when used in reference to a reaction, culture or growth condition, is intended to mean that the concentration of oxygen is less than about 25 μM, preferably less than about 5 μM, and even more preferably less than 1 μM. The term is also intended to include sealed chambers of liquid or solid medium maintained with an atmosphere of less than about 1% oxygen. Preferably, anaerobic conditions are achieved by sparging a reaction mixture with an inert gas such as nitrogen or argon.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can refer to alkyl groups having up to 20 carbons atoms, such as, but not limited to heptyl, octyl, nonyl, decyl, etc. Alkyl groups can be optionally substituted with one or more moieties selected from halo, hydroxy, amino, alkylamino, alkoxy, haloalkyl, carboxy, amido, nitro, oxo, and cyano.

As used herein, the term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be optionally substituted with one or more moieties selected from halo, hydroxy, amino, alkylamino, alkoxy, haloalkyl, carboxy, amido, nitro, oxo, and cyano.

As used herein, the term "alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be optionally substituted with one or more moieties selected from halo, hydroxy, amino, alkylamino, alkoxy, haloalkyl, carboxy, amido, nitro, oxo, and cyano.

As used herein, the term "aryl" refers to an aromatic carbon ring system having any suitable number of ring atoms and any suitable number of rings. Aryl groups can include any suitable number of carbon ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be optionally substituted with one or more moieties selected from alkyl, alkenyl, alkynyl, haloalkyl, halo, hydroxy, amino, alkylamino, alkoxy, haloalkyl, carboxy, alkyl carboxylate, amido, nitro, oxo, and cyano.

As used herein, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. Cycloalkyl groups can be optionally substituted with one or more moieties selected from alkyl, alkenyl, alkynyl, haloalkyl, halo, hydroxy, amino, alkylamino, alkoxy, haloalkyl, carboxy, alkyl carboxylate, amido, nitro, oxo, and cyano.

As used herein, the term "heterocyclyl" refers to a saturated ring system having from 3 to 12 ring members and from 1 to 4 heteroatoms selected from N, O and S. Additional heteroatoms including, but not limited to, B, Al, Si and P can also be present in a heterocycloalkyl group. The heteroatoms can be oxidized to form moieties such as, but not limited to, —S(O)— and —S(O)$_2$—. Heterocyclyl groups can include any number of ring atoms, such as, 3 to 6, 4 to 6, 5 to 6, 4 to 6, or 4 to 7 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. Examples of heterocyclyl groups include, but are not limited to, aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. Heterocyclyl groups can be optionally substituted with one or more moieties selected from alkyl, alkenyl, alkynyl, haloalkyl, halo, hydroxy, amino, alkylamino, alkoxy, haloalkyl, carboxy, alkyl carboxylate, amido, nitro, oxo, and cyano.

As used herein, the term "heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms including, but not limited to, B, Al, Si and P can also be present in a heteroaryl group. The heteroatoms can be oxidized to form moieties such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. Examples of heteroaryl groups include, but are not limited to, pyrrole, pyridine, imidazole, pyrazole, triazole, tetrazole, pyrazine, pyrimidine, pyridazine, triazine (1,2,3-, 1,2,4- and 1,3,5- isomers), thiophene, furan, thiazole, isothiazole, oxazole, and isoxazole. Heteroaryl groups can be optionally substituted with one or more moieties selected from alkyl, alkenyl, alkynyl, haloakyl, halo, hydroxy, amino, alkylamino, alkoxy, haloalkyl, carboxy, alkyl carboxylate, amido, nitro, oxo, and cyano.

As used herein, the term "alkoxy" refers to an alkyl group having an oxygen atom that connects the alkyl group to the point of attachment: i.e., alkyl-O—. As for alkyl group, alkoxy groups can have any suitable number of carbon atoms, such as $C_{1-6}$ or $C_{1-4}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups can be optionally substituted with one or more moieties selected from halo, hydroxy, amino, alkylamino, alkoxy, haloalkyl, carboxy, amido, nitro, oxo, and cyano.

As used herein, the term "alkylthio" refers to an alkyl group having a sulfur atom that connects the alkyl group to the point of attachment: i.e., alkyl-S—. As for alkyl groups, alkylthio groups can have any suitable number of carbon atoms, such as $C_{1-6}$ or $C_{1-4}$. Alkylthio groups include, for example, methoxy, ethoxy, propoxy, iso-propoxy, butoxy, 2-butoxy, iso-butoxy, sec-butoxy, tert-butoxy, pentoxy, hexoxy, etc. Alkylthio groups can be optionally substituted with one or more moieties selected from halo, hydroxy, amino, alkylamino, alkoxy, haloalkyl, carboxy, amido, nitro, oxo, and cyano.

As used herein, the terms "halo" and "halogen" refer to fluorine, chlorine, bromine and iodine.

As used herein, the term "haloalkyl" refers to an alkyl moiety as defined above substituted with at least one halogen atom.

As used herein, the term "alkylsilyl" refers to a moiety —$SiR_3$, wherein at least one R group is alkyl and the other R groups are H or alkyl. The alkyl groups can be substituted with one more halogen atoms.

As used herein, the term "acyl" refers to a moiety —C(O)R, wherein R is an alkyl group.

As used herein, the term "oxo" refers to an oxygen atom that is double-bonded to a compound (i.e., O=).

As used herein, the term "carboxy" refers to a moiety —C(O)OH. The carboxy moiety can be ionized to form the carboxylate anion. "Alkyl carboxylate" refers to a moiety —C(O)OR, wherein R is an alkyl group as defined herein.

As used herein, the term "amino" refers to a moiety —$NR_3$, wherein each R group is H or alkyl.

As used herein, the term "amido" refers to a moiety —NRC(O)R or —C(O)$NR_2$, wherein each R group is H or alkyl.

As used herein, the term "organosilicon compound" means an organometallic compound that contains a carbon-silicon (C—Si) bond. Typically, silicon atoms in organosilicon compounds are tetravalent and possess a tetrahedral geometry. Compared to carbon-carbon bonds, C—Si bonds are typically longer and weaker, with slight polarization due to relatively higher carbon electronegativity. Organosilicon compounds commonly have properties similar to other organic compounds, including being colorless, hydrophobic, and flammable. Organosilicon compounds find use in a large number of industrial and commercial applications, including silicone compounds and silicon-derived products such as coatings, adhesives, and sealants. Organosilicons can function as insecticides and find utility in biotechnology applications. Non-limiting examples of biotechnology applications include antiviral, antiparasitic, and other drugs, as well as biocompatible coatings and components for medical devices. Organosilicon compounds also find utility as reagents in various synthetic organic chemistry applications.

The terms "protein," "peptide," and "polypeptide" are used interchangeably herein to refer to a polymer of amino acid residues, or an assembly of multiple polymers of amino acid residues. The terms apply to amino acid polymers in which one or more amino acid residues are an artificial chemical mimic of a corresponding naturally occurring amino acid, as well as to naturally occurring amino acid polymers and non-naturally occurring amino acid polymers.

The term "amino acid" includes naturally-occurring α-amino acids and their stereoisomers, as well as unnatural (non-naturally occurring) amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., side-chain) groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, 1993).

The term "oligonucleotide," "nucleic acid," "nucleotide," or "polynucleotide" refers to deoxyribonucleic acids (DNA) or ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), orthologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991), Ohtsuka et al., *J. Biol. Chem.* 260:2605-2608 (1985), and Rossolini et al., *Mol. Cell. Probes* 8:91-98 (1994)). The term nucleic acid is used interchangeably with gene, cDNA, and mRNA encoded by a gene.

The term "site-directed mutagenesis" refers to various methods in which specific changes are intentionally made introduced into a nucleotide sequence (i.e., specific nucleotide changes are introduced at pre-determined locations). Known methods of performing site-directed mutagenesis include, but are not limited to, PCR site-directed mutagenesis, cassette mutagenesis, whole plasmid mutagenesis, and Kunkel's method.

The term "site-saturation mutagenesis," also known as "saturation mutagenesis," refers to a method of introducing random mutations at predetermined locations with a nucleotide sequence, and is a method commonly used in the context of directed evolution (e.g., the optimization of proteins (e.g., in order to enhance activity, stability, and/or stability), metabolic pathways, and genomes). In site-saturation mutagenesis, artificial gene sequences are synthesized using one or more primers that contain degenerate codons; these degenerate codons introduce variability into the position(s) being optimized. Each of the three positions within a degenerate codon encodes a base such as adenine (A), cytosine (C), thymine (T), or guanine (G), or encodes a degenerate position such as K (which can be G or T), M (which can be A or C), R (which can be A or G), S (which can be C or G), W (which can be A or T), Y (which can be C or T), B (which can be C, G, or T), D (which can be A, G, or T), H (which can be A, C, or T), V (which can be A, C, or G), or N (which can be A, C, G, or T). Thus, as a non-limiting example, the degenerate codon NDT encodes an A, C, G, or T at the first position, an A, G, or T at the second position, and a T at the third position. This particular combination of 12 codons represents 12 amino acids (Phe, Leu, Ile, Val, Tyr, His, Asn, Asp, Cys, Arg, Ser, and Gly). As another non-limiting example, the degenerate codon VHG encodes an A, C, or G at the first position, an A, C, or T at the second position, and G at the third position. This particular combination of 9 codons represents 8 amino acids (Lys, Thr, Met, Glu, Pro, Leu, Ala, and Val). As another non-limiting example, the "fully randomized" degenerate codon NNN includes all 64 codons and represents all 20 naturally-occurring amino acids.

In some instances, a mixture of degenerate primers is used. A mixture of degenerate primers can contain any number of different degenerate primers in any ratio. As a non-limiting example, a mixture of primers containing the NDT, VHG, and TGG primers can be used. Such a mixture can cotain, for example, an amount of each primer in a 12:9:1 ratio (e.g., a NDT:VHG:TGG ratio of 12:9:1). Based on various considerations, non-limiting examples being desired redundancy, the desired presence of stop codons, and/or desired amino acid characteristics (e.g., the presence of nonpolar residues, charged residues, or small side chain residues), different combinations of degenerate primers can be used. Considerations and methods for choosing optimal combinations of degenerate primers will be known to one of skill in the art.

The term "nucleotide sequence encoding a peptide" means the segment of DNA involved in producing a peptide chain. The term can include regions preceding and following the coding region (leader and trailer) involved in the transcription/translation of a gene product and the regulation of the transcription/translation, as well as intervening sequences (introns) between individual coding segments (exons).

The term "homolog," as used herein with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In particular embodiments, the homology between two proteins is indicative of its shared ancestry, related by evolution.

III. Description of the Embodiments

A. Heme Proteins

In certain aspects, the present invention provides compositions comprising one or more heme proteins that catalyze the formation of organosilicon compounds from silicon-containing reagents and carbene precursors. In particular embodiments, the present invention provides heme protein variants comprising one or more amino acid mutations therein that catalyze carbene insertion into silicon-hydrogen bonds, making organosilicon products with high stereoselectivity. In preferred embodiments, the heme protein variants of the present invention have the ability to form carbon-silicon bonds efficiently, display increased total turnover numbers, and/or demonstrate highly regio- and/or enantioselective product formation compared to the corresponding wild-type enzymes.

The terms "heme protein" and "heme enzyme" are used herein to include any member of a group of proteins containing heme as a prosthetic group. Non-limiting examples of heme proteins include globins, cytochromes, oxidoreductases, any other protein containing a heme as a prosthetic group, and combinations thereof. Heme-containing globins include, but are not limited to, hemoglobin, myoglobin, and combinations thereof. Heme-containing cytochromes include, but are not limited to, cytochrome P450, cytochrome b, cytochrome c1, cytochrome c, and combinations thereof. Heme-containing oxidoreductases include, but are not limited to, catalases, oxidases, oxygenases, haloperoxidases, peroxidases, and combinations thereof. In some instances, the globin protein is from *Methylacidiphilum infernorum*. In some other instances, the cytochrome P450 protein is a cytochrome P450 BM3 (CYP102A1) protein.

In certain instances, the heme proteins are metal-substituted heme proteins containing protoporphyrin IX or other porphyrin molecules containing non-native cofactors (i.e., metals other than iron), including, but not limited to, cobalt, rhodium, copper, ruthenium, iridium, and manganese, which are active carbon-silicon bond formation catalysts.

In some embodiments, the heme protein is a member of one of the enzyme classes set forth in Table 1. In other embodiments, the heme protein is a variant or homolog of a member of one of the enzyme classes set forth in Table 1. In yet other embodiments, the heme protein comprises or consists of the heme domain of a member of one of the enzyme classes set forth in Table 1 or a fragment thereof (e.g., a truncated heme domain) that is capable of carrying out the carbene insertion reactions described herein.

TABLE 1

Heme enzymes identified by their enzyme classification number (EC number) and classification name

| EC Number | Name |
|---|---|
| 1.1.2.3 | L-lactate dehydrogenase |
| 1.1.2.6 | polyvinyl alcohol dehydrogenase (cytochrome) |

TABLE 1-continued

Heme enzymes identified by their enzyme classification number (EC number) and classification name

| EC Number | Name |
|---|---|
| 1.1.2.7 | methanol dehydrogenase (cytochrome c) |
| 1.1.5.5 | alcohol dehydrogenase (quinone) |
| 1.1.5.6 | formate dehydrogenase-N: |
| 1.1.9.1 | alcohol dehydrogenase (azurin): |
| 1.1.99.3 | gluconate 2-dehydrogenase (acceptor) |
| 1.1.99.11 | fructose 5-dehydrogenase |
| 1.1.99.18 | cellobiose dehydrogenase (acceptor) |
| 1.1.99.20 | alkan-1-ol dehydrogenase (acceptor) |
| 1.2.1.70 | glutamyl-tRNA reductase |
| 1.2.3.7 | indole-3-acetaldehyde oxidase |
| 1.2.99.3 | aldehyde dehydrogenase (pyrroloquinoline-quinone) |
| 1.3.1.6 | fumarate reductase (NADH): |
| 1.3.5.1 | succinate dehydrogenase (ubiquinone) |
| 1.3.5.4 | fumarate reductase (menaquinone) |
| 1.3.99.1 | succinate dehydrogenase |
| 1.4.9.1 | methylamine dehydrogenase (amicyanin) |
| 1.4.9.2. | aralkylamine dehydrogenase (azurin) |
| 1.5.1.20 | methylenetetrahydrofolate reductase [NAD(P)H] |
| 1.5.99.6 | spermidine dehydrogenase |
| 1.6.3.1 | NAD(P)H oxidase |
| 1.7.1.1 | nitrate reductase (NADH) |
| 1.7.1.2 | Nitrate reductase [NAD(P)H] |
| 1.7.1.3 | nitrate reductase (NADPH) |
| 1.7.1.4 | nitrite reductase [NAD(P)H] |
| 1.7.1.14 | nitric oxide reductase [NAD(P), nitrous oxide-forming] |
| 1.7.2.1 | nitrite reductase (NO-forming) |
| 1.7.2.2 | nitrite reductase (cytochrome; ammonia-forming) |
| 1.7.2.3 | trimethylamine-N-oxide reductase (cytochrome c) |
| 1.7.2.5 | nitric oxide reductase (cytochrome c) |
| 1.7.2.6 | hydroxylamine dehydrogenase |
| 1.7.3.6 | hydroxylamine oxidase (cytochrome) |
| 1.7.5.1 | nitrate reductase (quinone) |
| 1.7.5.2 | nitric oxide reductase (menaquinol) |
| 1.7.6.1 | nitrite dismutase |
| 1.7.7.1 | ferredoxin-nitrite reductase |
| 1.7.7.2 | ferredoxin-nitrate reductase |
| 1.7.99.4 | nitrate reductase |
| 1.7.99.8 | hydrazine oxidoreductase |
| 1.8.1.2 | sulfite reductase (NADPH) |
| 1.8.2.1 | sulfite dehydrogenase |
| 1.8.2.2 | thiosulfate dehydrogenase |
| 1.8.2.3 | sulfide-cytochrome-c reductase (flavocytochrome c) |
| 1.8.2.4 | dimethyl sulfide: cytochrome c2 reductase |
| 1.8.3.1 | sulfite oxidase |
| 1.8.7.1 | sulfite reductase (ferredoxin) |
| 1.8.98.1 | CoB-CoM heterodisulfide reductase |
| 1.8.99.1 | sulfite reductase |
| 1.8.99.2 | adenylyl-sulfate reductase |
| 1.8.99.3 | hydrogensulfite reductase |
| 1.9.3.1 | cytochrome-c oxidase |
| 1.9.6.1 | nitrate reductase (cytochrome) |
| 1.10.2.2 | ubiquinol-cytochrome-c reductase |
| 1.10.3.1 | catechol oxidase |
| 1.10.3.B1 | caldariellaquinol oxidase (H+-transporting) |
| 1.10.3.3 | L-ascorbate oxidase |
| 1.10.3.9 | photosystem II |
| 1.10.3.10 | ubiquinol oxidase (H+-transporting) |
| 1.10.3.11 | ubiquinol oxidase |
| 1.10.3.12 | menaquinol oxidase (H+-transporting) |
| 1.10.9.1 | plastoquinol-plastocyanin reductase |
| 1.11.1.5 | cytochrome-c peroxidase |
| 1.11.1.6 | catalase |
| 1.11.1.7 | peroxidase |
| 1.11.1.B2 | chloride peroxidase (vanadium-containing) |
| 1.11.1.B7 | bromide peroxidase (heme-containing) |
| 1.11.1.8 | iodide peroxidase |
| 1.11.1.10 | chloride peroxidase |
| 1.11.1.11 | L-ascorbate peroxidase |
| 1.11.1.13 | manganese peroxidase |
| 1.11.1.14 | lignin peroxidase |
| 1.11.1.16 | versatile peroxidase |
| 1.11.1.19 | dye decolorizing peroxidase |
| 1.11.1.21 | catalase-peroxidase |
| 1.11.2.1 | unspecific peroxygenase |
| 1.11.2.2 | myeloperoxidase |

TABLE 1-continued

Heme enzymes identified by their enzyme classification number (EC number) and classification name

| EC Number | Name |
|---|---|
| 1.11.2.3 | plant seed peroxygenase |
| 1.11.2.4 | fatty-acid peroxygenase |
| 1.12.2.1 | cytochrome-c3 hydrogenase |
| 1.12.5.1 | hydrogen:quinone oxidoreductase |
| 1.12.99.6 | hydrogenase (acceptor) |
| 1.13.11.9 | 2,5-dihydroxypyridine 5,6-dioxygenase |
| 1.13.11.11 | tryptophan 2,3-dioxygenase |
| 1.13.11.49 | chlorite O2-lyase |
| 1.13.11.50 | acetylacetone-cleaving enzyme |
| 1.13.11.52 | indoleamine 2,3-dioxygenase |
| 1.13.11.60 | linoleate 8R-lipoxygenase |
| 1.13.99.3 | tryptophan 2'-dioxygenase |
| 1.14.11.9 | flavanone 3-dioxygenase |
| 1.14.12.17 | nitric oxide dioxygenase |
| 1.14.13.39 | nitric-oxide synthase (NADPH dependent) |
| 1.14.13.17 | cholesterol 7alpha-monooxygenase |
| 1.14.13.41 | tyrosine N-monooxygenase |
| 1.14.13.70 | sterol 14alpha-demethylase |
| 1.14.13.71 | N-methylcoclaurine 3'-monooxygenase |
| 1.14.13.81 | magnesium-protoporphyrin IX monomethyl ester (oxidative) cyclase |
| 1.14.13.86 | 2-hydroxyisoflavanone synthase |
| 1.14.13.98 | cholesterol 24-hydroxylase |
| 1.14.13.119 | 5-epiaristolochene 1,3-dihydroxylase |
| 1.14.13.126 | vitamin D3 24-hydroxylase |
| 1.14.13.129 | beta-carotene 3-hydroxylase |
| 1.14.13.141 | cholest-4-en-3-one 26-monooxygenase |
| 1.14.13.142 | 3-ketosteroid 9alpha-monooxygenase |
| 1.14.13.151 | linalool 8-monooxygenase |
| 1.14.13.156 | 1,8-cineole 2-endo-monooxygenase |
| 1.14.13.159 | vitamin D 25-hydroxylase |
| 1.14.14.1 | unspecific monooxygenase |
| 1.14.15.1 | camphor 5-monooxygenase |
| 1.14.15.6 | cholesterol monooxygenase (side-chain-cleaving) |
| 1.14.15.8 | steroid 15beta-monooxygenase |
| 1.14.15.9 | spheroidene monooxygenase |
| 1.14.18.1 | tyrosinase |
| 1.14.19.1 | stearoyl-CoA 9-desaturase |
| 1.14.19.3 | linoleoyl-CoA desaturase |
| 1.14.21.7 | biflaviolin synthase |
| 1.14.99.1 | prostaglandin-endoperoxide synthase |
| 1.14.99.3 | heme oxygenase |
| 1.14.99.9 | steroid 17alpha-monooxygenase |
| 1.14.99.10 | steroid 21-monooxygenase |
| 1.14.99.15 | 4-methoxybenzoate monooxygenase (O-demethylating) |
| 1.14.99.45 | carotene epsilon-monooxygenase |
| 1.16.5.1 | ascorbate ferrireductase (transmembrane) |
| 1.16.9.1 | iron:rusticyanin reductase |
| 1.17.1.4 | xanthine dehydrogenase |
| 1.17.2.2 | lupanine 17-hydroxylase (cytochrome c) |
| 1.17.99.1 | 4-methylphenol dehydrogenase (hydroxylating) |
| 1.17.99.2 | ethylbenzene hydroxylase |
| 1.97.1.1 | chlorate reductase |
| 1.97.1.9 | selenate reductase |
| 2.7.7.65 | diguanylate cyclase |
| 2.7.13.3 | histidine kinase |
| 3.1.4.52 | cyclic-guanylate-specific phosphodiesterase |
| 4.2.1.B9 | colneleic acid/etheroleic acid synthase |
| 4.2.1.22 | Cystathionine beta-synthase |
| 4.2.1.92 | hydroperoxide dehydratase |
| 4.2.1.212 | colneleate synthase |
| 4.3.1.26 | chromopyrrolate synthase |
| 4.6.1.2 | guanylate cyclase |
| 4.99.1.3 | sirohydrochlorin cobaltochelatase |
| 4.99.1.5 | aliphatic aldoxime dehydratase |
| 4.99.1.7 | phenylacetaldoxime dehydratase |
| 5.3.99.3 | prostaglandin-E synthase |
| 5.3.99.4 | prostaglandin-I synthase |
| 5.3.99.5 | Thromboxane-A synthase |
| 5.4.4.5 | 9,12-octadecadienoate 8-hydroperoxide 8R-isomerase |
| 5.4.4.6 | 9,12-octadecadienoate 8-hydroperoxide 8S-isomerase |
| 6.6.1.2 | cobaltochelatase |

In particular embodiments, the heme protein is a variant or a fragment thereof (e.g., a truncated variant containing the heme domain) comprising at least one mutation, e.g., a mutation at the axial position of the heme coordination site. In some instances, the mutation is a substitution of the native residue with Ala, Asp, Arg, Asn, Cys, Glu, Gln, Gly, His, Ile, Lys, Leu, Met, Phe, Pro, Ser, Thr, Trp, Tyr, or Val at the axial position. In certain instances, the mutation is a substitution of Met with any other amino acid such as Asp or Glu at the axial position.

In certain embodiments, the heme protein, variant thereof, or homolog thereof comprises or consists of the same number of amino acid residues as the wild-type protein (e.g., a full-length polypeptide). In some instances, the heme protein, variant thereof, or homolog thereof comprises or consists of a fragment of the full-length protein (e.g., Rma cyt c amino acid sequence set forth in SEQ ID NO:1).

In some embodiments, the heme enzyme comprises a globin enzyme. Globins are a superfamily of globular heme proteins that are typically involved in the transport and binding of oxygen. A characteristic of globins is a three-dimensional fold consisting of eight alpha helices, although some globins have additional terminal helix extensions. Globins can be divided into three groups: single-domain globins, flavohemoglobins (not observed in archaea), and globin-coupled sensors (not observed in eukaryotes). All three groups are observed in bacteria. Globin proteins include hemoglobin, myoglobin, neuroglobin, cytoglobin, erythrocruorin, leghemoglobin, non-symbiotic hemoglobin, flavohemoglobins (one group of chimeric globins), globin E, globin-coupled sensors (another group of chimeric globins), protoglobin, truncated 2/2 globin, HbN, cyanoglobin, HbO, and Glb3.

In other embodiments, the heme enzyme comprises an oxidoreductase. Oxidoreductases are enzymes that catalyze the transfer of electrons from a reductant (i.e., an electron donor) to an oxidant (i.e., an electron acceptor) and are divided into 22 subclasses. Oxidoreductases typically utilize NADP or NAD+ as a cofactor. EC 1.1 oxidoreductases (alcohol oxidoreductases) act on the CH—OH group of donors. EC 1.2 oxidoreductases act on the aldehyde or oxo group of donors. EC 1.3 oxidoreductases (CH—CH oxidoreductases) act on the CH—CH group of donors. EC 1.4 oxidoreductases (amino acid oxidoreductases, monoamine oxidase) act on the CH—$NH_2$ group of donors. EC 1.5 oxidoreductases act on the CH—NH group of donors. EC 1.6 oxidoreductases act on NADH or NADPH. EC 1.7 oxidoreductases act on other nitrogenous compounds as donors. EC 1.8 oxidoreductases act on a sulfur group of donors. EC 1.9 oxidoreductases act on a heme group of donors. EC 1.10 oxidoreductases act on diphenols and related substances as donors. EC 1.11 oxidoreductases (peroxidases) act on peroxide as an acceptor. EC 1.12 oxidoreductases act on hydrogen as donors. EC 1.13 oxidoreductases (oxygenases) act on single donors with incorporation of molecular oxygen. EC 1.14 oxidoreductases act on paired donors with incorporation of molecular oxygen. EC 1.15 oxidoreductases act on superoxide radicals as acceptors. EC 1.16 oxidoreductases oxidize metal ions. EC 1.17 oxidoreductases act on CH or $CH_2$ groups. EC 1.18 oxidoreductases act on iron-sulfur proteins as donors. EC 1.19 oxidoreductases act on reduced flavodoxin as a donor. EC 1.20 oxidoreductases act on phosphorous or arsenic in donors. EC 1.21 oxidoreductases act on X—H and Y—H to form an X—Y bond. Enzyme classification number 1.97 includes other oxidoreductases that do not fit into any of the aforementioned subclasses. Haloperoxidases are peroxidases that mediate halide oxidation by hydrogen peroxide (EC 1.11.1). Catalases catalyze the decomposition of hydrogen peroxide to oxygen and water (EC 1.11.1.6).

In some embodiments, the heme enzyme comprises a cytochrome. Cytochromes are a class of heme proteins that are found in bacteria, as well as mitochondria and chloroplasts of eukaryotic organisms, and are typically associated with membranes. Cytochromes typically function in oxidative phosphorylation as components of electron transport chain systems. Cytochromes can be classified by spectroscopy, or by features such as the structure of the heme group, inhibitor sensitivity, or reduction potential. Three of the cytochromes, cytochromes a, b, and d, are classified by their prosthetic group (the prosthetic groups consisting of heme a, heme b, and tetrapyrrolic chelate of iron, respectively). Unlike the aforementioned cytochromes, cytochrome c is not defined in terms of its heme group. Cytochrome $f$, which performs similar functions to cytochrome $c_1$ but has a different structure, is sometimes regarded as a type of cytochrome c. Cytochrome P450 proteins form a distinct family of cytochromes.

In bacteria, mitochondria, and chloroplasts, various cytochromes form different combinations to that perform different functions. Cytochromes a and $a_3$ combine to form cytochrome c oxidase (also known as Complex IV), which is the last enzyme in the respiratory chain of bacteria and mitochondria. Cytochromes b and $c_1$ combine to form coenzyme Q—cytochrome c reductase—the third complex in the electron transport chain. Cytochromes $b_6$ and $f$ combine to form plastoquinol-plastocyanin reductase, which is found in the chloroplasts of plants, cyanobacteria and green algae and functions in photosynthesis.

Cytochrome P450 enzymes constitute a large superfamily of heme-thiolate proteins involved in the metabolism of a wide variety of both exogenous and endogenous compounds. Usually, they act as the terminal oxidase in multi-component electron transfer chains, such as P450-containing monooxygenase systems. Members of the cytochrome P450 enzyme family catalyze myriad oxidative transformations, including, e.g., hydroxylation, epoxidation, oxidative ring coupling, heteroatom release, and heteroatom oxygenation (E. M. Isin et al., *Biochim. Biophys. Acta* 1770, 314 (2007)). The active site of these enzymes contains an $Fe^{III}$-protoporphyrin IX cofactor (heme) ligated proximally by a conserved cysteine thiolate (M. T. Green, *Current Opinion in Chemical Biology* 13, 84 (2009)). The remaining axial iron coordination site is occupied by a water molecule in the resting enzyme, but during native catalysis, this site is capable of binding molecular oxygen. In the presence of an electron source, typically provided by NADH or NADPH from an adjacent fused reductase domain or an accessory cytochrome P450 reductase enzyme, the heme center of cytochrome P450 activates molecular oxygen, generating a high valent iron(IV)-oxo porphyrin cation radical species intermediate and a molecule of water.

Cytochrome P450 BM3 (CYP102A1) proteins are found in the soil bacterium *Bacillus megaterium* and catalyze the NADPH-dependent hydroxylation of long-chain fatty acids at the ω-1 through ω-3 positions. Unlike most other cytochrome P450 proteins, cytochrome P450 BM3 proteins are a natural fusion between the cytochrome P450 domain and an electron donating cofactor. Thus, cytochrome P450 BM3 proteins are useful in a number of biotechnological applications.

Cytochrome c proteins are a superfamily of proteins that have one or more covalently bound heme prosthetic groups (i.e., heme c groups). Generally, the heme groups are bound to the protein by one, or more typically two, thioether bonds involving sulphydryl groups of cysteine residues. This superfamily of proteins possesses a characteristic CXXCH amino acid motif that binds heme, wherein X can be any amino acid. The fifth heme iron ligand is provided by a histidine residue. Cytochrome c proteins possess a wide range of characteristics, enabling them to function in a large number of redox processes.

Cytochrome c is highly conserved across the spectrum of species. Non-limiting examples of cytochrome c amino acid sequences (encoded by the CYCS gene) can be found in NCBI Reference Sequence No. NM_018947.54→NP_061820.1 (human), NCBI Reference Sequence No. NM_007808.44→NP_031834.1 (mouse), and NCBI Reference No. ACA83734.1 (*Rhodothermus marinus* unprocessed; SEQ ID NO:2).

Cytochrome c proteins fall into one of four classes. Class I contains soluble, low spin single domain C-type cytochromes. There are at least six subclasses of Class 1 cytochrome c proteins that are found in prokaryotes including *Desulfovibrio desulfuricans*, *Rhodospirillum rubrum*, *Rhodopila globiformis*, and *Rhodothermus marinus* (Rma). Class I proteins have a single heme that is attached near the N-terminus of the polypeptide, with a methionine residue being the sixth iron coordination site. Class II contains higher spin-state cytochromes c, with the heme prosthetic group being attached closer to the C-terminus. Class III contains cytochromes with multiple heme groups. These proteins have lower redox potentials compared to the other three classes. Class IV contains more complex proteins having higher molecular weights. Class IV proteins contain heme c as well as other prosthetic groups.

In some embodiments, the cytochrome c protein is selected from the group consisting of *Rhodothermus marinus* (Rma) cytochrome c, *Rhodopila globiformis* cytochrome c, *Hydrogenobacter thermophilus* cytochrome c, *Saccharomyces cerevisiae* cytochrome c, horse heart cytochrome c, bovine heart cytochrome c, and a combination thereof.

In preferred embodiments, the cytochrome c protein variant comprises a mutation at one or more of the conserved residues of the corresponding wild-type sequence that serve as heme axial ligands. In certain preferred embodiments, the cytochrome c protein variant comprises one or more mutations at one or more conserved residues of the corresponding wild-type sequences that reside near (e.g., about 7 Å) the heme center. As a non-limiting example, an axial variant of Rma cyt c can comprise a M100 mutation relative to the amino acid sequence set forth in SEQ ID NO:1. In some instances, the mutation is an M100D or M100E mutation. As another other non-limiting example, a variant of Rma cyt c can comprise a mutation at V75 relative to the amino acid sequence set forth in SEQ ID NO:1. In some instances, the mutation is a V75T mutation. As another other non-limiting example, a variant of Rma cyt c can comprise a mutation at M103 relative to the amino acid sequence set forth in SEQ ID NO: 1. In some instances, the mutation is an M103E mutation.

In some other embodiments, the Rma cyt c protein variant comprises a combination of mutations (e.g., the Rma cyt c protein variant is a V75 M100 mutant, a V75 M103 mutant, an M100 M103 mutant, or a V75 M100 M103 mutant, relative to the amino acid sequence set forth in SEQ ID NO:1). In some instances, the Rma cyt c protein variant is a V75T M100D or V75T M100E mutant relative to the amino acid sequence set forth in SEQ ID NO:1. In other instances, the Rma cyt c protein variant is a V75T M103E mutant relative to the amino acid sequence set forth in SEQ ID NO:1. In some instances, the Rma cyt c protein variant is an M100D M103E or M100E or M103E mutant relative to the amino acid sequence set forth in SEQ ID NO:1. In other instances, the Rma cyt c protein variant is a V75T M100D M103E or V75T M100E M103E mutant relative to the amino acid sequence set forth in SEQ ID NO:1.

In some embodiments, the heme protein comprises an amino acid sequence that has about 70% or greater (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to the amino acid sequence set forth in SEQ ID NO:1. In other embodiments, the heme protein comprises an amino acid sequence that has about 80% or greater (e.g., about 80%, 81%, 82%, 83%, 84%, 85%, 86%, 87%, 88%, 89%, 90%, 91%, 92%, 93%, 94%, 95%, 96%, 97%, 98%, 99%, or 100%) identity to the amino acid sequence set forth in SEQ ID NO: 1. In particular embodiments, the heme protein comprises an amino acid sequence that has about 90% or greater (e.g., about 90%, 91%, 92%, 93%, 94%, 95%, 96%, 97%, 98%, 99%, or 100%) identity to the amino acid sequence set forth in SEQ ID NO:1. In some instances, the heme protein comprises an amino acid sequence that is about 95%, 96,%, 97%, 98%, 99%, or 100% identical to the amino acid sequence set forth in SEQ ID NO:1.

In other embodiments, the heme protein comprises an amino acid sequence that contains between about 5 and 124 (e.g., about 5, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, or 124) of the amino acids in SEQ ID NO:1. The amino acids may be contiguous, or separated by any number of amino acids.

In some embodiments, the heme protein comprises an amino acid sequence that has about 70% or greater (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to the amino acid sequence set forth in SEQ ID NO:2. In other embodiments, the heme protein comprises an amino acid sequence that has about 80% or greater (e.g., about 80%, 81%, 82%, 83%, 84%, 85%, 86%, 87%, 88%, 89%, 90%, 91%, 92%, 93%, 94%, 95%, 96%, 97%, 98%, 99%, or 100%) identity to the amino acid sequence set forth in SEQ ID NO:2. In particular embodiments, the heme protein comprises an amino acid sequence that has about 90% or greater (e.g., about 90%, 91%, 92%, 93%, 94%, 95%, 96%, 97%, 98%, 99%, or 100%) identity to the amino acid sequence set forth in SEQ ID NO:2. In some instances, the heme protein comprises an amino acid sequence that is about 95%, 96,%, 97%, 98%, 99%, or 100% identical to the amino acid sequence set forth in SEQ ID NO:2.

In other embodiments, the heme protein comprises an amino acid sequence that contains between about 5 and 152 (e.g., about 5, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, or 152) of the amino acids in SEQ ID NO:2. The amino acids may be contiguous, or separated by any number of amino acids.

In certain embodiments, the conserved residue in a heme protein of interest that serves as the heme axial ligand can be identified by locating the segment of the DNA sequence in the corresponding cytochrome c gene which encodes the conserved residue. In some instances, this DNA segment is identified through detailed mutagenesis studies in a conserved region of the protein. In other instances, the conserved residue is identified through crystallographic study.

In situations where detailed mutagenesis studies and crystallographic data are not available for a heme protein of interest, the axial ligand may be identified through phylogenetic study. Due to the similarities in amino acid sequence within families of heme proteins (e.g., cytochrome c proteins), standard protein alignment algorithms may show a phylogenetic similarity between a heme protein for which crystallographic or mutagenesis data exist and a new heme protein for which such data do not exist. Thus, the polypeptide sequences of the present invention for which the heme axial ligand is known can be used as a "query sequence" to perform a search against a specific new heme protein of interest or a database comprising heme protein sequences to identify the heme axial ligand. Such analyses can be performed using the BLAST programs (see, e.g., Altschul et al., *J Mol Biol.* 215(3):403-10(1990)). Software for performing BLAST analyses is publicly available through the National Center for Biotechnology Information (ncbi.nlm.nih.gov). BLASTP is used for amino acid sequences.

Exemplary parameters for performing amino acid sequence alignments to identify the heme axial ligand in a heme protein of interest using the BLASTP algorithm include E value=10, word size=3, Matrix=Blosum62, Gap opening=11, gap extension=1, and conditional compositional score matrix adjustment. Those skilled in the art will know what modifications can be made to the above parameters, e.g., to either increase or decrease the stringency of the comparison and/or to determine the relatedness of two or more sequences.

In certain embodiments, mutations can be introduced into the target gene using standard cloning techniques (e.g., site-directed mutagenesis, site-saturated mutagenesis) or by gene synthesis to produce the heme proteins, fragments thereof, variants thereof, or homologs thereof of the present invention.

In some embodiments, the heme protein, fragment thereof, variant thereof, or homolog thereof is recombinantly expressed and optionally isolated and/or purified for carrying out the in vitro silicon-hydrogen carbene insertion reactions of the present invention. In other embodiments, the heme protein, fragment thereof, variant thereof, or homolog thereof is expressed in whole cells such as bacterial cells, archaeal cells, yeast cells, fungal cells, insect cells, plant cells, or mammalian cells, and these cells are used for carrying out the in vivo silicon-hydrogen carbene insertion reactions of the present invention. The wild-type or mutated gene can be expressed in a whole cell using an expression vector under the control of an inducible promoter or by means of chromosomal integration under the control of a constitutive promoter. Silicon-hydrogen carbene insertion activity can be screened in vivo or in vitro by following product formation by GC or HPLC.

Suitable bacterial host cells include, but are not limited to, BL21 *E. coli*, DE3 strain *E. coli*, *E. coli* M15, DH5α, DH10β, HB101, T7 Express Competent *E. coli* (NEB), *B. subtilis* cells, *Pseudomonas fluorescens* cells, and cyanobacterial cells such as *Chlamydomonas reinhardtii* cells and *Synechococcus elongates* cells. Non-limiting examples of archaeal host cells include *Pyrococcus furiosus*, *Metallo-*

*sphera sedula, Thermococcus litoralis, Methanobacterium thermoautotrophicum, Methanococcus jannaschii, Pyrococcus abyssi, Sulfolobus solfataricus, Pyrococcus woesei, Sulfolobus shibatae*, and variants thereof. Fungal host cells include, but are not limited to, yeast cells from the genera *Saccharomyces* (e.g., *S. cerevisiae*), *Pichia* (P. *Pastoris*), *Kluyveromyces* (e.g., *K. lactis*), *Hansenula* and *Yarrowia*, and filamentous fungal cells from the genera *Aspergillus, Trichoderma*, and *Myceliophthora*. Suitable insect host cells include, but are not limited to, Sf9 cells from *Spodoptera frugiperda*, Sf21 cells from *Spodoptera frugiperda*, Hi-Five cells, BTI-TN-5B1-4 *Trichophusia ni* cells, and Schneider 2 (S2) cells and Schneider 3 (S3) cells from *Drosophila melanogaster*. Non-limiting examples of mammalian host cells include HEK293 cells, HeLa cells, CHO cells, COS cells, Jurkat cells, NSO hybridoma cells, baby hamster kidney (BHK) cells, MDCK cells, NIH-3T3 fibroblast cells, and any other immortalized cell line derived from a mammalian cell. Non-limiting examples of plant host cells include those from tobacco, tomato, potato, maize, rice, lettuce, and spinach. In general, cells from plants that have short generation times and/or yield reasonable biomass with standard cultivation techniques are preferable.

In certain embodiments, the present invention provides the heme proteins, fragments thereof, variants thereof, or homologs thereof, such as the cytochrome c variants described herein that are active silicon-hydrogen carbene insertion catalysts, inside living cells. As a non-limiting example, bacterial cells (e.g., *E. coli*) can be used as host whole cell catalysts for the in vivo silicon-hydrogen carbene insertion reactions of the present invention, although any number of host whole cells may be used, including but not limited to the host cells described herein. In some embodiments, host whole cell catalysts containing heme proteins, fragments thereof, variants thereof, or homologs thereof are found to significantly enhance the total turnover number (TTN) compared to the in vitro reactions using isolated heme proteins, fragments thereof, variants thereof, or homologs thereof.

The expression vector comprising a nucleic acid sequence that encodes a heme protein, fragment thereof, variant thereof, or homolog thereof of the invention can be a viral vector, a plasmid, a phage, a phagemid, a cosmid, a fosmid, a bacteriophage (e.g., a bacteriophage P1-derived vector (PAC)), a baculovirus vector, a yeast plasmid, or an artificial chromosome (e.g., bacterial artificial chromosome (BAC), a yeast artificial chromosome (YAC), a mammalian artificial chromosome (MAC), and human artificial chromosome (HAC)). Expression vectors can include chromosomal, non-chromosomal, and synthetic DNA sequences. Equivalent expression vectors to those described herein are known in the art and will be apparent to the ordinarily skilled artisan.

The expression vector can include a nucleic acid sequence encoding a heme protein, fragment thereof, variant thereof, or homolog thereof that is operably linked to a promoter, wherein the promoter comprises a viral, bacterial, archaeal, fungal, insect, plant, or mammalian promoter. In certain embodiments, the promoter is a constitutive promoter. In some embodiments, the promoter is an inducible promoter. In other embodiments, the promoter is a tissue-specific promoter or an environmentally regulated or a developmentally regulated promoter.

In some embodiments, the nucleic acid sequence encodes a heme protein that comprises an amino acid sequence that has about 70% or greater (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to the amino acid sequence set forth in SEQ ID NO:1. In other embodiments, the nucleic acid sequence encodes a heme protein that comprises an amino acid sequence that has about 80% or greater (e.g., about 80%, 81%, 82%, 83%, 84%, 85%, 86%, 87%, 88%, 89%, 90%, 91%, 92%, 93%, 94%, 95%, 96%, 97%, 98%, 99%, or 100%) identity to the amino acid sequence set forth in SEQ ID NO:1. In particular embodiments, the nucleic acid sequence encodes a heme protein that comprises an amino acid sequence that has about 90% or greater (e.g., about 90%, 91%, 92%, 93%, 94%, 95%, 96%, 97%, 98%, 99%, or 100%) identity to the amino acid sequence set forth in SEQ ID NO: 1. In some instances, the nucleic acid sequence encodes a heme protein that comprises an amino acid sequence that is about 95%, 96,%, 97%, 98%, 99%, or 100% identical to the amino acid sequence set forth in SEQ ID NO:1.

In other embodiments, the nucleic acid sequence encodes a heme protein that comprises an amino acid sequence that contains between about 5 and 124 (e.g., about 5, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, or 124) of the amino acids in SEQ ID NO:1. The amino acids may be contiguous, or separated by any number of amino acids.

In some embodiments, the nucleic acid sequence encodes a heme protein that comprises an amino acid sequence that has about 70% or greater (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) identity to the amino acid sequence set forth in SEQ ID NO:2. In other embodiments, the nucleic acid sequence encodes a heme protein that comprises an amino acid sequence that has about 80% or greater (e.g., about 80%, 81%, 82%, 83%, 84%, 85%, 86%, 87%, 88%, 89%, 90%, 91%, 92%, 93%, 94%, 95%, 96%, 97%, 98%, 99%, or 100%) identity to the amino acid sequence set forth in SEQ ID NO:2. In particular embodiments, the nucleic acid sequence encodes a heme protein that comprises an amino acid sequence that has about 90% or greater (e.g., about 90%, 91%, 92%, 93%, 94%, 95%, 96%, 97%, 98%, 99%, or 100%) identity to the amino acid sequence set forth in SEQ ID NO:2. In some instances, the nucleic acid sequence encodes a heme protein that comprises an amino acid sequence that is about 95%, 96,%, 97%, 98%, 99%, or 100% identical to the amino acid sequence set forth in SEQ ID NO:2.

In other embodiments, the nucleic acid sequence encodes a heme protein that comprises an amino acid sequence that contains between about 5 and 152 (e.g., about 5, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, or 152) of the amino acids in SEQ ID NO:2. The amino acids may be contiguous, or separated by any number of amino acids.

It is understood that affinity tags may be added to the N- and/or C-terminus of a heme protein, fragment thereof, variant thereof, or homolog thereof expressed using an expression vector to facilitate protein purification. Non-limiting examples of affinity tags include metal binding tags such as His6-tags and other tags such as glutathione S-transferase (GST).

Non-limiting expression vectors for use in bacterial host cells include pCWori, pET vectors such as pET22 (EMD Millipore), pBR322 (ATCC37017), pQE™ vectors (Qiagen), pBluescript™ vectors (Stratagene), pNH vectors, lambda-ZAP vectors (Stratagene); ptrc99a, pKK223-3, pDR540, pRIT2T (Pharmacia), pRSET, pCR-TOPO vectors, pET vectors, pSyn_1 vectors, pChlamy_1 vectors (Life Technologies, Carlsbad, Calif.), pGEM1 (Promega, Madison, Wis.), and pMAL (New England Biolabs, Ipswich, Mass.). Non-limiting examples of expression vectors for use in eukaryotic host cells include pXT1, pSG5 (Stratagene), pSVK3, pBPV, pMSG, pSVLSV40 (Pharmacia), pcDNA3.3, pcDNA4/TO, pcDNA6/TR, pLenti6/TR, pMT vectors (Life Technologies), pKLAC1 vectors, pKLAC2 vectors (New England Biolabs), pQE™ vectors (Qiagen), BacPak baculoviral vectors, pAdeno-X™ adenoviral vectors (Clontech), and pBABE retroviral vectors. Any other vector may be used as long as it is replicable and viable in the host cell.

In some embodiments, the heme protein, homolog, variant, or fragment thereof has a turnover frequency (TOF) between about 1 $min^{-1}$ and 10 $min^{-1}$ (e.g., about 1 $min^{-1}$, 1.5 $min^{-1}$, 2 $min^{-1}$, 2.5 $min^{-1}$, 3 $min^{-1}$, 3.5 $min^{-1}$, 4 $min^{-1}$, 4.5 $min^{-1}$, 5 $min^{-1}$, 5.5 $min^{-1}$, 6 $min^{-1}$, 6.5 $min^{-1}$, 7 $min^{-1}$, 7.5 $min^{-1}$, 8 $min^{-1}$, 8.5 $min^{-1}$, 9 $min^{-1}$, 9.5 $min^{-1}$, or 10 $min^{-1}$). In other embodiments, the TOF is between about 10 $min^{-1}$ and 100 $min^{-1}$ (e.g., about 10 $min^{-1}$, 11 $min^{-1}$, 12 $min^{-1}$, 13 $min^{-1}$, 14 $min^{-1}$, 15 $min^{-1}$, 16 $min^{-1}$, 17 $min^{-1}$, 18 $min^{-1}$, 19 $min^{-1}$, 20 $min^{-1}$, 21 $min^{-1}$, 22 $min^{-1}$, 23 $min^{-1}$, 24 $min^{-1}$, 25 $min^{-1}$, 26 $min^{-1}$, 27 $min^{-1}$, 28 $min^{-1}$, 29 $min^{-1}$, 30 $min^{-1}$, 31 $min^{-1}$, 32 $min^{-1}$, 33 $min^{-1}$, 34 $min^{-1}$, 35 $min^{-1}$, 36 $min^{-1}$, 37 $min^{-1}$, 38 $min^{-1}$, 39 $min^{-1}$, 40 $min^{-1}$, 41 $min^{-1}$, 42 $min^{-1}$, 43 $min^{-1}$, 44 $min^{-1}$, 45 $min^{-1}$, 46 $min^{-1}$, 47 $min^{-1}$, 48 $min^{-1}$, 49 $min^{-1}$, 50 $min^{-1}$, 55 $min^{-1}$, 60 $min^{-1}$, 65 $min^{-1}$, 70 $min^{-1}$, 75 $min^{-1}$, 80 $min^{-1}$, 85 $min^{-1}$, 90 $min^{-1}$, 95 $min^{-1}$, or 100 $min^{-1}$). In other instances, the TOF is greater than about 100 $min^{-1}$ to 1,000 $min^{-1}$ (e.g., greater than about 100 $min^{-1}$, 150 $min^{-1}$, 200 $min^{-1}$, 250 $min^{-1}$, 300 $min^{-1}$, 350 $min^{-1}$, 400 $min^{-1}$, 450 $min^{-1}$, 500 $min^{-1}$, 550 $min^{-1}$, 600 $min^{-1}$, 650 $min^{-1}$, 700 $min^{-1}$, 750 $min^{-1}$, 800 $min^{-1}$, 850 $min^{-1}$, 900 $min^{-1}$, 950 $min^{-1}$, 1,000 $min^{-1}$, or more). In some instances, the TOF is greater than about 10 $min^{-1}$. In other instances, the TOF is greater than about 45 $min^{-1}$.

In other embodiments, the heme protein, homolog, variant, or fragment thereof has a total turnover number (TTN), which refers to the maximum number of molecules of a substrate that the protein can convert before becoming inactivated, of between about 1 and 100 (e.g., about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100). In some other embodiments, the TTN is between about 100 and 1,000 (e.g., about 100, 150, 200, 250, 300, 350, 400, 450, 500, 550, 600, 650, 700, 750, 800, 850, 900, 950, or 1,000). In some embodiments, the TTN is between about 1,000 and 2,000 (e.g., about 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950 or 2,000). In other embodiments, the TTN is at least about 2,000 (e.g., at least about 2,000, 2,500, 3,000, 3,500, 4,000, 4,500, 5,000, 5,500, 6,000, 6,500, 7,000, 7,500, 8,000, 8,500, 9,000, 9,500, or 10,000). In some instances, the TTN is greater than about 70. In other instances, the TTN is greater than about 1,800.

In some embodiments, the heme protein variant or fragment thereof has enhanced activity of at least about 1.5 to 2,000 fold (e.g., at least about 1.5, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, 2,000, or more) fold compared to the corresponding wild-type heme protein.

In some embodiments, activity is expressed in terms of turnover frequency (TOF). In particular embodiments, the TOF of the heme protein variant or fragment thereof is at least about 1.5, 2, 2.5, 3, 3.5, 4, 4.5, 5, 5.5, 6, 6.5, 7, 7.5, 8, 8.5, 9, 9.5, or 10 fold higher than the corresponding wild-type protein.

In other instances, activity is expressed in terms of total turnover number (TTN). In particular instances, the TTN of the theme protein variant or fragment thereof is about least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, or 2,000 fold higher than the corresponding wild-type protein.

In some embodiments, the present invention provides heme proteins, homologs, variants, and fragments thereof that catalyze enantioselective carbene insertion into silicon-hydrogen bonds with high enantiomeric excess. In particular embodiments, the heme proteins are variants or fragments thereof that catalyze enantioselective carbene insertion into silicon-hydrogen bonds with higher enantiomeric excess values than that of the corresponding wild-type protein. In some embodiments, the heme protein, homolog, variants, or fragment thereof catalyzes carbene insertion into silicon-hydrogen bonds with an enantiomeric excess value of at least about 30% ee (e.g., at least about 30%, 35%, 40%, 45%, 50%, 55%, 60%, 65%, 70%, 75%, 80%, 85%, 90%, 95%, or 100% ee). Preferably, the heme protein, homolog, variant, or fragment thereof catalyzes carbene insertion into silicon-hydrogen bonds with at least about 80% ee (e.g., at least about 80%, 81%, 82%, 83%, 84%, 85%, 86%, 87%, 88%, 89%, 90%, 91%, 92%, 93%, 94%, 95%, 96%, 97%, 98%, 99%, or 100% ee). More preferably, the heme protein, homolog, variant, or fragment thereof catalyzes carbene insertion into silicon-hydrogen bonds with at least about 95% ee (e.g., at least about 95%, 96%, 97%, 98%, 99%, or 100% ee).

B. Compounds

The methods of the invention can be used to provide a number of organosilicon products. The organosilicon products include several classes of compound including, but not limited to, silicone compounds and silicon-derived products (e.g., coatings, adhesives, and sealants), pharmaceutical compounds (i.e., drugs, therapeutic agents, etc.), biocompatible coatings, insecticides, and reagents for chemical synthesis. Examples of pharmaceutical compounds that can be prepared with the methods of the invention include, but are not limited to, antiviral agents, antiparasitic agents, protease inhibitors (including, e.g., silanol enzyme inhibitors described by Sieburth in U.S. Pat. Nos. 5,760,019 and 7,087,776), topoisomerase inhibitors (including, e.g., camptothecin analogs described in U.S. Pat. No. 5,910,491 and WO 98/07727), retinoids (including, e.g., bexarotene analogs described in WO 2004/048390), serotonin-norepinephrine reuptake inhibitors (including, e.g., venlafxine analogs described in WO 03/037905), and non-steroidal anti-inflammatory drugs (e.g., indomethacin analogs described in U.S. Pat. No. 7,964,738 and WO 2005/102358). Examples of insecticides that can be prepared with the methods of the invention include, but are not limited to, silafluofen and pyrethroids disclosed in U.S. Pat. Nos. 4,709,068 and 4,883,789.

Examples of reagents for coating materials that can be prepared with the methods of the invention include, but are not limited to, silanes, siloxanes, and polysiloxanes disclosed in U.S. Pat. Nos. 9,359,386; 8,952,118; 8,921,579; and 7,235,683.

Examples of reagents for chemical synthesis include, but are not limited to, amines (e.g., 4-amino-3,3-dimethylbutyl-methyldimethoxysilane, 1-amino-2-(dimethylethoxysilyl) propane, N-(2-aminoethyl)-3-aminoisobutyldimethyl-methoxysilane, and the like); amides (e.g., N-(trimethylsilyl)acetamide, N,O-bis(trimethylsilyl)acetamide, and the like); non-nantural amino acids (e.g., trimethylsilylphenyl-alanine, trimethylsilylalanine, dimethylphenylsilylalanine, silaproline, and the like); acrylamides (e.g., 3-acrylamidopropyltrimethoxysilane, 3-acrylamidopropyl-tris(trimethylsiloxy)silane, and the like); acrylates (e.g., acryloxymethyl-trimethoxysilane, (acryloxymethyl)phenethyltrimethoxysilane, and the like); aromatic silanes (e.g., bis (phenylethynyl)dimethylsilane, p-bromophenoxy-(t-butyl) dimethylsilane, N-benzyl-aminomethyltrimethylsilane, benzyldimethylchlorosilane, N-benzyl-N-methoxymethyl-N-(tri-methylsilylmethyl)amine, (phenylaminomethyl) methyldimeth-oxysilane, and the like); poly-cyclic silanes (e.g., [(5-bicyclo[2.2.1]hept-2-enyl)ethyl]trimethoxysilane, (5-bicyclo[2.2.1]hept-2-enyl)methyldiethoxysilane, (5-bicyclo[2.2.1]heptyl)dimethyl-chlorosilane, adamantylethyltrichlorosilane, and the like); heteroaromatic silanes (e.g., bis(1-imidazolyl)dimethylsilane, 3-(2-pyridylethyl)thiopropyltrimethoxysilane, 2-pyridyltrimethyl-silane, and the like); heterocyclic silanes (e.g., 2,2-bis(trimethylsilyl)-1,3-dithiane, bis(trimethyl-silyl)-5-fluorouracil, and the like); and phosphines (e.g., bis(trimethylsilyl)aminodimethylphosphine, diphenyl(trimethylsilyl-methyl)phosphine, and the like).

The organosilicon products can also serve as starting materials or intermediates for the synthesis of coatings, adhesives, sealants, pharmaceuticals, insecticides, chemical reagents, and other compounds.

In some embodiments, the methods of the present invention for producing organosilicon products comprise combining a silicon-containing reagent, a carbene precursor, and a heme protein, homolog thereof, variant thereof, or fragment thereof as described herein under conditions sufficient to form an organosilicon product.

In some embodiments, the organosilicon product is a compound according to formula III:

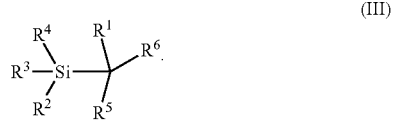

(III)

For compounds of Formula III, $R^1$, $R^2$, $R^3$, and $R^4$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, hydroxy, alkoxy, $SR^7$, $N(R^8)_2$, $B(R^9)_2$, $Si(R^9)_3$, $P(R^9)_3$, $C(O)OR^7$, $C(O)SR^7$, $C(O)N(R^7)_2$, $C(O)R^7$, $C(O)ON(R^7)_2$ and $C(O)NR^7OR^8$. $R^5$ and $R^6$ are independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, optionally substituted 6- to 10-membered heterocyclyl, cyano, halo, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR7)_2$. Each $R^7$, $R^8$, and $R^9$ is independently selected from the group consisting of H, optionally substituted $C_{1-18}$ alkyl, $C_{2-18}$ alkenyl, $C_{2-18}$ alkynyl, optionally substituted $C_{6-10}$ aryl, optionally substituted 6- to 10-membered heteroaryl, and optionally substituted 6- to 10-membered heterocyclyl.

In some embodiments, $R^1$, $R^2$, $R^3$, and $R^4$ in compounds of Formula III are independently selected from the group consisting of H, optionally substituted $C_{1-18}$ alkyl, optionally substituted $C_{2-18}$ alkenyl, optionally substituted $C_{2-18}$ alkynyl, optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl; provided that at least one of $R^2$, $R^3$, and $R^4$ is other than H; and $R^5$ and $R^6$ are independently selected from the group consisting of H, optionally substituted $C_{1-18}$ alkyl, optionally substituted $C_{1-18}$ haloalkyl, optionally substituted $C_{2-18}$ alkenyl, optionally substituted $C_{2-18}$ alkynyl, optionally substituted $C_{6-10}$ aryl, optionally substituted 6- to 10-membered heteroaryl, optionally substituted 6- to 10-membered heterocyclyl, cyano, halo, $N(R^8)_2$, $B(R^9)_2$, $Si(R^9)_3$, $P(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$. In some such embodiments, each $R^7$, $R^8$, and $R^9$ is independently selected from the group consisting of H and optionally substituted $C_{1-6}$ alkyl.

In some embodiments, $R^1$ is H in compounds of Formula III; $R^2$, $R^3$, and $R^4$ are independently selected from the group consisting of H, optionally substituted $C_{1-18}$ alkyl, optionally substituted $C_{2-18}$ alkenyl, optionally substituted $C_{2-18}$ alkynyl, optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl; provided that at least one of $R^2$, $R^3$, and $R^4$ is other than H; and $R^5$ and $R^6$ are independently selected from the group consisting of H, optionally substituted $C_{1-18}$ alkyl, optionally substituted $C_{1-18}$ haloalkyl, optionally substituted $C_{2-18}$ alkenyl, optionally substituted $C_{2-18}$ alkynyl, optionally substituted $C_{6-10}$ aryl, optionally substituted 6- to 10-membered heteroaryl, optionally substituted 6- to 10-membered heterocyclyl, cyano, halo, $N(R^8)_2$, $B(R^9)_2$, $Si(R^9)_3$, $P(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$. In some such embodiments, each $R^7$, $R^8$, and $R^9$ is independently selected from the group consisting of H and optionally substituted $C_{1-6}$ alkyl.

In some embodiments, $R^2$ is selected from the group consisting of optionally substituted $C_{1-18}$ alkyl, optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl. In some embodiments, $R^3$ and $R^4$ are $C_{1-6}$ alkyl. In some embodiments, $R^5$ is $C(O)OR^7$. In some embodiments, $R^6$ is selected from the group consisting of optionally substituted $C_{1-18}$ alkyl, optionally substituted $C_{1-18}$ haloalkyl, and optionally substituted $C_{2-18}$ alkenyl.

In general, the silicon-containing reagents useful in the methods of the invention have the structure according to Formula I:

wherein $R^1$, $R^2$, $R^3$, and $R^4$ are as described above for compounds of Formula III.

In some embodiments, $R^1$, $R^2$, $R^3$, and $R^4$ are independently selected from the group consisting of H, optionally substituted $C_{1-18}$ alkyl, optionally substituted $C_{2-18}$ alkenyl, optionally substituted $C_{2-18}$ alkynyl, optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl.

In some embodiments, $R^1$ is H; and $R^2$, $R^3$, and $R^4$ are independently selected from the group consisting of H, optionally substituted $C_{1-18}$ alkyl, optionally substituted $C_{2-18}$ alkenyl, optionally substituted $C_{2-18}$ alkynyl, optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl; provided that at least one of $R^2$, $R^3$, and $R^4$ is other than H.

In some embodiments, $R^1$ is selected from the group consisting of $B(R^9)_2$ and $Si(R^9)_3$; and $R^2$, $R^3$, and $R^4$ are independently selected from the group consisting of H, optionally substituted $C_{1-18}$ alkyl, optionally substituted $C_{2-18}$ alkenyl, optionally substituted $C_{2-18}$ alkynyl, optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl; provided that at least one of $R^2$, $R^3$, and $R^4$ is other than H.

In some embodiments, $R^2$, $R^3$, and $R^4$ are independently selected from the group consisting of H, optionally substituted $C_{1-18}$ alkyl, optionally substituted $C_{2-18}$ alkenyl, and optionally substituted $C_{2-18}$ alkynyl. In some embodiments, $R^2$, $R^3$, and $R^4$ are independently selected from the group consisting of optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl.

In some embodiments, $R^2$ is selected from the group consisting of optionally substituted $C_{1-18}$ alkyl, optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl. In some embodiments, $R^3$ and $R^4$ are $C_{1-6}$ alkyl. One or both of $R^3$ and $R^4$ can be for, example, methyl, ethyl, n-propyl, isopropyl, n-butyl, or t-butyl. In some embodiments, $R^3$ and $R^4$ are $C_{1-4}$ alkyl. In some embodiments, $R^3$ and $R^4$ are methyl.

In some embodiments, $R^2$ is selected from the group consisting of optionally substituted $C_{1-18}$ alkyl, optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl; and $R^3$ and $R^4$ are independently selected $C_{1-6}$ alkyl.

In some embodiments, $R^2$ is selected from the group consisting of optionally substituted $C_{1-18}$ alkyl, optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl; and $R^3$ and $R^4$ are methyl. In some embodiments, $R^2$ is selected from the group consisting of optionally substituted $C_{6-10}$ aryl, optionally substituted $C_{6-10}$ aryl-$C_{1-6}$ alkyl, optionally substituted 6- to 10-membered heteroaryl, and optionally substituted 6- to 10-membered heterocyclyl; and $R^3$ and $R^4$ are methyl. In some embodiments, $R^2$ is optionally substituted phenyl; and $R^3$ and $R^4$ are independently selected $C_{1-6}$ alkyl. In some embodiments, $R^2$ is optionally substituted phenyl; and $R^3$ and $R^4$ are methyl.

In some embodiments, $R^2$ is phenyl, which is optionally substituted with alkyl, alkenyl, alkynyl, halo, hydroxy, amino, alkylamino, alkoxy, haloalkyl, carboxy, alkyl carboxylate, amido, nitro, oxo, or cyano. In some embodiments, $R^2$ is phenyl, which is optionally substituted with alkyl, alkenyl, alkynyl, haloalkyl, halo, hydroxy, amino, alkylamino, alkoxy, haloalkyl, carboxy, alkyl carboxylate, amido, nitro, oxo, or cyano.

In some embodiments, the silicon-containing reagent has a structure according to Formula Ia:

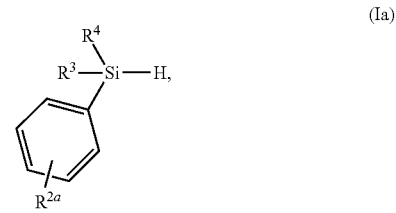

wherein $R^{2a}$ is selected from the group consisting of H, $C_{1-6}$ alkyl, $C_{2-6}$ alkenyl, $C_{2-6}$ alkynyl, hydroxy, $C_{1-6}$ alkoxy, halo, $C_{1-6}$haloalkyl, $C_{1-4}$ alkyl carboxylate, amino, and $C_{3-6}$ alkylamino.

In some embodiments, the silicon-containing reagent has a structure according to Formula Ib:

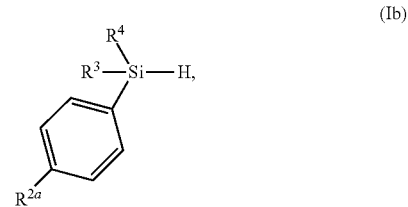

wherein $R^{2a}$ is selected from the group consisting of H, $C_{1-6}$ alkyl, $C_{2-6}$ alkenyl, $C_{2-6}$ alkynyl, hydroxy, $C_{1-6}$ alkoxy, halo, $C_{1-6}$ haloalkyl, $C_{1-4}$ alkyl carboxylate, amino, and $C_{3-6}$ alkylamino.

In some embodiments, the silicon-containing reagent has a structure according to Formula I, wherein $R^2$ is selected from the group consisting of benzyl, naphthyl, 3,4-dihydro-2H-pyran-2-yl, benzofuran-2-yl, and benzo[b]thiophen-2-yl.

A number of carbene precusors can be used in the methods and reaction mixtures of the invention including, but not limited to, amines, azides, hydrazines, hydrazones, epoxides, diazirenes, and diazo reagents. In some embodiments, the carbene precursor is an epoxide (i.e., a compound containing an epoxide moiety). The term "epoxide moiety" refers to a three-membered heterocycle having two carbon atoms and one oxygen atom connected by single bonds. In some embodiments, the carbene precursor is a diazirene (i.e., a compound containing a diazirine moiety). The term "diazirine moiety" refers to a three-membered heterocycle having one carbon atom and two nitrogen atoms, wherein the nitrogen atoms are connected via a double bond. Diazirenes are chemically inert, small hydrophobic carbene precursors described, for example, in US 2009/0211893, by Turro (*J. Am. Chem. Soc.* 1987, 109, 2101-2107), and by Brunner (*J. Biol. Chem.* 1980, 255, 3313-3318), which are incorporated herein by reference in their entirety.

In some embodiments, the carbene precursor is a diazo reagent. In some embodiments, the diazo reagent has a structure according to Formula II:

wherein $R^5$ and $R^6$, as well as $R^7$, $R^8$, and $R^9$ within $R^5$ and $R^6$, are as described above for compounds of Formula III.

In some embodiments, $R^5$ and $R^6$ are independently selected from the group consisting of H, optionally substituted $C_{1-18}$ alkyl, optionally substituted $C_{1-18}$ haloalkyl, optionally substituted $C_{2-18}$ alkenyl, optionally substituted $C_{2-18}$ alkynyl, optionally substituted $C_{6-10}$ aryl, optionally substituted 6- to 10-membered heteroaryl, optionally substituted 6- to 10-membered heterocyclyl, cyano, halo, $N(R^8)_2$, $B(R^9)_2$, $Si(R^9)_3$, $C(O)OR^7$, $C(O)SR^7$, $C(O)N(R^7)_2$, $C(O)R^7$, $C(O)ON(R^7)_2$, $C(O)NR^7OR^8$, $C(O)C(O)OR^7$, and $P(O)(OR^7)_2$. Each $R^7$, $R^8$, and $R^9$ is independently selected from the group consisting of H and optionally substituted $C_{1-6}$ alkyl. One, two, or three of $R^7$, $R^8$, and $R^9$ can be, for example, methyl, ethyl, n-propyl, isopropyl, n-butyl, or t-butyl. In some embodiments, one, two, or three of $R^7$, $R^8$, and $R^9$ are H.

In some embodiments, $R^5$ and $R^6$ are independently selected from the group consisting of H, optionally substituted $C_{1-18}$ alkyl, optionally substituted C haloalkyl, optionally substituted $C_{2-18}$ alkenyl, optionally substituted $C_{2-18}$ alkynyl, optionally substituted $C_{6-10}$ aryl, optionally substituted 6- to 10-membered heteroaryl, optionally substituted 6- to 10-membered heterocyclyl, cyano, and halo. In some embodiments, $R^5$ and $R^6$ are independently selected from the group consisting of $N(R^8)_2$, $B(R^9)_2$, $Si(R^9)_3$, and $P(O)(OR^7)_2$. In some embodiments, $R^5$ and $R^6$ are independently selected from the group consisting of $C(O)OR^7$, $C(O)SR^7$, $C(O)N(R^7)_2$, $C(O)R^7$, $C(O)ON(R^7)_2$, $C(O)NR^7R^8$, and $C(O)C(O)OR^7$.

In some embodiments, $R^5$ is $C(O)OR^7$. In some embodiments, $R^6$ is selected from the group consisting of optionally substituted $C_{1-18}$ alkyl, optionally substituted $C_{6-10}$ aryl, optionally substituted C haloalkyl, and optionally substituted $C_{2-18}$ alkenyl.

In some embodiments, $R^5$ is $C(O)OR^7$ and $R^7$ is optionally substituted $C_{1-6}$ alkyl. In some embodiments, $R^5$ is $C(O)OR^7$ and $R^7$ is selected from the group consisting of methyl and ethyl. In some embodiments, $R^5$ is $C(O)OR^7$; $R^7$ is selected from the group consisting of methyl and ethyl; and $R^6$ is selected from the group consisting of $C_{1-12}$ alkyl, $C_{6-10}$ aryl, $C_{1-12}$ haloalkyl, and $C_{2-12}$ alkenyl. In some embodiments, $R^5$ is $C(O)OR^7$ and $R^7$ is ethyl. In some embodiments, $R^5$ is $C(O)OR^7$; $R^7$ is ethyl; and $R^6$ is selected from the group consisting of methyl, ethyl, phenyl, trifluoromethyl, and allyl (i.e., $CH_3$—CH=CH—).

In some embodiments, the diazo reagent is selected from an α-diazoester, an α-diazoamide, an α-diazonitrile, an α-diazoketone, an α-diazoaldehyde, and an α-diazosilane. In some embodiments, the diazo reagent has a formula selected from:

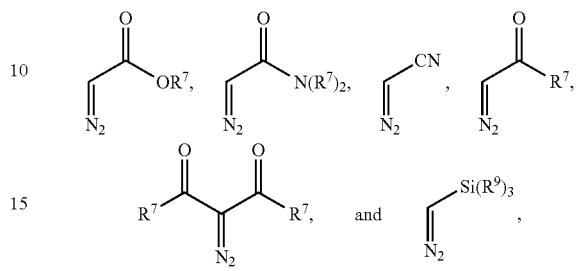

wherein each $R^7$ and $R^9$ is independently selected from H, optionally substituted $C_{1-12}$ alkyl, optionally substituted $C_{2-12}$ alkenyl, and optionally substituted $C_{6-10}$ aryl.

Diazo reagents can be formed from a number of starting materials using procedures that are known to those of skill in the art. Ketones (including 1,3-diketones), esters (including β-ketones), acyl chlorides, and carboxylic acids can be converted to diazo reagents employing diazo transfer conditions with a suitable transfer reagent (e.g., aromatic and aliphatic sulfonyl azides, such as toluenesulfonyl azide, 4-carboxyphenylsulfonyl azide, 2-naphthalenesulfonyl azide, methylsulfonyl azide, and the like) and a suitable base (e.g., triethylamine, triisopropylamine, diazobicyclo[2.2.2]octane, 1,8-diazabicyclo[5.4.0]undec-7-ene, and the like) as described, for example, in U.S. Pat. No. 5,191,069 and by Davies (*J. Am. Chem. Soc.* 1993, 115, 9468-9479), which are incorporated herein by reference in there entirety. The preparation of diazo compounds from azide and hydrazone precursors is described, for example, in U.S. Pat. Nos. 8,350,014 and 8,530,212, which are incorporated herein by reference in there entirety. Alkylnitrite reagents (e.g., (3-methylbutyl)nitrite) can be used to convert α-aminoesters to the corresponding diazocompounds in non-aqueous media as described, for example, by Takamura (*Tetrahedron*, 1975, 31: 227), which is incorporated herein by reference in its entirety. Alternatively, a diazo compound can be formed from an aliphatic amine, an aniline or other arylamine, or a hydrazine using a nitrosating agent (e.g., sodium nitrite) and an acid (e.g., p-toluenesulfonic acid) as described, for example, by Zollinger (*Diazo Chemistry I and II*, VCH Weinheim, 1994) and in US 2005/0266579, which are incorporated herein by reference in their entirety.

In some embodiments, the invention provides methods and reaction mixtures for producing an organosilicon product wherein the carbene precursor is an amine. In some embodiments, the amine is converted to a diazo reagent by contacting the amine with a nitrosating agent under conditions sufficient to form the diazo reagent. In some embodiments, the nitrosating agent is selected from the group consisting of sodium nitrite, potassium nitrite, lithium nitrite, calcium nitrite, magnesium nitrite, ethyl nitrite, n-butyl nitrite, and (3-methylbutyl)nitrite. In the some embodiments, the amine is contacted with the nitrosating agent in the presence of an acid. Examples of suitable acids include, but are not limited to, sulfonic acids (e.g., p-toluenesulfonic acid, methanesulfonic acid, and the like), phosphoric acid, nitric acid, sulfuric acid, and hydrochloric acid. In some embodiments, the nitrosating agent is sodium nitrite. In some embodiments, the nitrosating agent is sodium nitrite and the acid is p-toluenesulfonic acid. In some embodiments, the nitrosating agent is sodium nitrite, the acid is p-toluenesulfonic acid, and the amine is selected from the group consisting of an alkylamine, an arylamine, an α-aminoketone, an α-aminoester, and an α-aminoamide. In some embodiments, the amine is contacted with the nitrosating reagent (and the acid, when used) in a suitable organic solvent (e.g., acetonitrile, N,N-dimethylformamide, dimethylsulfoxide, and the like) for a time sufficient to form the diazo reagent prior to combination with the silicon-containing reagent and the heme protein used for forming the organosilicon product. The diazo reagent in the organic solvent can then be combined with a mixture containing the silicon-containing reagent and the heme protein. In some embodiments, the mixture containing the silicon-containing reagent and the heme protein is an aqueous mixture containing a suitable buffer as described below. Alternatively, the amine can be converted to the diazo reagent in situ, by combining the amine, the nitrosating agent, and the acid (when used) directly with the the silicon-containing reagent and the heme protein.

C. Reaction Conditions

The methods of the invention include forming reaction mixtures that comprise a silicon-containing reagent, a carbene precursor, and a heme protein, fragment thereof, homolog thereof, or variant thereof as described above.

The heme proteins, fragments thereof, homologs thereof, or variants thereof can be, for example, purified prior to addition to a reaction mixture or secreted by a cell present in the reaction mixture. The reaction mixture can contain a cell lysate including the heme protein, fragment thereof, homolog thereof, or variant thereof, as well as other proteins and other cellular materials. Alternatively, a heme protein, fragment thereof, homolog thereof, or variant thereof can catalyze the reaction within a cell expressing the heme protein, fragment thereof, homolog thereof, or variant thereof. Any suitable amount of heme protein, fragment thereof, homolog thereof, or variant thereof can be used in the methods of the invention. In general, silicon-hydrogen carbene insertion reaction mixtures contain from about 0.01 mol % to about 10 mol % heme protein with respect to the carbene precursor (e.g., diazo reagent) and/or silicon-containing reagent. The reaction mixtures can contain, for example, from about 0.01 mol % to about 0.1 mol % heme protein, or from about 0.1 mol % to about 1 mol % heme protein, or from about 1 mol % to about 10 mol % heme protein. The reaction mixtures can contain from about 0.05 mol % to about 5 mol % heme protein, or from about 0.05 mol % to about 0.5 mol % heme protein. The reaction mixtures can contain about 0.1, 0.2, 0.3, 0.4, 0.5, 0.6, 0.7, 0.8, 0.9, or about 1 mol % heme protein.

One of skill in the art will appreciate that depending on the structure of the carbene precursor and/or silicon-containing reagent, silicon-hydrogen carbene insertion reaction mixtures of the present invention can comprise a carbene precursor, a silicon-containing reagent, and an isolated heme group. The heme group can comprise a porphyrin molecule and an iron cofactor. In particular embodiments, the porphyrin molecule contains a non-native cofactor (i.e., a metal other than iron), non-limiting examples of which include cobalt, rhodium, copper ruthenium, iridium, and manganese. The cofactor can be any metal, as long as it catalyzes carbon-silicon bond formation. The heme group can catalyze carbon-silicon bond formation in vitro, or can be present in a cell and the carbon-silicon bond formation can occur in vivo. For in vivo reactions, any suitable host cell described herein can be used. The reaction mixtures can contain, for example, from about 0.01 mol % to about 0.1 mol % heme, or from about 0.1 mol % to about 1 mol % heme, or from about 1 mol % to about 10 mol % heme. The reaction mixtures can contain from about 0.05 mol % to about 5 mol % heme, or from about 0.05 mol % to about 0.5 mol % heme. The reaction mixtures can contain about 0.1, 0.2, 0.3, 0.4, 0.5, 0.6, 0.7, 0.8, 0.9, or about 1 mol % heme.

The concentration of silicon-containing reagent and carbene precursor (e.g., diazo reagent) are typically in the range of from about 100 μM to about 1 M. The concentration can be, for example, from about 100 μM to about 1 mM, or about from 1 mM to about 100 mM, or from about 100 mM to about 500 mM, or from about 500 mM to 1 M. The concentration can be from about 500 μM to about 500 mM, 500 μM to about 50 mM, or from about 1 mM to about 50 mM, or from about 15 mM to about 45 mM, or from about 15 mM to about 30 mM. The concentration of silicon-containing reagent or carbene precursor can be, for example, about 100, 200, 300, 400, 500, 600, 700, 800, or 900 μM. The concentration of silicon-containing reagent or carbene precursor can be about 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, or 500 mM.

Reaction mixtures can contain additional reagents. As non-limiting examples, the reaction mixtures can contain buffers (e.g., M9-N buffer, 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, isopropanol, glycerol, tetrahydrofuran, acetone, acetonitrile, and acetic acid), salts (e.g., NaCl, KCl, $CaCl_2$, and salts of $Mn^{2+}$ and $Mg^{2+}$), denaturants (e.g., urea and guandinium hydrochloride), detergents (e.g., sodium dodecylsulfate and Triton-X 100), chelators (e.g., ethylene glycol-bis(2-aminoethylether)-N,N,N',N'-tetraacetic acid (EGTA), 2-({2-[Bis(carboxymethyl)amino]ethyl} (carboxymethyl)amino)acetic acid (EDTA), and 1,2-bis(o-aminophenoxy)ethane-N,N,N',N'-tetraacetic acid (BAPTA)), sugars (e.g., glucose, sucrose, and the like), and reducing agents (e.g., sodium dithionite, NADPH, dithiothreitol (DTT), β-mercaptoethanol (BME), and tris(2-carboxyethyl)phosphine (TCEP)). Buffers, cosolvents, salts, denaturants, detergents, chelators, sugars, and reducing agents can be used at any suitable concentration, which can be readily determined by one of skill in the art. In general, buffers, cosolvents, salts, denaturants, detergents, chelators, sugars, and reducing agents, if present, are included in reaction mixtures at concentrations ranging from about 1 μM to about 1 M. For example, a buffer, a cosolvent, a salt, a denaturant, a detergent, a chelator, a sugar, or a reducing agent can be included in a reaction mixture at a concentration of about 1 μM, or about 10 μM, or about 100 μM, or about 1 mM, or about 10 mM, or about 25 mM, or about 50 mM, or about 100 mM, or about 250 mM, or about 500 mM, or about 1 M. In some embodiments, a reducing agent is used in a sub-stoichiometric amount with respect to the olefin substrate and the diazo reagent. Cosolvents, in particular, can be included in the reaction mixtures in amounts ranging from about 1% v/v to about 75% v/v, or higher. A cosolvent can be included in the reaction mixture, for example, in an amount of about 5, 10, 20, 30, 40, or 50% (v/v).

Reactions are conducted under conditions sufficient to catalyze the formation of an organosilicon product. The reactions can be conducted at any suitable temperature. In general, the reactions are conducted at a temperature of from about 4° C. to about 40° C. The reactions can be conducted, for example, at about 25° C. or about 37° C. The heme proteins or cells expressing or containing the heme proteins can be heat treated. In some embodiments, heat treatment occurs at a temperature of about 75° C. The reactions can be conducted at any suitable pH. In general, the reactions are conducted at a pH of from about 6 to about 10. The reactions can be conducted, for example, at a pH of from about 6.5 to about 9 (e.g., about 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0). The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. The reactions can be conducted for about 1 to 4 hours (e.g., 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, or 4 hours). Reactions can be conducted under aerobic conditions or anaerobic conditions. Reactions can be conducted under an inert atmosphere, such as a nitrogen atmosphere or argon atmosphere. In some embodiments, a solvent is added to the reaction mixture. In some embodiments, the solvent forms a second phase, and the carbene insertion into silicon-hydrogen bonds occurs in the aqueous phase. In some embodiments, the heme protein, fragment thereof, variant thereof, or homolog thereof, is located in the aqueous layer whereas the substrates and/or products occur in an organic layer. Other reaction conditions may be employed in the methods of the invention, depending on the identity of a particular heme protein, silicon-containing reagent, or carbene precursor (e.g., diazo reagent).

Reactions can be conducted in vivo with intact cells expressing a heme enzyme of the invention. The in vivo reactions can be conducted with any of the host cells used for expression of the heme enzymes, as described herein. A suspension of cells can be formed in a suitable medium supplemented with nutrients (such as mineral micronutrients, glucose and other fuel sources, and the like). Organosilicon product yields from reactions in vivo can be controlled, in part, by controlling the cell density in the reaction mixtures. Cellular suspensions exhibiting optical densities ranging from about 0.1 to about 50 at 600 nm can be used for silicon-hydrogen carbene insertion reactions. Other densities can be useful, depending on the cell type, specific heme proteins, or other factors.

The methods of the invention can be assessed in terms of the diastereoselectivity and/or enantioselectivity of carbene insertion into silicon-hydrogen bonds—that is, the extent to which the reaction produces a particular isomer, whether a diastereomer or enantiomer. A perfectly selective reaction produces a single isomer, such that the isomer constitutes 100% of the product. As another non-limiting example, a reaction producing a particular enantiomer constituting 90% of the total product can be said to be 90% enantioselective. A reaction producing a particular diastereomer constituting 30% of the total product, meanwhile, can be said to be 30% diastereoselective.

In general, the methods of the invention include reactions that are from about 1% to about 99% diastereoselective. The reactions are from about 1% to about 99% enantioselective. The reaction can be, for example, from about 10% to about 90% diastereoselective, or from about 20% to about 80% diastereoselective, or from about 40% to about 60% diastereoselective, or from about 1% to about 25% diastereoselective, or from about 25% to about 50% diastereoselective, or from about 50% to about 75% diastereoselective. The reaction can be about 10%, 15%, 20%, 25%, 30%, 35%, 40%, 45%, 50%, 55%, 60%, 65%, 70%, 75%, 80%, 85%, 90%, or about 95% diastereoselective. The reaction can be from about 10% to about 90% enantioselective, from about 20% to about 80% enantioselective, or from about 40% to about 60% enantioselective, or from about 1% to about 25% enantioselective, or from about 25% to about 50% enantioselective, or from about 50% to about 75% enantioselective. The reaction can be about 10%, 15%, 20%, 25%, 30%, 35%, 40%, 45%, 50%, 55%, 60%, 65%, 70%, 75%, 80%, 85%, 90%, or about 95% enantioselective. Accordingly some embodiments of the invention provide methods wherein the reaction is at least 30% to at least 90% diastereoselective. In some embodiments, the reaction is at least 30% to at least 90% enantioselective. Preferably, the reaction is at least 80% (e.g., at least about 80%, 81%, 82%, 83%, 84%, 85%, 86%, 87%, 88%, 89%, 90%, 91%, 92%, 93%, 94%, 95%, 96%, 97%, 98%, 99%, or 100%) enantioselective. More preferably, the reaction is at least 90% (e.g., at least about 90%, 91%, 92%, 93%, 94%, 95%, 96%, 97%, 98%, 99%, or 100%) enantioselective.

IV. Examples

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

EXAMPLE 1

Enzymatic Carbon-Silicon Bond Formation to Afford Organosilicon Compounds Using Cytochrome P450 Proteins and Other Heme Proteins This example shows the production of organosilicon compounds using various heme proteins, including cytochrome P450 proteins.

P450 Expression and Purification

One liter Hyperbroth (0.1 mg/mL ampicillin) was inoculated with an overnight culture (25 mL LB, 0.1 mg/mL ampicillin) of recombinant *E. coli* BL21 cells harboring a pCWori or pET22 plasmid encoding cytochrome P450 variants under the control of the tac or T7 promoter. The cultures were shaken at 200 rpm at 37° C. for roughly 3.5 hours, or until an optical of density of 1.2-1.8 was reached. The temperature was reduced to 20° C. and the shake rate was reduced to 130-150 rpm for 20 minutes, then the cultures were induced by adding isopropyl β-D-1-thiogalactopyranoside (IPTG) and aminolevulinic acid to a final concentration of 0.25 mM and 0.5 mM, respectively. The cultures were allowed to continue for another 20 hours at this temperature and shake rate. Cell were harvested by centrifugation (4° C., 15 minutes, 3,000×g), and the cell pellet was stored at −20° C. or below for at least 2 hours. For the purification of 6×His tagged cytochrome P450s, the thawed cell pellet was resuspended in Ni-NTA buffer A (25 mM Tris.HCl, 200 mM NaCl, 25 mM imidazole, pH 8.0, 4 mL/gcw) and lysed by sonication (2×1 min, output control 5, 50% duty cycle). The lysate was centrifuged at 27,000×g for 20 minutes at 4° C. to remove cell debris. The collected supernatant was first subjected to a Ni-NTA chromatography step using a Ni Sepharose column (HisTrap-HP, GE healthcare, Piscataway, N.J.). The cytochrome P450 was eluted from the Ni Sepharose column using 25 mM Tris.HCl, 200 mM NaCl, 300 mM imidazole, pH 8.0. Ni-purified protein was buffer exchanged into 0.1 M phosphate buffer (pH 8.0) using a 30 kDa molecular weight cut-off centrifugal filter. Protein concentrations were determined by CO-assay. For storage, proteins were portioned into 300 µL aliquots and stored at −80° C.

Small-Scale Carbon-Silicon Bond Forming Reactions In Vitro and In Vivo Under Anaerobic Conditions The in vitro and in vivo carbon-silicon bond forming reaction procedures catalyzed by cytochrome P450s and other heme proteins were identical to those described in Example 2 for Rma cyt c. The results are presented FIG. 1 and demonstrate that a variety of heme proteins (myoglobin, P450, globin and cytochrome c) functioned as carbon-silicon bond forming catalysts to give product of Formula III.

Small-Scale Carbon-Silicon Bond Forming Reactions Under Aerobic Conditions

The procedures for carbon-silicon bond formation under aerobic conditions were similar to those described for anaerobic conditions, except that the reactions were carried out under air.

EXAMPLE 2

Enzymatic Carbon-Silicon Bond Formation to Afford Organosilicon Compounds Using Rma Cyt c Variants In Vitro and In Vivo This example shows the use of cytochrome c protein from *Rhodothermus marinus* (Rma cyt c) to catalyze the formation of organosilicon compounds.

Cytochrome c Expression

One liter Hyperbroth (100 µg/mL ampicillin, 20 µg/mL chloramphenicol) was inoculated with an overnight culture of 20 mL LB (100 µg/mL ampicillin, 20 µg/mL chloramphenicol). The overnight culture contained recombinant *E. coli* BL21-DE3 cells harboring a pET22 plasmid and pEC86 plasmid (Arslan et al. *Biochem. Biophys. Res. Commun.* 251, 744-747 (1998)) encoding the cytochrome c variant under the control of the T7 promoter, and the cytochrome c maturation (ccm) operon under the control of a tet promoter, respectively. The cultures were shaken at 200 rpm at 37° C. for approximately 2 hours or until an optical of density of 0.6-0.9 was reached. The flask containing the cells was placed on ice for 30 minutes. The incubator temperature was reduced to 20° C., maintaining the 200 rpm shake rate. Cultures were induced by adding IPTG and aminolevulinic acid to a final concentration of 20 µM and 200 µM, respectively. The cultures were allowed to continue for another 20-24 hours at this temperature and shake rate. Cells were harvested by centrifugation (4° C., 15 minutes, 3,000×g) to produce a cell pellet.

Preparation of Whole Cell and Heat-Treated Lysate Catalysts

To prepare whole cells for catalysis, the cell pellet prepared in the previous paragraph was resuspended in M9-N minimal media (M9 media without ammonium chloride) to an optical density (OD600) of 60. To prepare heat-treated lysate for catalysis, whole cells in M9-N minimal media at OD600=15 were placed in a water bath at 75° C. for 10 minutes. After the time at 75° C., the sample was centrifuged to remove the precipitate (4° C., 10 minutes, 4,000×g). The supernatant was collected and used as the heat-treated lysate catalyst, while the pellet was discarded.

Purification of Rma Cyt c

To prepare purified proteins, the cell pellet prepared as described above was stored at −20° C. or below overnight. For the purification of 6×His tagged cytochrome c proteins, the thawed cell pellet was resuspended in Ni-NTA buffer A (25 mM Tris.HCl, 200 mM NaCl, 25 mM imidazole, pH 8.0, 4 mL/gcw) and lysed by sonication (2 minutes, 2-second pulse, 2 seconds off, 50% amplitude on a Q500 Qsonica sonicator). After sonication, the sample was centrifuged at 27,000×g for 10 minutes at 4° C. to remove cell debris. The sample was then placed in a water bath at 75° C. for 10 minutes, and centrifuged at 27,000×g for 10 minutes at 4° C. to remove cell debris. The collected supernatant was purified using an AKTA purifier 10 FPLC with a Ni Sepharose column (HisTrap-HP, GE healthcare, Piscataway, N.J.). The cytochrome c was eluted from the Ni Sepharose column using 25 mM Tris.HCl, 200 mM NaCl, 300 mM imidazole, pH 8.0. The Ni-purified protein was buffer exchanged into 0.1 M phosphate buffer (pH 8.0) using a 10 kDa molecular weight cut-off centrifugal filter, then dialyzed overnight at 4° C. in 20 mM phosphate buffer (pH 8.0) using a 3.5 kDa molecular weight cut-off dialysis bag. Protein concentrations were determined by BCA assay, using BSA to create the standard curve. For storage, proteins were portioned into 300 µL aliquots and stored at −80° C.

Figure 2:
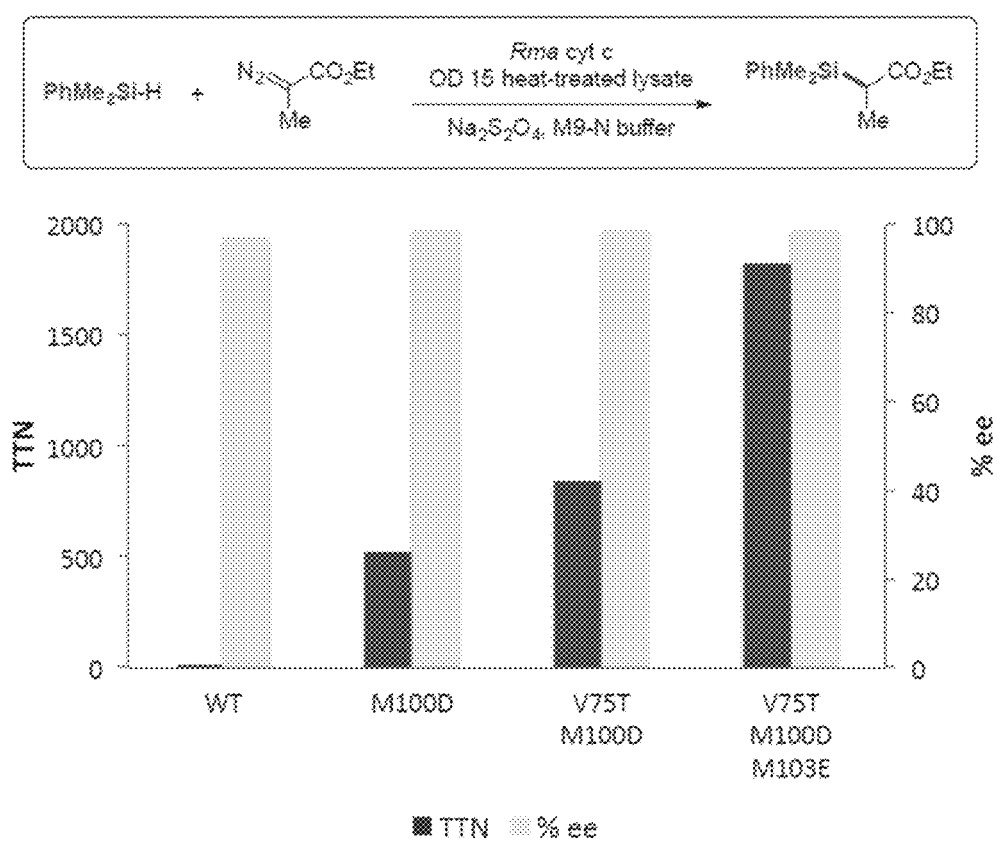
FIG. 2 shows total turnover number (TTN) and % ee of various Rma cyt c variants in catalysis of production of organosilicon compounds.

Small-Scale Carbon-Silicon Bond Forming Reactions in Heat-Treated Lysate Under Anaerobic Conditions Small-scale (400 µL) reactions were carried out in 2 mL glass crimp vials (Agilent Technologies, San Diego, Calif.). Heat-treated lysate (340 µL) was added to an unsealed crimp vial before crimp sealing with a silicone septum. The headspace of the vial was flushed with argon for 10 minutes (no bubbling). A solution of sodium dithionite (40 µL, 100 mM) was added, followed by a solution of silicon-containing reagent of Formula I (10 µL, 400 mM in MeCN; for example, PhMe2SiH) and a solution of diazo reagent of Formula II (10 µL, 400 mM in MeCN; for example, ethyl 2-diazopropanoate or Me-EDA). The reaction vial was left to shake on a plate shaker at 400 rpm for 1.5 hours at room temperature. To quench the reaction, the vial was uncapped and cyclohexane (1 mL) was added, followed by 2-phenylethanol (20 µL, 20 mM in cyclohexane) as an internal standard. The mixture was transferred to a 1.5 mL Eppendorf tube and vortexed and centrifuged (14000×rcf, 5 minutes). The organic layer was analyzed by gas chromatography (GC) and supercritical fluid chromatography (SFC). The results of the small scale reactions are presented in FIG. 2 and demonstrate that Rma cyt c and variants thereof were capable of catalyzing the formation of carbon-silicon bonds to give product of formula III with high turnover number and selectivity. Specifically, the best variant found in the initial screen of Rma cyt c variants comprised the mutations V75T, M100D, and M103E, which catalyzed the desired reaction with greater than 1,800 total turnover number (TTN) and greater than 99% ee.

Small-Scale Whole Cells Catalysis of Carbon-Silicon Bond Formation

Small-scale (400 µL) reactions were carried out in 2 mL glass crimp vials (Agilent Technologies, San Diego, Calif.). Whole cell catalysts (340 µL, OD600=60 in M9-N minimal media) were added to an unsealed crimp vial before crimp sealing with a silicone septum. The headspace of the vial was flushed with argon for 10 minutes (no bubbling). A solution of glucose (40 μL, 250 mM) was added, followed by a solution of silicon reagent of Formula I (10 μL, 400 mM in MeCN; for example, PhMe2SiH) and a solution of diazo reagent of Formula II (10 μL, 400 mM in MeCN; for example, ethyl 2-diazopropanoate or Me-EDA). The reaction vial was left to shake on a plate shaker at 400 rpm for 1.5 hours at room temperature. To quench the reaction, the vial was uncapped and cyclohexane (1 mL) was added, followed by 2-phenylethanol (20 μL, 20 mM in cyclohexane) as an internal standard. The mixture was transferred to a 1.5 mL Eppendorf tube and vortexed and centrifuged (14000×rcf, 5 minutes). The organic layer was analyzed by gas chromatography (GC) and supercritical fluid chromatography (SFC).

Figure 3:
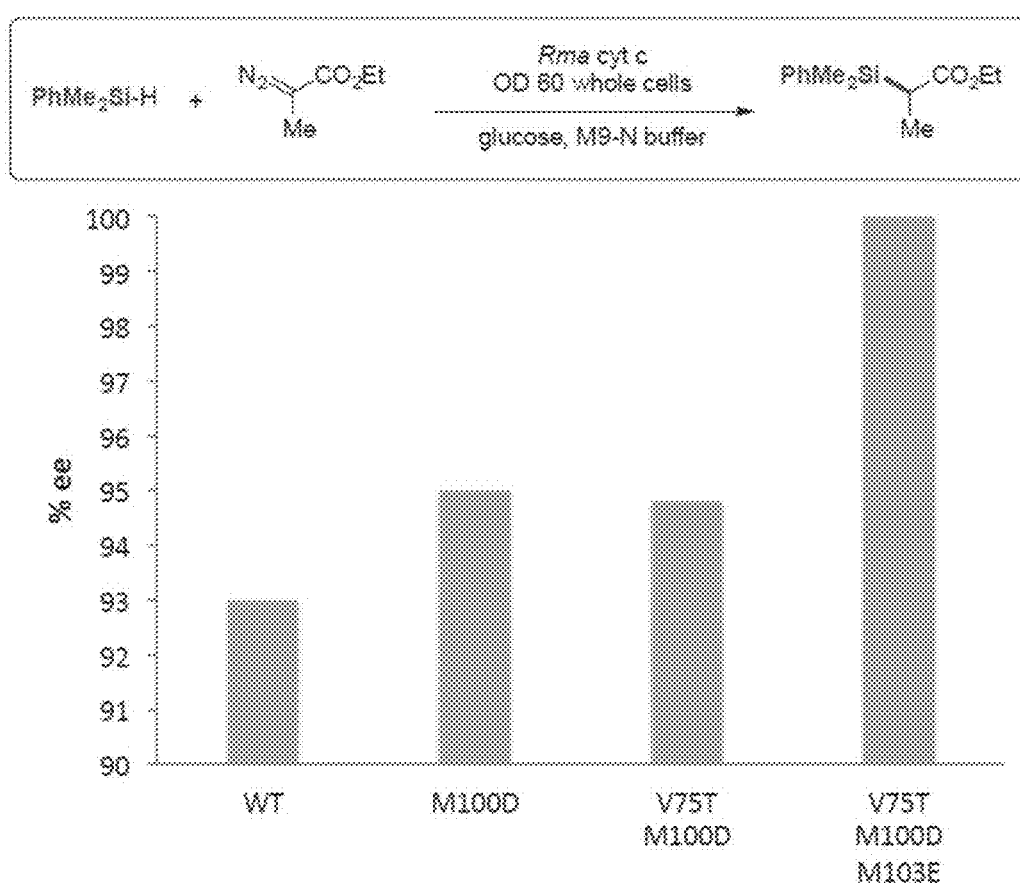
FIG. 3 shows % ee of various Rma cyt c variants in whole-cell catalysis of production of organosilicon compounds.

The results of the small scale reactions are presented in FIG. 3 and demonstrate that Rma cyt c and variants thereof functioned as whole-cell catalysts and promoted the formation of carbon-silicon bonds to give products of Formula III with high selectivity. Specifically, the best variant found in the initial screen of Rma cyt c variants comprised the mutations V75T, M100D and M103E, which provided product of formula III in greater than 99% ee.

EXAMPLE 3

Directed Evolution of Cytochrome c for Carbon-Silicon Bond Formation

This example shows the generation of mutant variants of *Rhodothermus marinus* (Rma) cytochrome c and demonstrates their ability to act as carbon-silicon bond-forming catalysts in vitro and in vivo.

Introduction

Silicon constitutes almost 30% of the mass of the Earth's crust, yet no life form is known to have the ability to forge carbon-silicon bonds (1). Despite the absence of organosilicon compounds in the biological world, synthetic chemistry has enabled the appreciation of the unique and desirable properties that have led to their broad applications in chemistry and materials science (2,3). As a biocompatible carbon isostere, silicon can also be used to optimize and repurpose the pharmaceutical properties of bioactive molecules (4,5).

The natural supply of silicon may be abundant, but sustainable methods for synthesizing organosilicon compounds are not (6-8). Carbon-silicon bond forming methods that introduce silicon motifs to organic molecules enantioselectively rely on multi-step synthetic campaigns to prepare and optimize chiral reagents or catalysts; precious metals are also sometimes needed to achieve the desired activity (9-15). Synthetic methodologies such as carbene insertion into silanes can be rendered enantioselective using chiral transition metal complexes based on rhodium (11,12), iridium (13) and copper (14,15). These catalysts can provide optically pure products, but not without limitations: they require halogenated solvents and sometimes low temperatures to function optimally and have limited turnovers (less than 100). Examples of known catalytic systems are listed in Tables 2-4. α-Alkyl diazo compounds are challenging substrates for intermolecular carbene-transfer chemistry due to their propensity to undergo competing intramolecular β-hydride migration (120,85). As a result, only a subset of catalytic systems shown in Table 2 have been reported to accommodate these substrates, as summarized in Table 3.

TABLE 2

Summary of known catalytic systems for enantioselective carbene insertion into silicon-hydrogen bonds

| Chiral catalytic system | Ref | Reaction condition | Substrate scope | TTN | % ee |
|---|---|---|---|---|---|
| Copper | | | | | |
| A* | (87) | $CH_2Cl_2$, rt, 18 h | 4 | 17 to 25 | 17 to 98 |
| B | (108) | $C_6H_6$, 0° C., 13.5 h | 1 | 8 to 10 | 29 to 78 |
| C* | (86) | $CH_2Cl_2$, −60 to 0° C., 2-12 h | 24 | 3 to 19 | 12 to 99 |
| B | (109) | $CH_2Cl_2$, −40 to 0° C., 48-72 h | 8 | 5 to 9 | 49 to 88 |
| B | (110) | $CH_2Cl_2$, −40 to −10° C. | 9 | 5 to 8 | 40 to 84 |
| Iridium | | | | | |
| D* | (85) | $CH_2Cl_2$, −78 or −30° C., 24 h | 15 | 24 to 50 | 94 to 99 |
| E | (111) | $CH_2Cl_2$, −78° C., 24 h | 7 | 75 to 94 | 72 to 91 |
| Rhodium | | | | | |
| F* | (84) | $CH_2Cl_2$, rt to 40° C., 6-12 h | 34 | 9 to 30 | 77 to 99 |
| G | (112) | $CH_2Cl_2$, −78° C. or rt, 3-12 h | 5 | 8 to 45 | 20 to 63 |
| H | (108) | $C_5H_{12}$, −78 to −75° C., 24 h | 1 | 24 to 70 | 48 to 97 |
| I* | (83) | $CF_3CH_2OH$, −35° C. | 10 | 51 to 97 | 20 to 99 |
| H | (113) | $CH_2Cl_2$, −78° C. then rt, 23 h | 6 | 22 to 54 | 77 to 94 |
| various Rh(II)-carboxylate | (114) (115) | $CH_2Cl_2$, rt or −78° C., 0.5 to 24 h to overnight | 6 | <1 to 23 | 6 to 76 |
| J | (116) | $CH_2Cl_2$, −78° C. to rt, 23 h | 2 | 35 to 40 | 38 to 58 |
| H | (117) | $CH_2Cl_2$, −78° C., 1 to 1.5 h | 4 | 34 to 43 | 35 to 72 |
| H | (118) | $C_5H_{12}$, −78° C., 24 h | 5 | 13 to 19 | 75 to 95 |
| various Rh(II)-carboxylate | (119) | $CH_2Cl_2$, rt or reflux | 1 | 8 to 17 | 6 to 47 |

Figure 4:
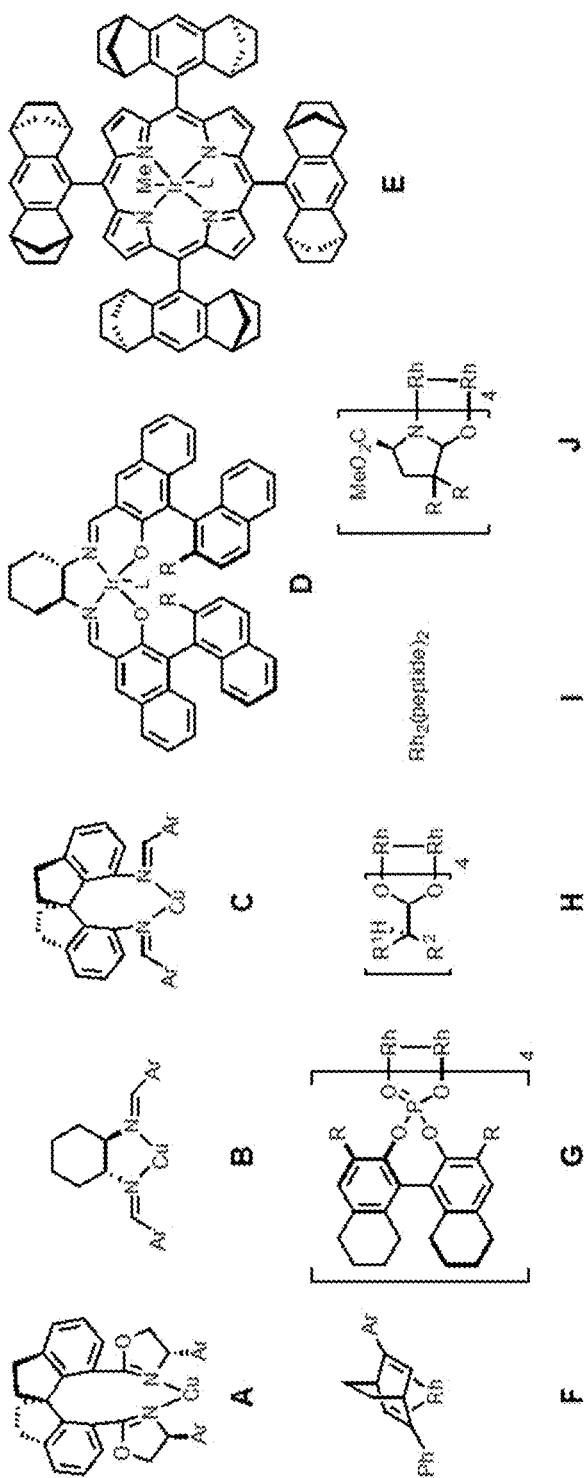
FIG. 4 shows the chemical structures of some known catalytic systems. Labels correspond to those used in Table 2.

Catalytic systems that could afford enantiopure products are denoted with (*). rt = room temperature. Chemical structures of catalysts are shown in FIG. 4.

TABLE 3

Summary of known catalytic systems that can accept α-alkyl diazo compounds as substrates for enantioselective carbene insertion into silicon-hydrogen bonds

| Chiral catalytic system | Ref | Reaction condition | Substrate scope | TTN | % ee |
|---|---|---|---|---|---|
| Copper | | | | | |
| A | (87) | $CH_2Cl_2$, rt, 18 h | 4 | 17 to 25 | 17 to 98 |
| C | (86) | $CH_2Cl_2$, −40° C., 2-12 h | 2 | 3 to 12 | 12 to 35 |
| Iridium | | | | | |
| D | (85) | $CH_2Cl_2$, −78° C., 24 h | 8 | 24 to 44 | 94 to 99 |
| Rhodium | | | | | |
| F | (84) | $CH_2Cl_2$, rt to 40° C., 6-12 h | 2 | 11 to 15 | 70 to 77 |
| I | (83) | $CF_3CH_2OH$, −35° C. | 1 | N/A | 64 |
| H | (113) | $CH_2Cl_2$, −78° C. then rt, 23 h | 5 | 22 to 54 | 77 to 94 |

Chemical structures of chiral catalysts are shown in FIG. 4. rt denotes room temperature.

TABLE 4

Summary of known catalytic systems for reaction between phenyldimethylsilane and Me-EDA via enantioselective carbene insertion into silicon-hydrogen bonds

| Chiral catalytic system | Ref | Reaction condition | TTN | % ee |
|---|---|---|---|---|
| Copper | | | | |
| C | (86) | $CH_2Cl_2$, −40° C., 2-12 h | 12 | 35 |
| Iridium | | | | |
| D | (85) | $CH_2Cl_2$, −78° C., 24 h | 43 | 97 |
| Rhodium | | | | |
| F | (84) | $CH_2Cl_2$, rt to 40° C., 6-12 h | 15 | 77 |

Chemical structures of chiral catalysts are shown in FIG. 4.
rt denotes room temperature.

Because of their ability to accelerate chemical transformations with exquisite specificity and selectivity, enzymes are increasingly sought after complements to or even replacements for chemical synthesis methods (16,17). Biocatalysts that are fully genetically encoded and assembled inside of cells are readily tunable using molecular biology techniques.

They can be produced at low cost from renewable resources in microbial systems and perform catalysis under mild conditions. Although nature does not use enzymes to form carbon-silicon bonds, the protein machineries of living systems are often "promiscuous," that is, capable of catalyzing reactions distinct from their biological functions. Evolution, natural or in the laboratory, can use these promiscuous functions to generate catalytic novelty (18-20). For example, heme proteins can catalyze a variety of non-natural carbene transfer reactions inC1 aqueous media, including N—H and S—H insertions, which can be greatly enhanced and made exquisitely selective by directed evolution (21-23).

Results and Discussion

Figure 5A:
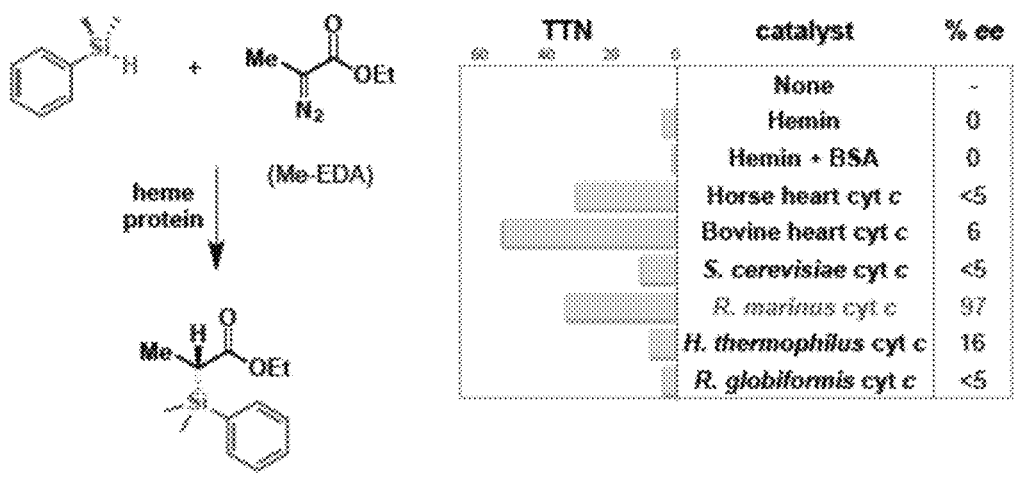
FIGS. 5A-5E show heme protein-catalyzed carbon-silicon bond formation.

Based on the idea that heme proteins can also catalyze carbene insertion into silicon-hydrogen bonds, directed evolution was used to create enzymes of the present invention. Because iron is not known to catalyze this transformation (24), it was first examined whether free heme could function as a catalyst in aqueous media. Initial experiments showed that the reaction between phenyldimethylsilane and ethyl 2-diazopropanoate (Me-EDA) in neutral buffer (M9-N minimal medium, pH 7.4) at room temperature gave racemic organosilicon (compound 3) at very low levels, a total turnover number (TTN) of 4 (FIG. 5A). No product formation was observed in the absence of heme, and the organosilicon product was stable under the reaction conditions.

Next, it was investigated whether heme proteins could catalyze the same carbon-silicon bond-forming reaction. Screening a panel of cytochrome P450 and myoglobin variants, product formation was observed with more turnovers compared to the hemin and hemin with bovine serum albumin (BSA) controls, but with negligible enantioinduction (Table 5). Surprisingly, cytochrome c from *Rhodothermus marinus* (Rma cyt c), a gram-negative, thermohalophilic bacterium from submarine hot springs in Iceland (25), catalyzed the reaction with 97% ee, indicating the reaction took place in an environment where the protein exerted excellent stereocontrol. Bacterial cytochromes c are well-studied, functionally conserved electron-transfer proteins that are not known to have any catalytic function in living systems (26). Other bacterial and eukaryotic cytochrome c proteins also catalyzed the reaction, but with lower selectivities. Rma cyt c was selected as the platform for evolving a carbon-silicon bond-forming enzyme.

TABLE 5

Preliminary experiments with heme and purified heme proteins

| Catalyst | TTN | % ee |
|---|---|---|
| Controls | | |
| None | 0 | — |
| Hemin | 4 ± 1 | 0 |
| Hemin + BSA | 1 ± 1 | 0 |

TABLE 5-continued

Preliminary experiments with heme and purified heme proteins

Ph-Si(Me)(Me)-H + N₂=C(Me)-C(O)-OEt → (Catalyst, M9-N buffer (pH 7.4), Na₂S₂O₄ room temperature, 1.5 hours) → H-C(Me)-C(O)-OEt with Si(Me)(Me)Ph

| Catalyst | TTN | % ee |
|---|---|---|
| P450s | | |
| BM3 P450 T268A (84) | 44 ± 15 | 0 |
| BM3 P450 T268A C400H (121) | 45 ± 3 | <5 |
| BM3 P450 CIS I263F C400S T438S (122) | 24 ± 9 | <5 |
| BM3 P450 F87A T268A C400S (123) | 40 ± 15 | <5 |
| BM3 P450 Hstar H92N H100N (124) | 46 ± 7 | 0 |
| Myoglobins | | |
| Sperm whale Mb | 12 ± 1 | 0 |
| Sperm whale Mb H64V V68A (125) | 17 ± 1 | 0 |
| Cytochromes c | | |
| Horse heart cyt c | 31 ± 10 | <5 |
| Bovine heart cyt c | 54 ± 2 | 6 |
| *S. cerevisiae* cyt c | 11 ± 1 | <5 |
| *R. marinus* cyt c | 34 ± 10 | 97 |
| *H. thermophilus* cyt c | 8 ± 2 | 16 |
| *R. globiformis* cyt c | 4 ± 1 | <5 |
| Others | | |
| Horse radish peroxidase | 0 | — |
| *C. glutamicum* catalase | 0 | — |

Figure 5B:
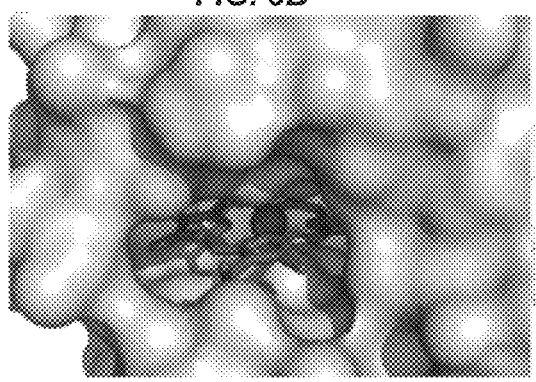
Figure 5C:
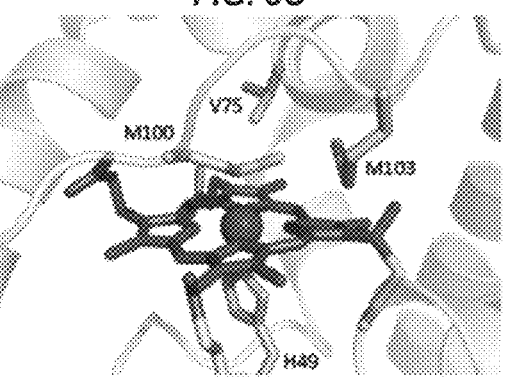
Figure 5D:
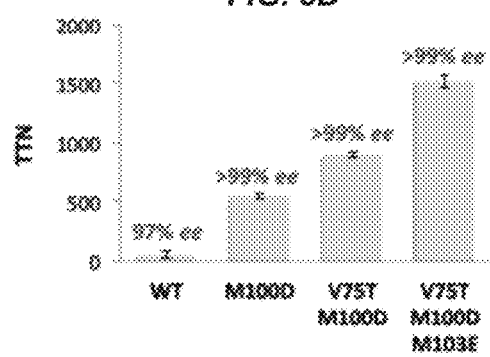
Figure 5E:
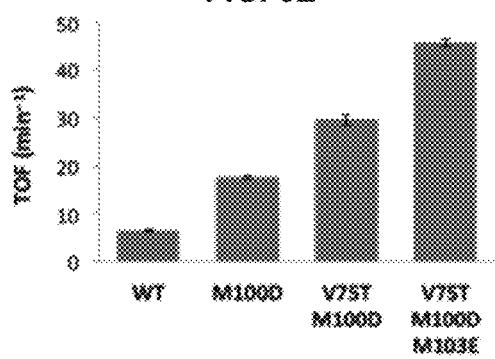

The crystal structure of wild-type Rma cyt c (PDB ID: 3CP5; 26) revealed that the heme prosthetic group resides in a hydrophobic pocket, with the iron axially coordinated to a proximal His (H49) and a distal Met (M100), the latter of which is located on a loop (FIGS. 5B and 5C). The distal Met, common in cytochrome c proteins, is coordinately labile (27,28) and was selected for mutation based on the idea that M100 must be displaced upon iron-carbenoid formation, and that mutation of this amino acid could facilitate formation of this adventitious "active site" and yield an improved carbon-silicon bond-forming biocatalyst. Therefore, a variant library made by site-saturation mutagenesis of M100 was cloned and recombinantly expressed in *E. coli*. After protein expression, the bacterial cells were heat-treated (75° C. for 10minutes) before screening in the presence of phenyldimethylsilane (10 mM), Me-EDA (10 mM) and sodium dithionite ($Na_2S_2O_4$ 10 mM) as a reducing agent, at room temperature under anaerobic conditions. The M100D mutation stood out as highly activating: this first-generation mutant provided chiral organosilicon (compound 3) as a single enantiomer in 550 TTN, a 12-fold improvement over the wild-type protein (FIG. 5D).

Amino acid residues V75 and M103 reside close (i.e., within 7Å) to the iron heme center of wild-type Rma cyt c. Sequential site-saturation mutagenesis at these positions the M100 mutant led to the discovery of triple mutant V75T M100D M103E, which catalyzed carbon-silicon bond formation in greater than , 1,500 turnovers and greater than 99% ee. This level of activity was more than 15 times the total turnovers reported for the best synthetic catalysts for this class of reaction (16). As stand-alone mutations, both V75T and M103E were activating for wild-type Rma cyt c and the beneficial effects increased with each combination (Tables 6 and 7 and FIG. 6). Comparison of the initial reaction rates established that each round of evolution enhanced the rate: relative to the wild-type protein, the evolved triple mutant catalyzed the reaction greater than 7-fold faster, with turnover frequency (TOF) of 46 $min^{-1}$ (Table 7).

TABLE 6

Carbon-silicon bond formation catalyzed by Rma cyt c variants

| Rma cyt c | TTN |
|---|---|
| WT | 44 ± 27 |
| M100D | 549 ± 24 |
| V75T | 150 ± 48 |
| M103E | 70 ± 21 |
| V75T M100D | 892 ± 20 |
| V75T M100E | 154 ± 37 |
| M100D M103E | 520 ± 88 |
| V75T M100D M103E | 1518 ± 51 |

TABLE 7

Comparison of carbon-silicon bond forming rates of four generations of Rma cyt c

| Rma cyt c variant | initial rate/μM $min^{-1}$ | turnover frequency (TOF)/$min^{-1}$ | TOF relative to WT |
|---|---|---|---|
| WT | 5.1 ± 0.3 | 6.4 ± 0.3 | 1 |
| M100D | 14.0 ± 0.4 | 17.5 ± 0.5 | 2.8 ± 0.2 |
| V75T M100D | 23.6 ± 0.8 | 29.5 ± 1.0 | 4.6 ± 0.3 |
| V75T M100D M103E | 3.64 ± 0.5 | 45.5 ± 0.7 | 7.1 ± 0.4 |

Figure 6:
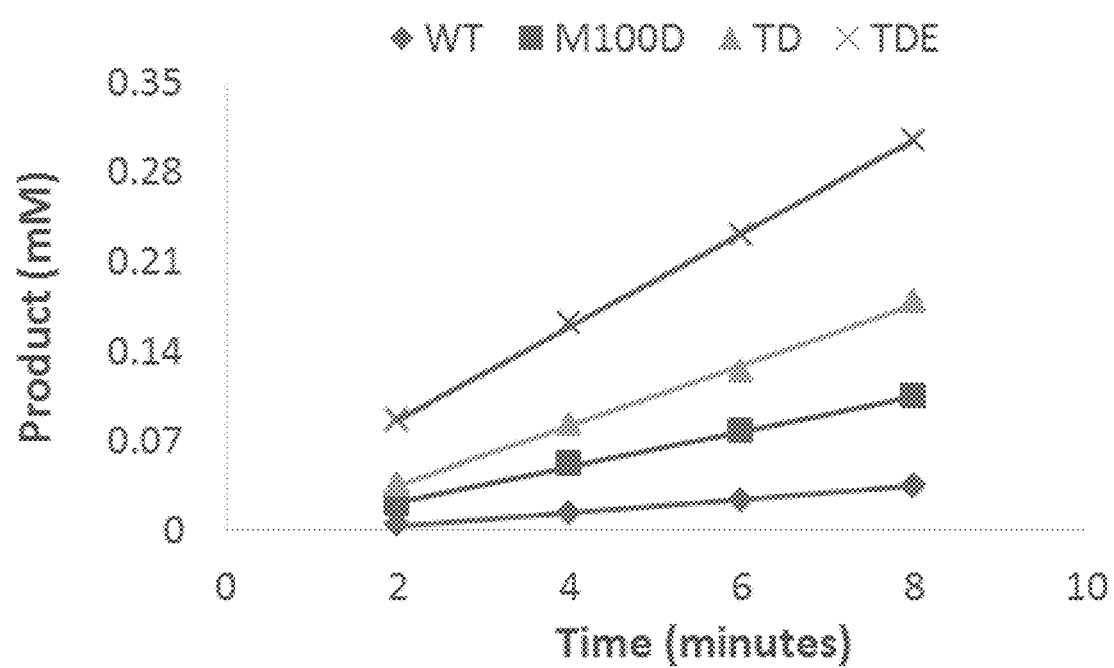
FIG. 6 shows a graph of product formation as a function of time for four generations of Rma cyt c.

Errors quoted in the table above are calculated from the standard deviations of the fitting of data in the product vs time plot shown in FIG. 6.

Figure 7:
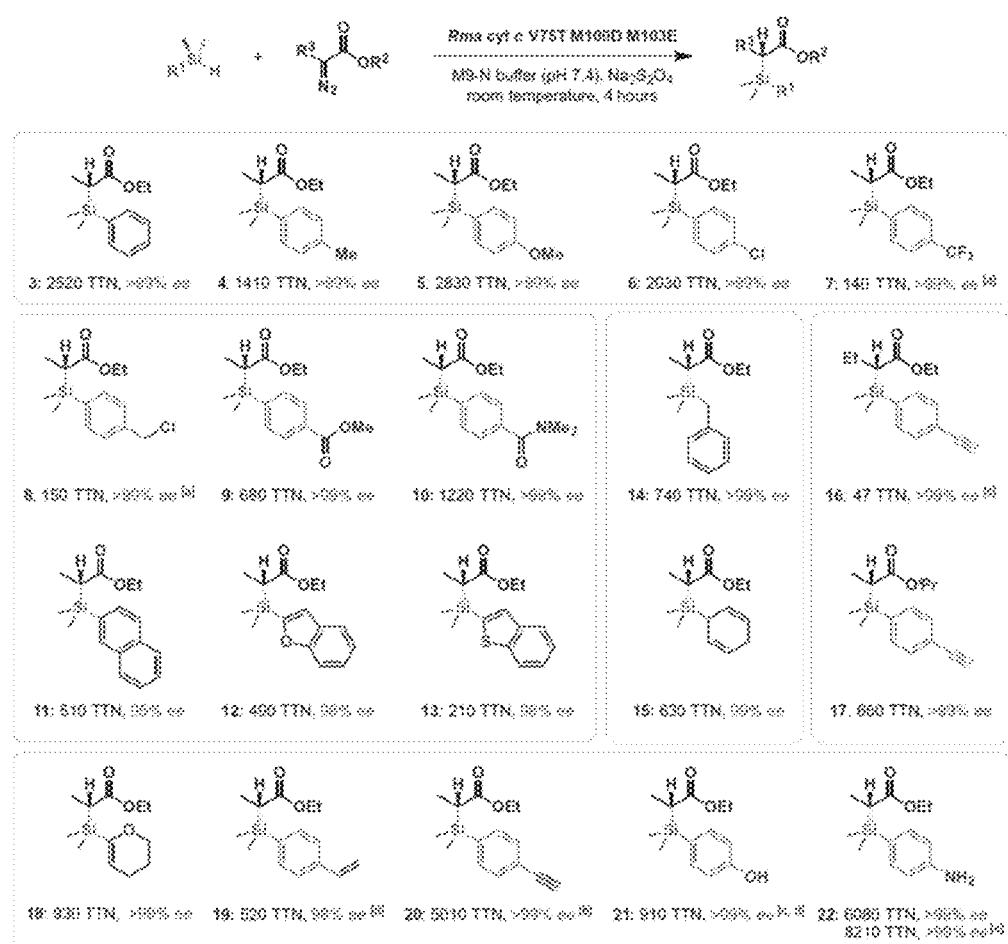
FIG. 7 shows the scope of Rma cyt c V75T M100D M103E-catalyzed carbon-silicon bond formation and the chemical structures of organosilicon products Compounds 3-22. Standard reaction conditions were: lysate of *E. coli* expressing Rma cyt c V75T M100D M103E ($OD_{600}$=1.5; heat-treated at 75° C. for 10 minutes), 20 mM silane, 10 mM diazo ester, 10 mM $Na_2S_2O_4$, 5 vol % MeCN, M9-N buffer (pH 7.4) at room temperature under anaerobic conditions. Reactions were performed in triplicate. [a] $OD_{600}$=5 lysate. [b] $OD_{600}$=0.5 lysate. [c] $OD_{600}$=15 lysate. [d] 10 mM silane. [e] $OD_{600}$=0.15 lysate.

Assaying the new enzyme against a panel of silicon and diazo reagents, it was found that the mutations were broadly activating for enantioselective carbon-silicon bond formation. The reaction substrate scope was surveyed using heat-treated lysates of *E. coli* expressing Rma cyt c V75T M100D M103E under saturating conditions for both silane and diazo ester to determine TTN. Whereas many natural enzymes excel at catalyzing reactions on only their native substrates and little else (especially primary metabolic enzymes), the triple mutant catalyzed the formation of twenty silicon-containing products, most of which were obtained cleanly as single enantiomers, showcasing the broad substrate scope of this reaction using just a single variant of the enzyme (FIG. 7). The reaction accepted both electron-rich and electron-deficient silicon reagents, accommodating a variety of functional groups including ethers, aryl halides, alkyl halides, esters and amides (compounds 5-10). Silicon reagents based on naphthalenes or heteroarenes (compounds 11-13) as well as vinyldialkyl- and trialkylsilanes could also serve as silicon donors (compounds 14, 15, and 18). In addition, diazo compounds other than Me-EDA could be used for carbon-silicon bond formation (compounds 16 and 17).

The evolved Rma cyt c exhibited high specificity for carbon-silicon bond formation. Even in the presence of functional groups that could compete in carbene-transfer reactions, enzymatic carbon-silicon bond formation proceeded with excellent chemoselectivity. For example, styrenyl olefins, electron-rich double bonds, and terminal alkynes that are prime reaction handles for synthetic derivatization were preserved under the reaction conditions, with no competing cyclopropanation or cyclopropenation activity observed. As a result, organosilicon products (compounds 12-13 and 18-20) were produced with 210 to 5,010 turnovers and excellent stereoselectivities (98 to greater than 99% ee). Preferential carbon-silicon bond formation could also be achieved with substrates bearing free alcohols and primary amines, affording silicon-containing phenol (compound 21) (910 TTN, greater than 99% ee) and aniline (compound 22) (8,210 TTN, greater than 99% ee). This capability removed the need for functional group protection and/or manipulation, offering a streamlined alternative to transition metal catalysis for incorporating silicon into small molecules. Indeed, when the same reactants were subjected to rhodium catalysis (1 mol % $Rh_2(OAc)_4$), O—H and N—H insertions were the predominant reaction pathways, and copper catalysis (10 mol % $Cu(OTf)_2$) gave complex mixtures of products (Table 8). Tolerance of these highly versatile functionalities in enzymatic carbon-silicon bond-forming reactions provides opportunities for their use in downstream processing through metabolic engineering, bioorthogonal chemistry, and other synthetic endeavors.

TABLE 8

Rh(II)- and Cu(II)-catalyzed reactions between Me-EDA and 4-(dimethylsilyl)phenol (compound 1k) or 4-(dimethylsilyl) aniline (compound 23)

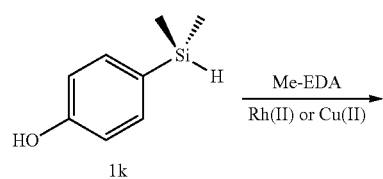

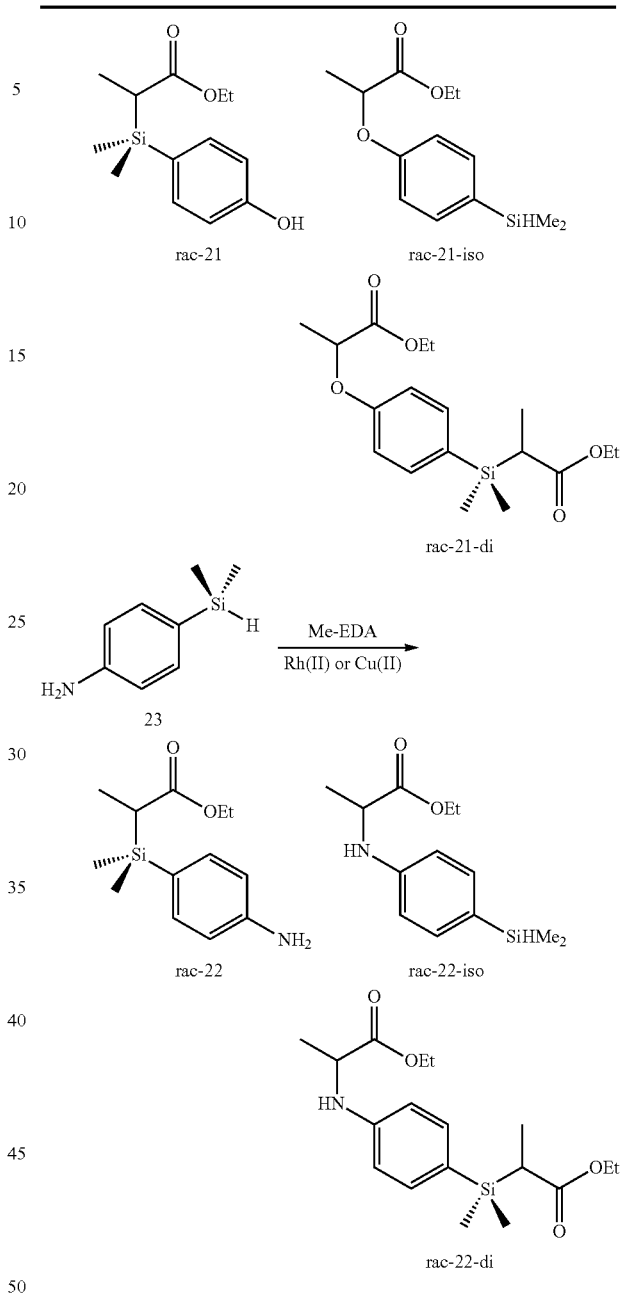

| | Compound 21 (Si—H insertion) | Compound 21-iso (O—H insertion) | Compound 21-di (double insertion) |
|---|---|---|---|
| $Rh_2(OAc)_4$ | ✗ | ✓ | ✓ |
| $Cu(OTf)_2$ | ✗ | ✗ | ✗ |

| | Compound 22 (Si—H insertion) | Compound 22-iso (N—H insertion) | Compound 22-di (double insertion) |
|---|---|---|---|
| $Rh_2(OAc)_4$ | ✗ | ✓ | ✗ |
| $Cu(OTf)_2$ | ✗ | ✗ | ✗ |

Note:
✗ = not detected;
✓ = detected.
$Cu(OTf)_2$ gave complex mixtures of products in both reactions.

Figures 8A, 8B:
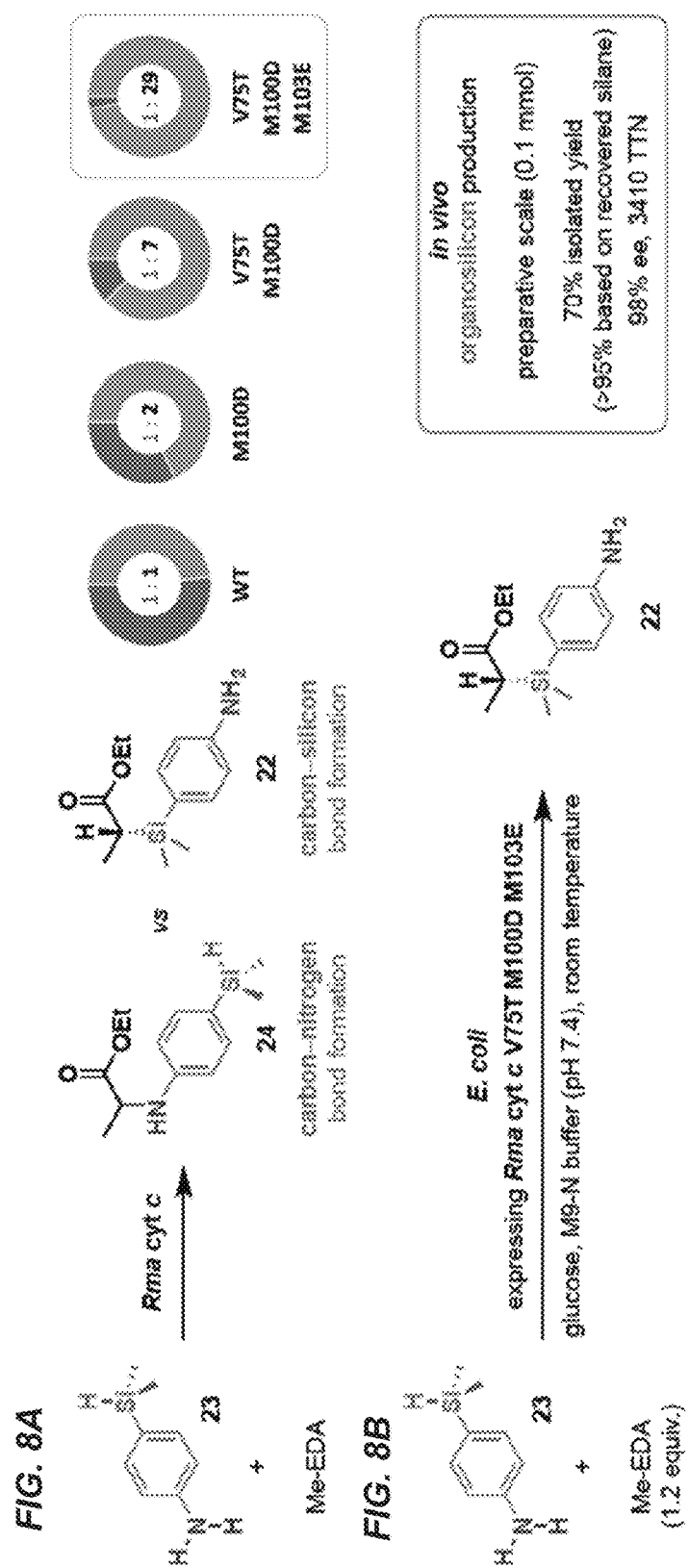
FIGS. 8A and 8B show the chemoselectivity and in vivo activity of evolved Rma cyt c.

Next, it was investigated whether all Rma cyt c variants could catalyze carbon-silicon bond formation selectively over insertion of the carbene into an N—H bond in the same substrate. The evolutionary lineage was re-visited and tested for all four generations of Rma cyt c (wild-type, M100D, V75T M100D and V75T M100D M103E) with Me-EDA and 4-(dimethylsilyl)aniline (Compound 23), a reagent that could serve as both a nitrogen and a silicon donor, to probe the proteins' bond-forming preferences. The wild-type cytochrome c in fact exhibited a slight preference for forming amination product (compound 24) over organosilicon product (Compound 22). Even though silane (Compound 23) was not used for screening, and the Rma cyt c therefore never underwent direct selection for chemoselectivity, each round of evolution effected a distinct shift from amination to carbon-silicon bond forming activity (FIG. 8A). This evolutionary path that focused solely on increasing desired product formation culminated in a catalyst that channeled the majority of the reactants (i.e., 97%) through carbon-silicon bond formation (i.e., greater than 30-fold improvement with respect to the wild-type). Without being bound to any particular theory, improvement was effected by optimizing the orientation and binding of the silicon donor.

Some fungi, bacteria and algae have demonstrated promiscuous capacities to derivatize organosilicon molecules when these substances were made available to them (1). The desire to establish silicon-based biosynthetic pathways led to the investigation of whether the evolved Rma cyt c could produce organosilicon products in vivo. E. coli whole cells ($OD_{600}$=15) expressing Rma cyt c V75T M100D M103E in glucose-supplemented M9-N buffer were given silane (compound 23) (0.1 mmol) and Me-EDA (0.12 mmol) as neat reagents. The enzyme in this whole-cell system catalyzed carbon-silicon bond formation with 3,410 turnovers, affording organosilicon product (compound 22) in 70% isolated yield (greater than 95% yield based on recovered silane (compound 23)) and 98% ee (FIG. 8B). These in vitro and in vivo examples of carbon-silicon bond formation using enzymes of the present invention and earth-abundant iron show that compositions and methods of the present invention are useful for efficiently forging chemical bonds not previously found in biology, thereby granting access to areas of chemical space which living systems have not yet explored.

Materials and Methods
Chemicals and Reagents

Unless otherwise noted, all chemicals and reagents for chemical reactions were obtained from commercial suppliers (Acros, Arch Bioscience, Fisher Scientific, Sigma-Aldrich, TCI America) and used without further purification. The following proteins were all purchased from Sigma-Aldrich: bovine serum albumin (BSA), cytochrome c (from bovine, equine heart and S. cerevisiae), peroxidase II (from horseradish), and catalase (from C. glutamicum). Silica gel chromatography purifications were carried out using AMD Silica Gel 60, 230-400 mesh. $^1$H and $^{13}$C NMR spectra were recorded on a Bruker Prodigy 400 MHz instrument and were internally referenced to the residual solvent peak (chloroform). $^{29}$Si NMR spectra were recorded on the same instrument and referenced to tetramethoxysilane (δ−78.9 ppm). Data for $^1$H NMR reported in the conventional form: chemical shift (δ ppm), multiplicity (s=singlet, d=doublet, t=triplet, q=quartet, hept=heptet, m=multiplet, br=broad, app=appears as), coupling constant (Hz), integration. Data for $^{13}$C and $^{29}$Si reported in terms of chemical shift (δ ppm). High-resolution mass spectra were obtained with a JEOL JMS-600H High Resolution Mass Spectrometer at the California Institute of Technology Mass Spectral Facility. Sonication was performed using a Qsonica Q500 sonicator. Chemical reactions were monitored using thin layer chromatography (Merck 60 silica gel plates) and a UV-lamp for visualization. Gas chromatography (GC) analyses were carried out using a Shimadzu GC-17A gas chromatograph, a FID detector, and J&W HP-5 (30 m×0.32 mm, 0.25 µm film; 90° C. hold 1 minute, 90 to 110° C. at 15° C./minute, 110 to 280° C. at 60° C./minute, 280° C. hold 1 minute, 6.2 minutes total). Analytical chiral supercritical fluid chromatography (SFC) was performed with a JACSO 2000 series instrument using i-PrOH and supercritical $CO_2$ as the mobile phase, with visualization at 210 nm. The following chiral columns were used: Daicel Chiralpak IC, Chiralpak AD-H, or Chiralcel OD-H (4.6 mm×25 cm).

Plasmid pET22 was used as a cloning vector, and cloning was performed using Gibson assembly (103). The cytochrome c maturation plasmid pEC86 (104) was used as part of a two-plasmid system to express prokaryotic cytochrome c proteins. Cells were grown using Luria-Bertani medium or HyperBroth (AthenaES) with 100 µg/mL ampicillin and 20 µg/mL chloramphenicol ($LB_{amp/chlor}$ or $HB_{amp/chlor}$). Cells without the pEC86 plasmid were grown with 100 µg/mL ampicillin ($LB_{amp}$ or $HB_{amp}$). Electrocompetent Escherichia coli cells were prepared following the protocol of Sambrook et al. (105). T5 exonuclease, Phusion polymerase, and Taq ligase were purchased from New England Biolabs (NEB, Ipswich, Mass.). M9-N minimal medium (abbreviated as M9-N buffer; pH 7.4) was used as a buffering system for whole cells, lysates, and purified proteins, unless otherwise specified. M9-N buffer was used without a carbon source; it contains 47.7 mM $Na_2HPO_4$, 22.0 mM $KH_2PO_4$, 8.6 mM NaCl, 2.0 mM $MgSO_4$, and 0.1 mM $CaCl_2$.

Plasmid Construction

All variants described in this example were cloned and expressed using the pET22(b)+ vector (Novagen). The gene encoding Rma cyt c (UNIPROT ID B3FQS5) was obtained as a single gBlock (IDT), codon-optimized for E. coli, and cloned using Gibson assembly (103) into pET22(b)+(Novagen) between restriction sites NdeI and XhoI in frame with an N-terminal pelB leader sequence (to ensure periplasmic localization and proper maturation; MKYLLPTAAAGLLL-LAAQPAMA (SEQ ID NO:3)) and a C-terminal 6×His-tag. This plasmid was co-transformed with the cytochrome c maturation plasmid pEC86 (104) into E. Cloni® EXPRESS BL21(DE3) cells (Lucigen).

Cytochrome c Expression and Purification

Purified cytochrome c proteins were prepared as follows. One liter $NB_{amp/chlor}$ in a 4 L flask was inoculated with an overnight culture (20 mL, $LB_{amp/chlor}$) of recombinant E. Cloni® EXPRESS BL21(DE3) cells containing a pET22 (b)+ plasmid encoding the cytochrome c variant, and the pEC86 plasmid. The culture was shaken at 37° C. and 200 rpm (no humidity control) until the $OD_{600}$ was 0.7 (approximately 3 hours). The culture was placed on ice for 30 minutes, and isopropyl β-D-1-thiogalactopyranoside (IPTG) and 5-aminolevulinic acid (ALA) were added to final concentrations of 20 µM and 200 µM respectively.

The incubator temperature was reduced to 20° C., and the culture was allowed to shake for 20 hours at 200 rpm. Cells were harvested by centrifugation (4° C., 15 minutes, 4,000× g), and the cell pellet was stored at −20° C. until further use (at least 24 hours). The cell pellet was resuspended in buffer containing 100 mM NaCl, 20 mM imidazole, and 20 mM Tris-HCl buffer (pH 7.5 at 25° C.) and cells were lysed by sonication (2 minutes, 2 seconds on, 2 seconds off, 40% duty cycle; Qsonica Q500 sonicator). Cell lysate was placed in a 75° C. heat bath for 10 minutes, and cell debris was removed by centrifugation for 20 minutes (5000×g, 4° C.). Supernatant was sterile filtered through a 0.45 µm cellulose acetate filter and purified using a 1 mL Ni-NTA column (HisTrap HP, GE Healthcare, Piscataway, N.J.) using an AKTA purifier FPLC system (GE healthcare). The cytochrome c protein was eluted from the column by running a gradient from 20 to 500 mM imidazole over 10 column volumes.

The purity of the collected cytochrome c fractions was analyzed using sodium dodecyl sulfate-polyacrylamide gel electrophoresis (SDS-PAGE). Pure fractions were pooled and concentrated using a 3 kDa molecular weight cut-off centrifugal filter and dialyzed overnight into 0.05 M phosphate buffer (pH=7.5) using 3 kDa molecular weight cut-off dialysis tubing. The dialyzed protein was concentrated again, flash-frozen on dry ice, and stored at −20° C.

The concentration of cytochrome c was determined in triplicate using the ferrous assay described below.

P450 and Globin Expression and Purification

Purified P450s and globins were prepared differently from the cytochrome c proteins, described as follows. One liter $HB_{amp}$ in a 4 L flask was inoculated with an overnight culture (20 mL, $LB_{amp}$) of recombinant E. Cloni® EXPRESS BL21(DE3) cells containing a pET22(b)+ plasmid encoding the P450 or globin variant. The culture was shaken at 37° C. and 200 rpm (no humidity control) until the $OD_{600}$ was 0.7 (approximately 3 hours). The culture was placed on ice for 30 minutes, and IPTG and 5-ALA were added to final concentrations of 0.5 mM and 1 mM, respectively. The incubator temperature was reduced to 20° C., and the culture was allowed to shake for 20 hours at 200 rpm. Cells were harvested by centrifugation (4° C., 15 minutes, 4,000×g), and the cell pellet was stored at −20° C. until further use (at least 24 hours). The cell pellet was resuspended in buffer containing 100 mM NaCl, 20 mM imidazole, and 20 mM Tris-HCl buffer (pH 7.5 at 25° C.). Hemin (30 mg/mL, 0.1 M NaOH; Frontier Scientific) was added to the resuspended cells such that 1 mg of hemin was added for every 1 gram of cell pellet. Cells were lysed by sonication (2 minutes, 1 seconds on, 2 seconds off, 40% duty cycle; Qsonica Q500 sonicator). Cell debris was removed by centrifugation for 20 minutes (27,000×g, 4° C.). Supernatant was sterile filtered through a 0.45 µm cellulose acetate filter, and purified using a 1 mL Ni-NTA column (HisTrap HP, GE Healthcare, Piscataway, N.J.) using an AKTA purifier FPLC system (GE healthcare). The P450 and globin proteins were eluted from the column by running a gradient from 20 to 500 mM imidazole over 10 column volumes.

The purity of the collected protein fractions was analyzed using SDS-PAGE. Pure fractions were pooled and concentrated using a 10 kDa molecular weight cut-off centrifugal filter and buffer-exchanged with 0.1 M phosphate buffer (pH=8.0). The purified protein was flash-frozen on dry ice and stored at −20° C.

P450 and globin concentrations were determined in triplicate using the hemochrome assay described below.

Hemochrome Assay

A solution of sodium dithionite (10 mg/mL) was prepared in M9-N buffer. Separately, a solution of 1 M NaOH (0.4 mL) was mixed with pyridine (1 mL), followed by centrifugation (10,000×g, 30 seconds) to separate the excess aqueous layer gave a pyridine-NaOH solution. To a cuvette containing 700 µL protein solution (purified protein or heat-treated lysate) in M9-N buffer, 50 µL of dithionite solution and 250 µL pyridine-NaOH solution were added.

The cuvette was sealed with Parafilm, and the UV-Vis spectrum was recorded immediately. Cytochrome c concentration was determined using $\varepsilon_{550-535}$=22.1 mM$^{-1}$ cm$^{-1}$ (106). Protein concentrations determined by the hemochrome assay were in agreement with that determined by the bicinchoninic acid (BCA) assay (Thermo Fisher) using bovine serum albumin (BSA) for standard curve preparation.

Ferrous Assay

Figure 9A:
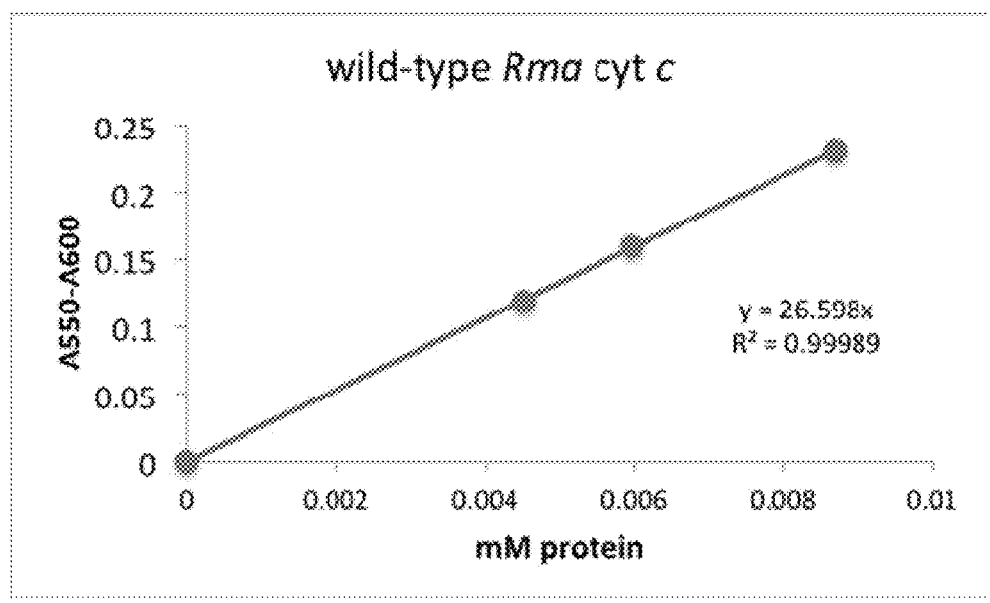
FIGS. 9A and 9B show ferrous assay calibration curves.
Figure 9B:
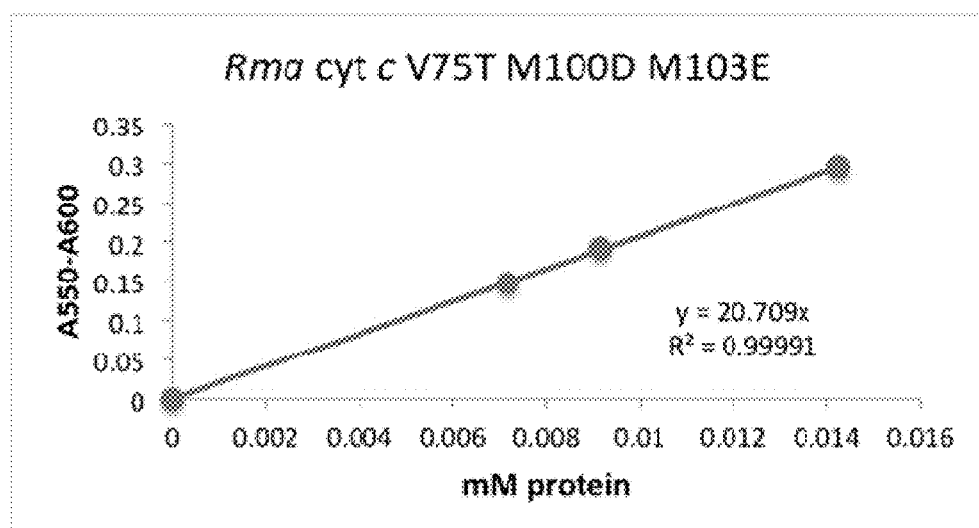
Figure 10:
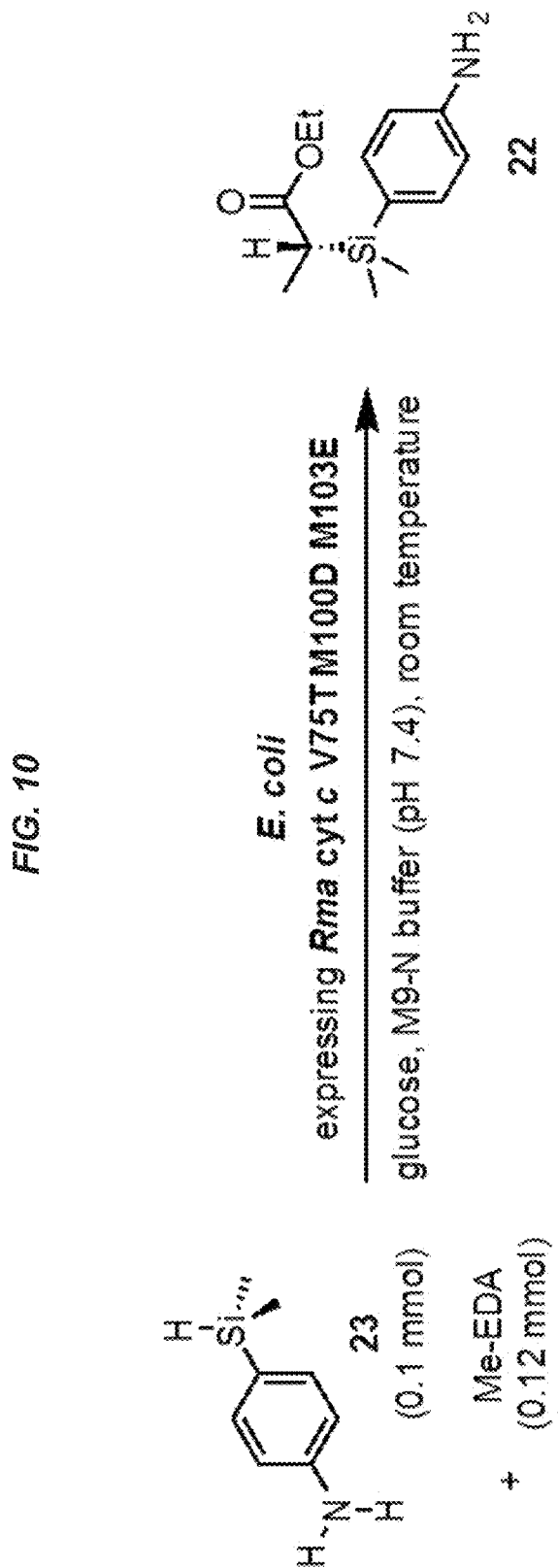
FIG. 10 shows a preparative-scale whole-cell biocatalytic reaction in which Compound 22 was synthesized using Compound 23 as the silicon-containing reagent and Me-EDA as the diazo substrate.
Figure 11:
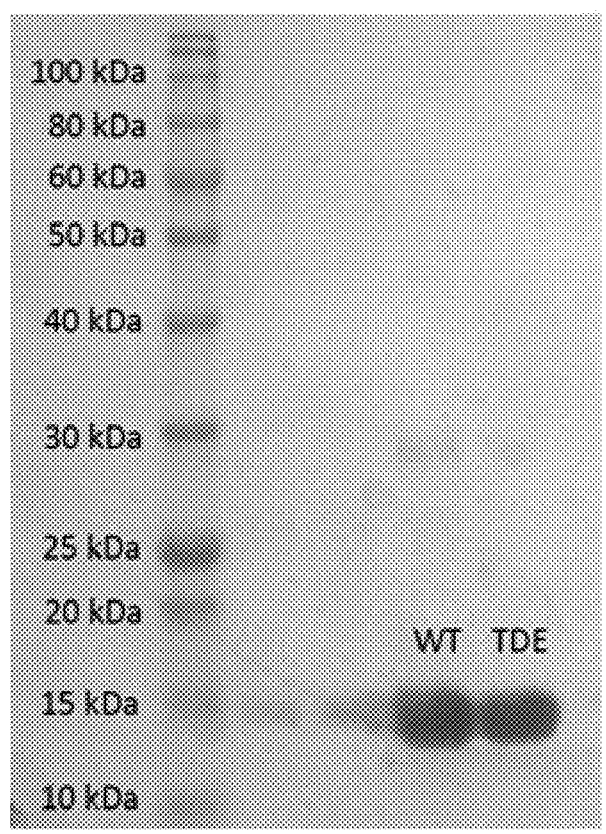
FIG. 11 shows a representative SDS-PAGE gel of purified wild-type Rma cyt c and its V75T M100D M103E variant (TDE) in comparison to a standard protein ladder. The second and third lanes from the left are the same samples loaded at lower protein concentrations.
Figure 12:
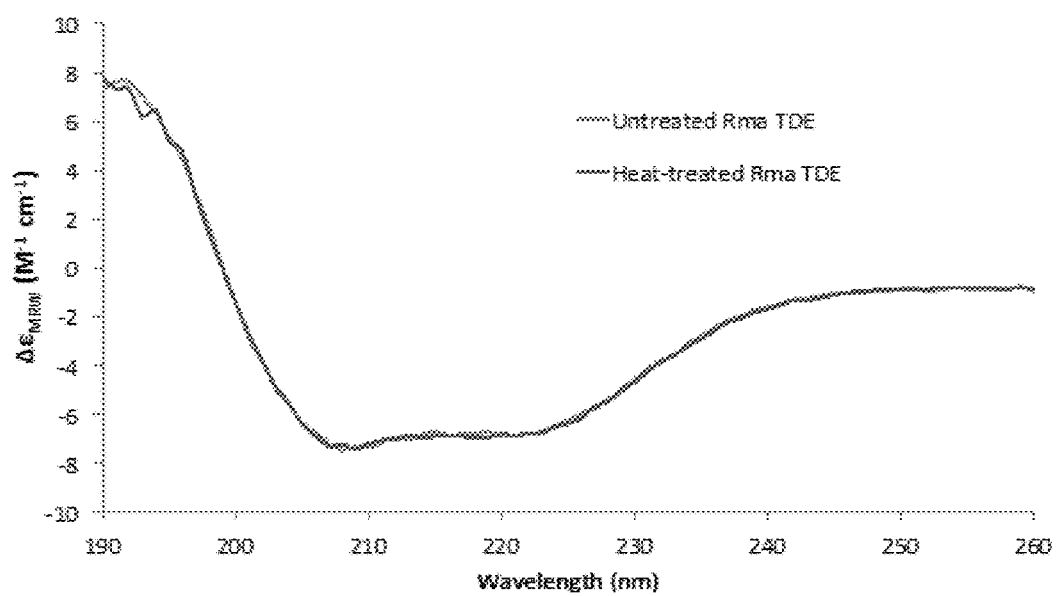
FIG. 12 shows circular dichroism (CD) spectra of purified Rma cyt c V75T M100D M103E (Rma TDE). Rma cyt c V75T M100D M103E was purified without performing the heat treatment step. Two identical samples were prepared in M9-N buffer, and one was heat treated at 75° C. for 10 minutes. After cooling to room temperature, the samples were analyzed by CD. The CD spectra of heat-treated and untreated Rma cyt c V75T M100D M103E were identical, suggesting that heat treatment at 75° C. for 10 minutes did not cause irreversible denaturation of the protein. The $\Delta\varepsilon_{MRW}$ values shown are similar to previously published values for wild-type Rma cyt c (Stelter et al. *Biochemistry* 47:11953-11963 (2008)), which shows that mutations V75T, M100D, and M103E were not highly disruptive to the protein secondary structure.
Figure 13A:
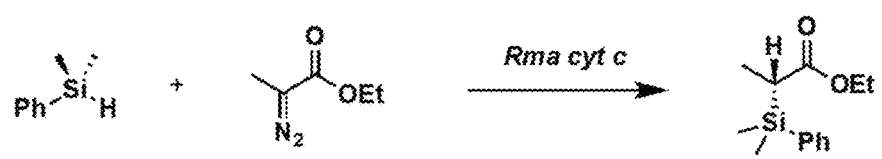
FIGS. 13A-13C show a binding mode for the iron carbenoid in wild-type Rma cyt c and reaction trajectory for carbon-silicon bond formation.
Figure 13B:
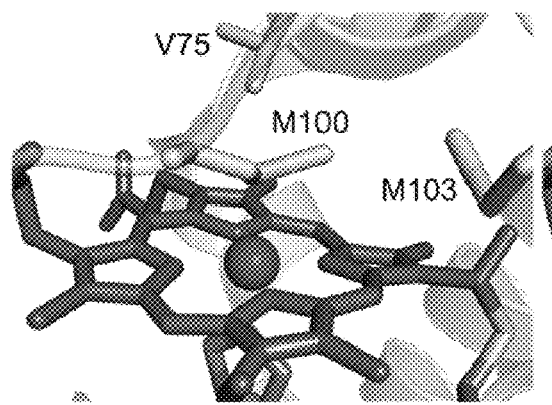
Figure 13C:
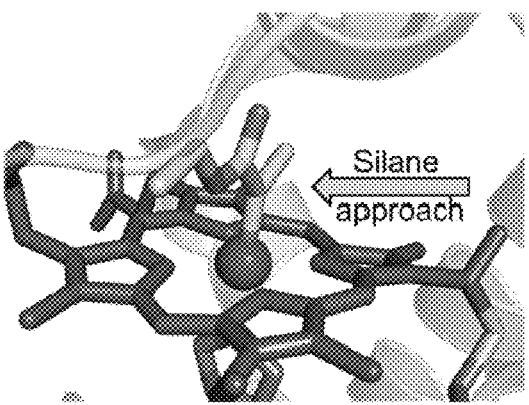

To a cuvette containing 700 µL protein solution in M9-N buffer was added 50 µL of dithionite solution (10 mg/mL in M9-N buffer). The cuvette was sealed with Parafilm, and the UV-Vis spectrum was recorded immediately. The absorbance value for the peak at 550 nm was recorded, and background absorbance at 600 nm was subtracted. Using the protein concentration as determined by the hemochrome assay, ferrous $\varepsilon_{550-600}$ was determined to be 27 mM$^{-1}$ cm$^{-1}$ for wild-type Rma cyt c, and 21 mM$^{-1}$ cm$^{-1}$ for Rma V75T M100D M103E (see, FIGS. 9A and 9B). Concentrations of Rma M100D and V75T M100D were determined using the extinction coefficient calculated for V75T M100D M103E.

Library Construction

Cytochrome c site-saturation mutagenesis libraries were generated using a modified version of the 22-codon site-saturation method (107). For each site-saturation library, oligonucleotides were ordered such that the coding strand contained the degenerate codon NDT, VHG or TGG. The reverse complements of these primers were also ordered. The three forward primers were mixed together in a 12:9:1 ratio, (NDT:VHG:TGG) and the three reverse primers were mixed similarly. Two PCR reactions were performed, pairing the mixture of forward primers with a pET22(b)+ internal reverse primer, and the mixture of reverse primers with a pET22b internal forward primer. The two PCR products were gel purified, ligated together using Gibson assembly (103), and transformed into E. Cloni® EXPRESS BL21(DE3) cells.

Enzyme Library Screening

Single colonies were picked with toothpicks off of $LB_{amp/chlor}$ agar plates, and grown in deep-well (2 mL) 96-well plates containing $LB_{amp/chlor}$ (400 µL) at 37° C., 250 rpm shaking, and 80% relative humidity overnight. After 16 hours, 30 µL aliquots of these overnight cultures were transferred to deep-well 96-well plates containing $HB_{amp/chlor}$ (1 mL) using a 12-channel EDP3-Plus 5-50 µL pipette (Rainin). Glycerol stocks of the libraries were prepared by mixing cells in $LB_{amp/chlor}$ (100 µL) with 50% v/v glycerol (100 µL). Glycerol stocks were stored at −78° C. in 96-well microplates. Growth plates were allowed to shake for 3 hours at 37° C., 250 rpm shaking, and 80% relative humidity. The plates were then placed on ice for 30 minutes. Cultures were induced by adding 10 µL of a solution, prepared in sterile deionized water, containing 2 mM isopropyl β-D-1-thiogalactopyranoside (IPTG) and 20 mM ALA. The incubator temperature was reduced to 20° C., and the induced cultures were allowed to shake for 20 hours (250 rpm, no humidity control). Cells were pelleted (4,000×g, 5 min, 4° C.) and resuspended in 500 µL M9-N buffer. For cell lysis, plates were placed in a 75° C. water bath for 10 minutes, followed by centrifugation (4,000×g, 5 min, 4° C.) to remove cell debris. The resulting heat-treated lysates (340 µL) were then transferred to deep-well plates for biocatalytic reactions. In an anaerobic chamber, to deep-well plates of heat-treated lysates were added Na$_2$S$_2$O$_4$ (40 μL per well, 100 mM in dH$_2$O), PhMe$_2$SiH (10 μL per well, 400 mM in MeCN) and Me-EDA (10 μL per well, 400 mM in MeCN). The plates were sealed with aluminum sealing tape, removed from the anaerobic chamber, and shaken at 400 rpm for 1.5 hours. After quenching with cyclohexane (1 mL), internal standard was added (20 μL of 20 mM methyl 2-phenylacetate in cyclohexane) and the reaction mixtures were pipetted up and down to thoroughly mix the organic and aqueous layers. The plates were centrifuged (4,000×g, 5 minutes) and the organic layer (400 μL) was transferred to shallow-well 96-well plates for SFC analysis. Hits from library screening were confirmed by small-scale biocatalytic reactions, which were analyzed by GC and SFC for accurate determination of turnovers and enantioselectivities.

Protein Lysate Preparation

Protein lysates for biocatalytic reactions were prepared as follows: E. coli cells expressing Rma cyt c variants were pelleted (4,000×g, 5 minutes, 4° C.), resuspended in M9-N buffer and adjusted to the appropriate OD$_{600}$. The whole-cell solution was heat-treated (75° C. for 10 minutes) then centrifuged (14,000×g, 10 minutes, 4° C.) to remove cell debris. The supernatant was sterile filtered through a 0.45 μm cellulose acetate filter into a 6 mL crimp vial, crimp sealed, and the head space of the crimp vial was degassed by bubbling argon through for at least 10 minutes. The concentration of cytochrome c protein lysate was determined using the ferrous assay described above. Using this protocol, the protein concentrations typically observed for OD$_{600}$=15 lysates were in the 8-15 μM range for wild-type Rma cyt c and 2-10 μM for other Rma cyt c variants.

Preliminary Experiments with Heme and Purified Heme Proteins

Commercially available heme proteins were screened to identify the most enantioselective protein variant as a starting point for directed evolution. Experiments with heme proteins were performed using 10 μM purified heme protein, 10 mM silane, 10 mM diazo ester, 10 mM Na$_2$S$_2$O$_4$, 5 vol % MeCN, M9-N buffer at room temperature under anaerobic conditions for 1.5 hours. Experiments with hemin were performed using 100 μM hemin. Experiments with hemin and BSA were performed using 100 μM hemin in the presence of BSA (0.75 mg/mL). Reactions were performed in triplicate. TTNs reported as the average of three experiments. Within instrument detection limit, variability in % ee was not observed. Unreacted starting materials were observed at the end of all reactions and no attempt was made to optimize these reactions.

Carbon-Silicon Bond Formation Catalyzed by Rma Cyt c Variants

Experiments were performed using lysates of E. coli expressing a Rma cyt c variant (OD$_{600}$=15; heat-treated at 75° C. for 10 minutes), 10 mM silane, 10 mM diazo ester, 10 mM Na$_2$S$_2$O$_4$, 5 vol % MeCN, M9-N buffer at room temperature under anaerobic conditions for 1.5 hours. Reactions were performed in triplicate. TTNs reported as the average of three experiments.

Small-Scale Biocatalytic Reaction

In an anaerobic chamber, protein lysate (340 μL) in a 2 mL crimp vial was added to 40 μL Na$_2$S$_2$O$_4$ (100 mM in dH$_2$O), 10 μL PhMe$_2$SiH (400 or 800 mM in MeCN), and 10 μL Me-EDA (400 mM in MeCN). The vial was crimp sealed, removed from the anaerobic chamber, and shaken at 400 rpm at room temperature for the stated reaction time. At the end of the reaction, the crimp vial was opened and the reaction was quenched with cyclohexane (1 mL). Internal standard was added (20 μL of 20 mM 2-phenylethanol in cyclohexane) and the reaction mixture was transferred to a microcentrifuge tube, vortexed (10 seconds, 3 times), then centrifuged (14,000×g, 5 min) to completely separate the organic and aqueous layers (the vortex-centrifugation step was repeated if complete phase separation was not achieved). The organic layer (750 μL) was removed for GC and SFC analysis. All biocatalytic reactions were performed in triplicate unless otherwise stated. The total turnover numbers (TTNs) reported were calculated with respect to the protein catalyst and represented the total number of turnovers that is possible to obtain from the catalyst under the stated reaction conditions.

Determining Carbon-Silicon Bond Formation Rates

To determine the initial reaction rate, experiments were performed using purified Rma cyt c variants (0.8 μM), 10 mM silane, 10 mM diazo ester, 10 mM Na$_2$S$_2$O$_4$, 5 vol % MeCN, M9-N buffer at room temperature under anaerobic conditions for various time intervals. The data used for determining the initial rate of each Rma cyt c variant is shown in the graph in FIG. 6.

For the timed experiments, the following procedure was used: in an anaerobic chamber, 1 mL Na$_2$S$_2$O$_4$ (100 mM in dH$_2$O) was added to 4 mL purified Rma cyt c protein (2.0 μM in M9-buffer) to give Solution 1. To four 2 mL microcentrifuge tubes were each added 180 μL M9-N buffer, 10 μL PhMe$_2$SiH (400 mM in MeCN) and 10 μL Me-EDA (400 mM in MeCN), and the mixtures were mixed thoroughly on a shaker (480 rpm for 2 min). To these mixtures were added 200 μL Solution 1, and the microcentrifuge tubes were closed and quickly shaken by hand for 3 seconds to ensure thorough mixing, before the tubes were returned to the shaker. The reactions were stopped at specific time points (2 minutes, 4 minutes, 6 minutes, and 8 minutes) by quick addition (within 10 seconds) of 40 μL pyridine solution (400 mM in dH$_2$O), 20 μL internal standard (20 mM acetophenone in toluene) and 1 mL cyclohexane. (Note: pyridine was added as a quencher to significantly slow down the reaction.). After the mixtures were vortexed for 20 seconds, 200 μL organic layer was immediately removed for GC analysis.

Rh(II)- and Cu(II)-Catalyzed Reactions

Rh$_2$(OAc)$_4$ and Cu(OTf)$_2$, which are known to catalyze carbene insertion into Si—H bonds under ligand-free conditions (126), were tested for their chemoselectivities towards Si—H, O—H and N—H insertions (Table 4). To a 5 mL vial was added silane (0.1 mmol, 1.0 equiv.), metal catalyst (Rh$_2$(OAc)$_4$ (0.44 mg, 1 mol %) or Cu(OTf)$_2$ (3.62 mg, 10 mol %)) and DCM (0.5 mL). The mixture was cooled to −78° C. before a solution of Me-EDA (25 μL, 2.0 equiv.) in DCM (0.3 mL) was added dropwise. After slowly warming up to room temperature in 4 hours, the reaction mixture was filtrated through a short pad of silica, diluted with DCM, and analyzed by GC-MS.

Products isolated from Rh$_2$(OAc)$_4$-catalyzed reactions with compounds 1k and 23 are shown below. Both reactions generated multiple products, rendering product purification and quantitative analysis of these reactions difficult. Multiple rounds of purification by silica column chromatography were required to obtain samples suitable for characterization; yields were therefore not determined for these reactions. Notably, Si—H insertion products (compounds 21 and 22) were not observed in these reactions.

A Rh$_2$(OAc)$_4$-catalyzed reaction with compound 1k afforded Compound rac-21-di and Compound rac-21-iso:

Compound rac-21-di

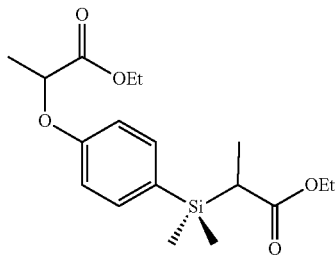

¹H NMR (400 MHz, CDCl₃) δ 7.40 (d, J=8.6 Hz, 2H), 6.87 (d, J=8.7 Hz, 2H), 4.75 (q, J=6.8 Hz, 1H), 4.22 (q, J=7.1 Hz, 2H), 4.01 (q, J=7.1 Hz, 2H), 2.21 (q, J=7.1 Hz, 1H), 1.62 (d, J=6.8 Hz, 3H), 1.25 (t, J=7.1 Hz, 3H), 1.17-1.10 (m, 6H), 0.33 (s, 6H). ¹³C NMR (100 MHz, CDCl₃) δ 176.19, 172.25, 158.86, 135.54, 128.29, 128.28, 114.65, 72.42, 61.46, 59.93, 30.30, 18.68, 14.47, 14.28, 11.43, −3.77, −4.60. HRMS (FAB) m/z: 352.1714 (M⁺); calc. for $C_{18}H_{28}SiO_5$: 352.1706.

Compound rac-21-iso (this Compound was Inseparable from Impurities)

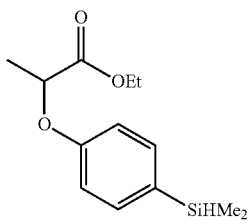

¹H NMR (400 MHz, CDCl₃) δ 7.44 (d, J=8.7 Hz, 2H), 6.87 (d, J=8.7 Hz, 2H), 4.76 (q, J=6.8 Hz, 1H), 4.39 (hept, J=3.7 Hz, 1H), 4.22 (q, J=6.9 Hz, 2H), 1.62 (d, J=6.8 Hz, 3H), 1.26 (t, J=7.1 Hz, 3H), 0.31 (d, J=3.8 Hz, 6H).

A Rh₂(OAc)₄-catalyzed reaction with compound 23 afforded Compound rac-22-iso and the corresponding double N—H insertion product:

Compound rac-22-iso

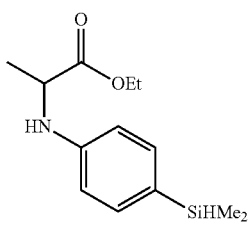

¹H NMR (400 MHz, CDCl₃) δ 7.24-7.17 (m, 2H), 6.88-6.68 (m, 3H), 4.68 (dq, J=5.5, 2.8 Hz, 1H), 4.22-4.11 (m, 3H), 1.50 (br d, J=6.4 Hz, 3H), 1.25 (t, J=7.1 Hz, 3H), 0.19 (d, J=2.8 Hz, 6H). ¹³C NMR (100 MHz, CDCl₃) δ 173.94, 135.20, 129.50, 119.78, 114.93, 61.47, 53.20, 18.62, 14.31, 0.71. HRMS (FAB) m/z: 250.1253 ((M+H)—H₂⁺); calc. for $C_{13}H_{20}SiNO_2$: 250.1263.

Interestingly, the following compound was also isolated as a mixture of diastereomers. The counter anion of the ammonium salt was not determined.

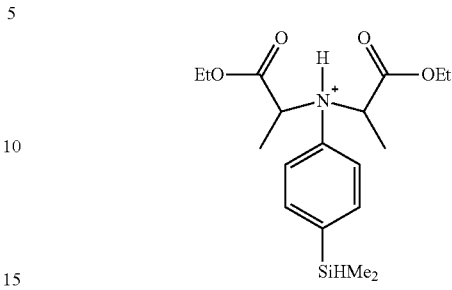

¹H NMR (400 MHz, CDCl₃) δ 7.22 (overlapping doublets, J=8.8, 7.3 Hz, 2H), 6.84 (t, J=7.3 Hz, 1H), 6.78 (br d, J=7.9 Hz, 2H), 4.99-4.55 (m, 1H), 4.44 (q, J=7.1 Hz, 2H), 4.23 (app qd, J=7.2, 2.0 Hz, 4H), 1.55 (d, J=7.2 Hz, 6H), 1.29 (t, J=7.1 Hz, 6H), 0.30-0.19 (m, 6H). ¹³C NMR (100 MHz, CDCl₃) δ 174.40, 146.38, 128.89, 119.30, 117.17, 61.24, 56.24, 15.95, 14.34, 0.71. HRMS (FAB) m/z: 352.1958 (M⁺); calc. for $C_{18}H_{30}SiNO_4$: 352.1944.

Substrate Synthesis and Characterization

The following commercially available substrates were used as received: phenyldimethylsilane (Sigma-Aldrich), benzyldimethylsilane (Sigma-Aldrich), and ethyl 2-diazopropanoate (Arch Bioscience). The following diazo compounds were prepared according to literature procedures: isopropyl 2-diazopropanoate (128), ethyl 2-diazobutanoate (129). The preparation and characterization of Compounds 1b, 1c, 1d, 1e, 1f, 1g, 1h, 1i, 1k, 1ks, 23, 23s, 1m, 1n, 1o, 1p, 1q, 1r are described below.

Dimethyl(p-tolyl)silane (Compound 1b)

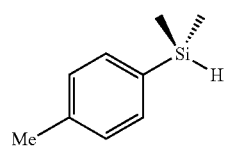

In a 100 mL round-bottom flask, chlorodimethylsilane (1.11 mL, 10.0 mmol) in THF (6 mL) was cooled to 0° C. A solution of 4-methylphenylmagnesium bromide (24 mL, 0.5 M in THF) was added dropwise slowly over 15 minutes. Then the reaction was allowed to warm to room temperature and stirred for 8 hours. The reaction mixture was quenched with NH₄Cl (5 mL, sat. aq.) and the product was extracted with Et₂O (15 mL×3). The organic layer was washed with water (20 mL), then brine (20 mL), then dried over MgSO₄ and concentrated under reduced pressure (200 torr). The crude product was purified by silica column chromatography with pentane to afford Compound 1b (1.27 g, 8.44 mmol, 84%). This compound is known (130). ¹H NMR (400 MHz, CDCl₃) δ 7.48 (d, J=7.8 Hz, 2H), 7.23 (d, J=7.4 Hz, 2H), 4.46 (hept, J=3.7 Hz, 1H), 2.39 (s, 3H), 0.37 (d, J=3.7 Hz, 6H).

(4-Methoxyphenyl)dimethylsilane (Compound 1c)

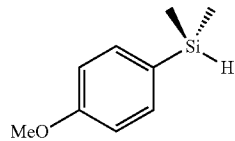

In a 100 mL round-bottom flask, chlorodimethylsilane (1.11 mL, 10.0 mmol) in THF (6 mL) was cooled to 0° C. A solution of 4-methoxyphenylmagnesium bromide (24 mL, 0.5 M in THF) was added dropwise slowly over 15 minutes. Then the reaction was allowed to warm to room temperature and stirred for 8 hours. The reaction mixture was quenched with NH$_4$Cl (5 mL, sat. aq.) and the product was extracted with Et$_2$O (15 mL×3). The organic layer was washed with water (20 mL), then brine (20 mL), then dried over MgSO$_4$ and concentrated under reduced pressure (200 torr). The crude product was purified by silica column chromatography with pentane/Et$_2$O (10:1) to afford Compound 1c (1.60 g, 9.62 mmol, 96%). This compound is known (130). $^1$H NMR (400 MHz, CDCl$_3$) δ 7.51 (d, J=8.7 Hz, 2H), 6.96 (d, J=8.6 Hz, 2H), 4.75-4.19 (m, 1H), 3.85 (s, 3H), 0.37 (d, J=3.8 Hz, 6H).

(4-Chlorophenyl)dimethylsilane (Compound 1d)

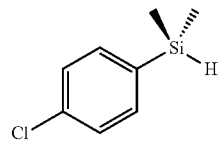

In a 100 mL round-bottom flask, chlorodimethylsilane (1.11 mL, 10.0 mmol) in THF (6 mL) was cooled to 0° C. A solution of 4-chlorophenylmagnesium bromide (24 mL, 0.5 M in THF) was added dropwise slowly over 15 minutes. Then the reaction was allowed to warm to room temperature and stirred for 8 hours. The reaction mixture was quenched with NH$_4$Cl (5 mL, sat. aq.) and the product was extracted with Et$_2$O (15 mL×3). The organic layer was washed with water (20 mL), then brine (20 mL), then dried over MgSO$_4$ and concentrated under reduced pressure (200 torr). The crude product was purified by silica column chromatography with pentane to afford Compound 1d (1.27 g, 7.45 mmol, 75%). This compound is known (130). $^1$H NMR (400 MHz, CDCl$_3$) δ 7.46 (d, J=8.3 Hz, 2H), 7.34 (d, J=8.2 Hz, 2H), 4.41 (hept, J=3.8 Hz, 1H), 0.34 (d, J=3.7 Hz, 6H).

(4-(Trifluoromethyl)phenyl)dimethylsilane (Compound 1e)

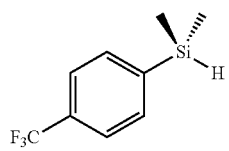

In a 100 mL round-bottom flask, 1-bromo-4-(trifluoromethyl)benzene (1.4 mL, 10.0 mmol) in THF (15 mL) was cooled to −78° C. n-BuLi (7.5 mL, 1.6 M in hexane) was added dropwise slowly over 15 minutes. The resulting mixture was stirred at −78° C. for 2 hours before the dropwise addition of chlorodimethylsilane (1.0 mL, 9.0 mmol). The reaction was allowed to warm to room temperature and stirred for 8 hours. The reaction mixture was quenched with NH$_4$Cl (5 mL, sat. aq.) and the product was extracted with Et$_2$O (15 mL×3). The organic layer was washed with water (20 mL), then brine (20 mL), then dried over MgSO$_4$ and concentrated under reduced pressure (200 torr). The crude product was purified by silica column chromatography with pentane to afford Compound 1e (0.81 g, 3.97 mmol, 40%). This compound is known (130). $^1$H NMR (400 MHz, CDCl$_3$) δ 7.66 (d, J=7.7 Hz, 2H), 7.60 (d, J=7.9 Hz, 2H), 4.46 (hept, J=3.8 Hz, 1H), 0.38 (d, J=3.8 Hz, 6H).

(4-(Chloromethyl)phenyl)dimethylsilane (Compound 1f)

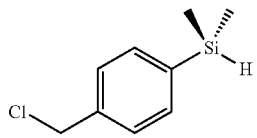

In a 250 mL round-bottom flask, (4-bromophenyl)methanol (5.61 g, 30.0 mmol) in THF (100 mL) was cooled to −78° C. n-BuLi (30.0 mL, 2.5 M in hexane) was added dropwise slowly over 30 minutes. The resulting mixture was stirred at −78° C. for 2 hours before the dropwise addition of chlorodimethylsilane (4.5 mL, 40.0 mmol). The reaction was allowed to warm to room temperature and stirred for 8 hours. The reaction mixture was quenched with NH$_4$Cl (50 mL, sat. aq.) and the product was extracted with DCM (50 mL×3). The organic layer was washed with water (20 mL), then brine (20 mL), then dried over MgSO$_4$ and concentrated under reduced pressure (100 torr). The crude product was purified by silica column chromatography with EtOAc/hexane (1:3) to afford (4-(dimethylsilyl)phenyl)methanol (2.96 g, 17.8 mmol, 59%). This compound is known (131). $^1$H NMR (400 MHz, CDCl$_3$) δ 7.55 (d, J=8.0 Hz, 2H), 7.37 (d, J=8.1 Hz, 2H), 4.70 (s, 2H), 4.43 (hept, J=3.7 Hz, 1H), 0.35 (d, J=3.8 Hz, 6H).

To a solution of (4-(dimethylsilyl)phenyl)methanol (498.9 mg, 3.0 mmol) in DCM (4 mL) were added triethylamine (0.5 mL, 3.6 mmol) and 4-methylbenzenesulfonyl chloride (629.1 mg, 3.3 mmol). The reaction mixture was stirred at room temperature for 8 hours. The reaction was then diluted with DCM (10 mL) and washed with water (20 mL), then brine (20 mL), then dried over MgSO$_4$ and the organic layer was concentrated under reduced pressure (100 torr). The crude product was purified by silica column chromatography with pentane to afford Compound 1f (0.22 g, 1.19 mmol, 40%). $^1$H NMR (400 MHz, CDCl$_3$) δ 7.55 (d, J=8.0 Hz, 2H), 7.39 (d, J=7.9 Hz, 2H), 4.59 (s, 2H), 4.43 (hept, J=3.8 Hz, 1H), 0.35 (d, J=3.8 Hz, 6H). HRMS (FAB) m/z: 183.0399 ((M+H)—H$_2$$^+$); calc. for C$_9$H$_{12}$SiCl: 183.0397.

Methyl 4-(dimethylsilyl)benzoate (Compound 1g)

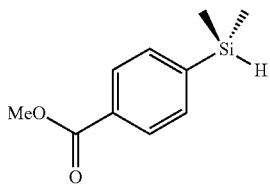

In a 100 mL round-bottom flask, methyl 4-iodobenzoate (2.62 g, 10.0 mmol) in THF (15 mL) was cooled to −78° C. i-PrMgCl (6 mL, 2.0 M in Et$_2$O) was added dropwise slowly over 5 minutes. The resulting mixture was allowed to warm to −40° C. in 2 hours and maintained at −40° C. for another 2 hours before the dropwise addition of chlorodimethylsilane (1.2 mL, 11.0 mmol). The reaction was allowed to warm to room temperature and stirred for 8 hours. The reaction mixture was quenched with NH$_4$Cl (5 mL, sat. aq.) and the product was extracted with DCM (15 mL×3). The organic layer was washed with water (20 mL), then brine (20 mL), then dried over MgSO$_4$ and concentrated under reduced pressure (100 torr). The mixture was dissolved in Et$_2$O (5 mL) and treated with hexane (25 mL). This crashed out most of the starting material, which was removed by filtration. The filtrate was collected, concentrated under reduced pressure, and purified by silica column chromatography with EtOAc/hexane (1:20) to afford Compound 1g (0.88 g, 4.53 mmol, 45%). $^1$H NMR (400 MHz, CDCl$_3$) δ 8.00 (d, J=8.1 Hz, 2H), 7.62 (d, J=8.2 Hz, 2H), 4.45 (hept, J=3.8 Hz, 1H), 3.92 (s, 3H), 0.37 (d, J=3.8 Hz, 6H). $^{13}$C NMR (100 MHz, CDCl$_3$) δ 167.35, 143.92, 134.13, 130.78, 128.72, 52.27, −3.84. HRMS (FAB) m/z: 195.0843 (M+H$^+$); calc. for C$_{10}$H$_{15}$SiO$_2$: 195.0841.

4-(dimethylsilyl)-N,N-dimethylbenzamide (Compound 1h)

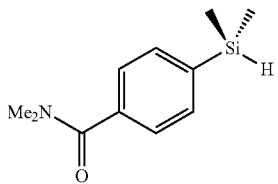

To a solution of dimethylamine hydrochloride (2.45 g, 30.0 mmol) in DCM (50 mL) was added triethylamine (4.2 mL, 30.0 mmol). The mixture was stirred for 30 minutes before the addition of 4-iodobenzoic acid (6.20 g, 25.0 mmol) and 1-(3-dimethylaminopropyl)-3-ethylcarbodiimide (EDC, 4.66 g, 30.0 mmol). The reaction was stirred for 8 hours at room temperature. Then the reaction mixture was washed with water (50 mL), HCl (aq., 1 M, 50 mL), NaHCO$_3$ (sat. aq., 50 mL), and brine (50 mL), then dried over MgSO$_4$ and concentrated under reduced pressure (50 torr). The crude product was dissolved in Et$_2$O (5 mL) and treated with hexane (50 mL). The target product 4-iodo-N,N-dimethylbenzamide (6.88 g, 25.0 mmol, quantitative) crashed out and was collected by filtration.

In a 100 mL round-bottom flask, 4-iodo-N,N-dimethylbenzamide (1.65 g, 6.0 mmol) in THF (15 mL) was cooled to −78° C. i-PrMgCl (6 mL, 2.0 M in Et$_2$O) was added dropwise slowly over 5 minutes. The resulting mixture was allowed to warm to −40° C. within 2 hours and maintained at −40° C. for another 2 hours before the dropwise addition of chlorodimethylsilane (1.3 mL, 12.0 mmol). The reaction was allowed to warm to room temperature and stirred for 8 hours. The reaction mixture was quenched with NH$_4$Cl (5 mL, sat. aq.) and the product was extracted with DCM (15 mL×3). The organic layer was washed with water (20 mL), then brine (20 mL), then dried over MgSO$_4$ and concentrated under reduced pressure (50 torr). The mixture was dissolved in Et$_2$O (5 mL) and treated with hexane (25 mL). Most of the starting material crashed out and was removed by filtration. The filtrate was collected, concentrated under reduced pressure, and then purified by silica column chromatography with EtOAc/hexane (1:2) to afford Compound 1h (0.12 g, 0.579 mmol, 10%). $^1$H NMR (400 MHz, CDCl$_3$) δ 7.57 (d, J=8.3 Hz, 2H), 7.39 (d, J=8.3 Hz, 2H), 4.43 (hept, J=3.8 Hz, 1H), 3.05 (s, 6H), 0.35 (d, J=3.7 Hz, 6H). $^{13}$C NMR (100 MHz, CDCl$_3$) δ 171.74, 139.53, 137.04, 134.11, 126.42, −3.74. HRMS (FAB) m/z: 208.1153 (M+H$^+$); calc. for C$_{11}$H$_{18}$ONSi: 208.1158.

(3,4-Dihydro-2H-pyran-6-yl)dimethylsilane (Compound 1i)

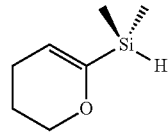

In a 100 mL round-bottom flask, 3,4-dihydro-2H-pyran (2.00 g, 24.0 mmol) in THF (1.0 mL) and pentane (40 mL) was cooled to −78° C. t-BuLi (15.5 mL, 1.7 M in pentane) was added dropwise slowly over 20 minutes. The resulting mixture was allowed to warm to 0° C. within 2 hours and maintained at 0° C. for another 2 hours before the dropwise addition of chlorodimethylsilane (2.6 mL, 24.0 mmol). The reaction was allowed to warm to room temperature and stirred for 8 hours. The reaction mixture was quenched with NH$_4$Cl (5 mL, sat. aq.) and the product was extracted with Et$_2$O (15 mL×3). The organic layer was washed with water (20 mL), then brine (20 mL), then dried over MgSO$_4$ and concentrated under reduced pressure (200 torr). The crude product was purified by silica column chromatography with Et$_2$O/pentane (1:30) to afford Compound 1i (2.80 g, 19.7 mmol, 82%). This compound is known (132). $^1$H NMR (400 MHz, CDCl$_3$) δ 5.09 (t, J=3.8 Hz, 1H), 4.05-3.91 (m, 3H), 2.04 (td, J=6.4, 3.8 Hz, 2H), 1.92-1.83 (m, 2H), 0.19 (d, J=3.8 Hz, 6H).

4-(Dimethylsilyl)phenol (Compound 1k)

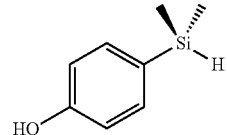

To a solution of 4-bromophenol (1.73 g, 10.0 mmol) in THF (15 mL) was added NaH (60% in mineral oil, 0.48 g, 12.0 mmol). After the mixture was stirred for 30 minutes, it was cooled down to −78° C. t-BuLi (6 mL, 1.7 M in pentane) was added dropwise slowly over 15 minutes. The resulting mixture was stirred at −78° C. for 2 hours before the dropwise addition of chlorodimethylsilane (2.3 mL, 21.0 mmol). The reaction was allowed to warm to room temperature and stirred for 8 hours. The reaction mixture was quenched with NH$_4$Cl (5 mL, sat. aq.) and the product was extracted with DCM (15 mL×3). The organic layer was washed with water (20 mL), then brine (20 mL), then dried over MgSO$_4$ and concentrated under reduced pressure (50 torr). The crude product was purified by silica column chromatography with EtOAc/hexane (1:7) to afford Compound 1k (0.60 g, 3.94 mmol, 39%). This compound is known (133). $^1$H NMR (400 MHz, CDCl$_3$) δ 7.43 (d, J=8.5 Hz, 2H), 6.85 (d, J=8.5 Hz, 2H), 4.78 (s, 1H), 4.40 (hept, J=3.7 Hz, 1H), 0.32 (d, J=3.8 Hz, 6H). $^{13}$C NMR (100 MHz, CDCl$_3$) δ 156.61, 135.82, 128.66, 115.16, −3.38.

(4-(Benzyloxy)phenyl)dimethylsilane (Compound 1ks)

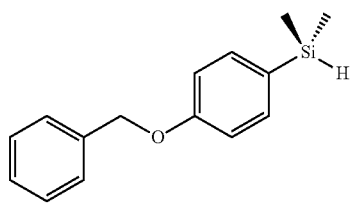

To a solution of 4-bromophenol (5.19 g, 30.0 mmol) in MeCN (50 mL) was added K$_2$CO$_3$ (5.53 g, 40.0 mmol). After the mixture was stirred at 40° C. for 30 minutes, BnBr (3.6 mL, 30.0 mmol) was added over 2 minutes. The resulting mixture was stirred at 40° C. for 3 hours. The reaction mixture was washed with water (20 mL), then brine (20 mL), then dried over MgSO$_4$ and concentrated under reduced pressure (50 torr) to afford the crude product 1-(benzyloxy)-4-bromobenzene (7.85 g, 30.0 mmol, quantitative).

In a 100 mL round-bottom flask, 1-(benzyloxy)-4-bromobenzene (6.57 g, 25.0 mmol) in THF (15 mL) was cooled to −78° C. t-BuLi (19.0 mL, 1.7 M in pentane) was added dropwise slowly over 15 minutes. The resulting mixture was stirred at −78° C. for 2 hours before the dropwise addition of chlorodimethylsilane (3.6 mL, 32.5 mmol). The reaction was allowed to warm to room temperature and stirred for 8 hours. The reaction mixture was quenched with NH$_4$Cl (5 mL, sat. aq.) and the product was extracted with Et$_2$O (15 mL×3). The organic layer was washed with water (20 mL), then brine (20 mL), then dried over MgSO$_4$ and concentrated under reduced pressure (50 torr). The crude product was purified by silica column chromatography with pentane to afford Compound 1ks (4.02 g, 16.6 mmol, 66%). $^1$H NMR (400 MHz, CDCl$_3$) δ 7.51-7.27 (m, 7H), 7.00 (d, J=8.6 Hz, 2H), 5.08 (s, 2H), 4.41 (hept, J=3.7 Hz, 1H), 0.32 (d, J=3.7 Hz, 6H). HRMS (FAB) m/z: 241.1053 ((M+H)—H$_2$+); calc. for C$_{15}$H$_{17}$O Si: 241.1049.

4-(Dimethylsilyl)aniline (Compound 23)

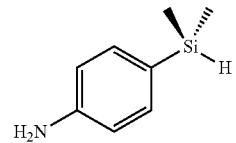

To a solution of 4-bromoaniline (3.44 g, 20.0 mmol) in DCM (30 mL) was added triethylamine (5.6 mL, 20.0 mmol) and N,N-dimethylpyridin-4-amine (DMAP, 244.3 mg, 2.0 mmol). After the mixture was stirred for 30 minutes, 1,2-bis(chlorodimethylsilyl)ethane (4.78 g, 20.0 mmol) was added in one portion. The reaction was stirred at 40° C. for 3 hours. The reaction mixture was filtrated through a pad of dry Celite quickly to remove the triethylamine hydrochloride. The resulting solution was concentrated under reduced pressure (50 torr) to afford the crude product 1-(4-bromophenyl)-2,2,5,5-tetramethyl-1,2,5-azadisilolidine. Note that this compound is moisture sensitive and decomposes on silica.

The crude 1-(4-bromophenyl)-2,2,5,5-tetramethyl-1,2,5-azadisilolidine in THF (30 mL) in a 100 mL round-bottom flask was cooled to −78° C. t-BuLi (17.6 mL, 1.7 M in pentane) was added dropwise slowly over 15 minutes. The resulting mixture was stirred at −78° C. for 2 hours before the dropwise addition of chlorodimethylsilane (3.3 mL, 30.0 mmol). The reaction was allowed to warm to room temperature and stirred for 8 hours. The reaction mixture was treated with Et$_2$O (50 mL) to allow the inorganic salts to crash out. The suspension was filtrated through a pad of Celite and basic alumina (1:1 mixture). The resulting solution was concentrated under reduced pressure (50 torr). The crude product was loaded on silica and allowed to sit for 15 minutes (for removal of the nitrogen protecting group), before purification by silica column chromatography with EtOAc/hexane (1:7) to afford Compound 23 (1.21 g, 8.00 mmol, 40%). This compound is known (134). $^1$H NMR (400 MHz, CDCl$_3$) δ 7.38 (d, J=8.4 Hz, 2H), 6.83 (d, J=8.4 Hz, 2H), 4.84 (s, 2H), 4.38 (hept, J=3.9 Hz, 1H), 0.30 (d, J=3.7 Hz, 6H). $^{13}$C NMR (100 MHz, CDCl$_3$) δ 144.82, 135.48, 127.64, 116.07, −3.38.

Benzyl (4-(dimethylsilyl)phenyl)carbamate (Compound 23s)

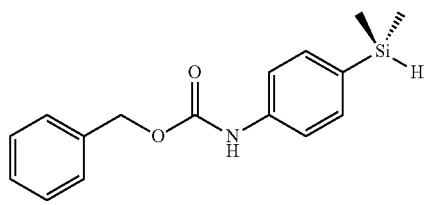

To a solution of 4-(dimethylsilyl)aniline (151.2 mg, 1.0 mmol) in DCM (3 mL) was added pyridine (162 μL, 2.0 mmol). After the mixture was stirred for 10 minutes, benzyl carbonochloridate (CbzCl, 170 μL, 1.2 mmol) was added in one portion. After stirring at room temperature overnight, the reaction mixture was washed with water (20 mL), then brine (20 mL), then dried over MgSO$_4$ and concentrated under reduced pressure (50 torr). The crude product was purified by silica column chromatography with EtOAc/hexane (1:7) to afford Compound 23s (130.4 mg, 0.457 mmol, 46%). $^1$H NMR (400 MHz, CDCl$_3$) δ 7.50 (d, J=8.4 Hz, 2H), 7.46-7.33 (m, 5H), 6.68 (s, 1H), 5.23 (s, 2H), 4.42 (hept, J=3.7 Hz, 1H), 0.34 (d, J=3.7 Hz, 6H). HRMS (FAB) m/z: 286.1274 (M+H$^+$); calc. for C$_{16}$H$_{20}$O$_2$NSi: 286.1263.

(4-Ethynylphenyl)dimethylsilane (Compound 1m)

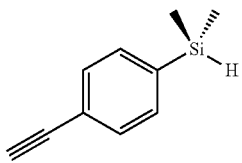

A solution of ((4-bromophenyl)ethynyl)trimethylsilane (5.06 g, 20.0 mmol) and K$_2$CO$_3$ (5.53 g, 40.0 mmol) in MeOH (40 mL) was stirred at room temperature for 4 hours. MeOH was removed under reduced pressure, and the crude product was washed with water (30 mL) and extracted with Et$_2$O (40 mL). The organic layer was dried over MgSO$_4$, filtrated through a pad of silica, and concentrated under reduced pressure to afford the product 1-bromo-4-ethynylbenzene (3.21 g, 17.7 mmol, 89%).

In a 100 mL round-bottom flask, 1-bromo-4-ethynylbenzene (1.81 g, 10.0 mmol) in THF (15 mL) was cooled to −78° C. n-BuLi (8.0 mL, 2.5 M in hexane) was added dropwise very slowly over 30 minutes. The resulting mixture was stirred at −78° C. for 2 hours before the dropwise addition of a solution of chlorodimethylsilane (1.1 mL, 10.0 mmol) in THF (20 mL). The reaction was allowed to warm to room temperature and stirred for 8 hours. The reaction mixture was quenched with NH$_4$Cl (5 mL, sat. aq.) and the product was extracted with Et$_2$O (15 mL×3). The organic layer was washed with water (20 mL), then brine (20 mL), then dried over MgSO$_4$ and concentrated under reduced pressure (200 torr). The crude product was purified by distillation under reduced pressure (1.4 torr) at 45° C. (1.12 g, 6.99 mmol, 70%). This compound is known (135). $^1$H NMR (400 MHz, CDCl$_3$) δ 7.49 (d, J=3.9 Hz, 4H), 4.42 (hept, J=3.8 Hz, 1H), 3.10 (s, 1H), 0.34 (d, J=3.8 Hz, 6H). $^{13}$C NMR (100 MHz, CDCl$_3$) δ 138.83, 134.01, 131.43, 122.91, 83.81, 77.85, −3.77.

Dimethyl(4-vinylphenyl)silane (Compound 1n)

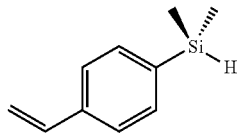

In a 100 mL round-bottom flask, 1-bromo-4-vinylbenzene (1.83 g, 10.0 mmol) in THF (15 mL) was cooled to −78° C. n-BuLi (7.5 mL, 1.6 M in hexane) was added dropwise very slowly over 30 minutes. The resulting mixture was stirred at −78° C. for 2 hours before the dropwise addition of a solution of chlorodimethylsilane (1.1 mL, 10.0 mmol) in THF (20 mL). The reaction was allowed to warm to room temperature and stirred for 8 hours. The reaction mixture was quenched with NH$_4$Cl (5 mL, sat. aq.) and the product was extracted with Et$_2$O (15 mL×3). The organic layer was washed with water (20 mL), then brine (20 mL), then dried over MgSO$_4$ and concentrated under reduced pressure (200 torr). The crude product was purified by silica column chromatography with pentane to afford In (1.29 g, 7.95 mmol, 80%). This compound is known (136). $^1$H NMR (400 MHz, CDCl$_3$) δ 7.51 (d, J=8.1 Hz, 2H), 7.41 (d, J=7.9 Hz, 2H), 6.72 (dd, J=17.6, 10.9 Hz, 1H), 5.79 (dd, J=17.6, 0.9 Hz, 1H), 5.27 (dd, J=10.9, 0.9 Hz, 1H), 4.43 (hept, J=3.7 Hz, 1H), 0.35 (d, J=3.8 Hz, 6H).

Cyclohexa-2,5-dien-1-yldimethylsilane (Compound 1o)

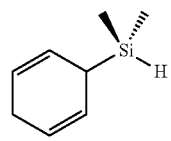

In a 100 mL round-bottom flask, cyclohexa-1,4-diene (2.3 mL, 24.0 mmol) in THF (20 mL) was cooled to −78° C. t-BuLi (15.5 mL, 1.7 M in pentane) and N,N,N',N'-tetramethylethane-1,2-diamine (TMEDA, 3.6 mL, 24 mmol) were added simultaneously as separate solutions, dropwise over 20 minutes. The resulting mixture was allowed to warm to −45° C. in 30 min and maintained at −45° C. for another 1 hour before the dropwise addition of chlorodimethylsilane (2.6 mL, 24.0 mmol). The reaction was allowed to warm to room temperature and stirred for 1.5 hours. The reaction mixture was quenched with NH$_4$Cl (5 mL, sat. aq.) and the product was extracted with Et$_2$O (15 mL×3). The organic layer was washed with water (20 mL), then brine (20 mL), then dried over MgSO$_4$ and concentrated under reduced pressure (300 torr). The crude product was purified by silica column chromatography with pentane to afford Compound 1o (1.24 g, 8.97 mmol, 38%). (Note: this compound is oxygen sensitive and very volatile; storage under argon at −20° C. is recommended.) This compound is known (137). $^1$H NMR (400 MHz, CDCl$_3$) δ 5.72-5.64 (m, 2H), 5.61-5.54 (m, 2H), 3.85 (heptd, J=3.5, 1.6 Hz, 1H), 2.80-2.60 (m, 2H), 2.42-2.30 (m, 1H), 0.10 (d, J=3.7 Hz, 6H). $^{13}$C NMR (100 MHz, CDCl$_3$) δ 125.91, 122.09, 29.38, 26.50, −6.31.

Dimethyl(naphthalen-2-yl)silane (Compound 1p)

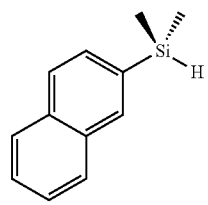

In a 100 mL round-bottom flask, 2-bromonaphthalene (2.07 g, 10.0 mmol) in THF (15 mL) was cooled to −78° C. n-BuLi (7.5 mL, 1.6 M in hexane) was added dropwise very slowly over 30 minutes. The resulting mixture was stirred at −78° C. for 2 hours before the dropwise addition of a solution of chlorodimethylsilane (1.1 mL, 10.0 mmol) in THF (20 mL). The reaction was allowed to warm to room temperature and stirred for 8 hours. The reaction mixture was quenched with NH$_4$Cl (5 mL, sat. aq.) and the product was extracted with Et$_2$O (15 mL×3). The organic layer was washed with water (20 mL), then brine (20 mL), then dried over MgSO$_4$ and concentrated under reduced pressure (100 torr). The crude product was purified by silica column chromatography with pentane to afford Compound 1p (1.69 g, 9.07 mmol, 91%). This compound is known (138). $^1$H NMR (400 MHz, CDCl$_3$) δ 8.05 (s, 1H), 7.87-7.82 (m, 3H), 7.61 (dd, J=8.1, 1.0 Hz, 1H), 7.51-7.48 (m, 2H), 4.56 (hept, J=3.8 Hz, 1H), 0.43 (d, J=3.8 Hz, 6H).

Benzofuran-2-yldimethylsilane (Compound 1q)

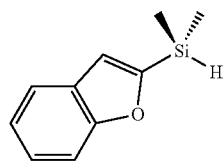

In a 100 mL round-bottom flask, benzofuran (1.18 g, 10.0 mmol) in THF (15 mL) was cooled to −78° C. n-BuLi (7.5 mL, 1.6 M in hexane) was added dropwise slowly over 20 minutes. The resulting mixture was allowed to warm to −40° C. within 1 hour and maintained at −40° C. for another 2 hours before the dropwise addition of chlorodimethylsilane (1.1 mL, 10.0 mmol). The reaction was allowed to warm to room temperature and stirred for 8 hours. The reaction mixture was quenched with NH$_4$Cl (5 mL, sat. aq.) and the product was extracted with Et$_2$O (15 mL×3). The organic layer was washed with water (20 mL), then brine (20 mL), then dried over MgSO$_4$ and concentrated under reduced pressure (100 torr). The crude product was purified by silica column chromatography with Et$_2$O/pentane (1:30) to afford Compound 1q (1.08 g, 6.13 mmol, 61%). This compound is known (139). $^1$H NMR (400 MHz, CDCl$_3$) δ 7.59 (ddd, J=7.1, 1.3, 0.7 Hz, 1H,), 7.52 (dd, J=8.5, 0.5 Hz, 1H), 7.30 (ddd, J=8.5, 7.5, 1.0 Hz, 1H), 7.22 (ddd, J=7.5, 7.5, 1.0 Hz, 1H), 7.04 (d, J=0.7 Hz, 1H), 4.52 (hept, J=3.8 Hz, 1H), 0.44 (d, J=3.8 Hz, 6H).

Benzothiophen-2-yldimethylsilane (Compound 1r)

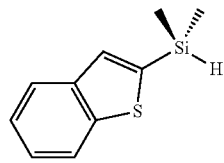

In a 100 mL round-bottom flask, benzothiophene (1.34 g, 10.0 mmol) in THF (15 mL) was cooled to −78° C. n-BuLi (7.5 mL, 1.6 M in hexane) was added dropwise slowly over 20 minutes. The resulting mixture was allowed to warm to −40° C. within 1 hour and maintained at −40° C. for another 2 hours before the dropwise addition of chlorodimethylsilane (1.1 mL, 10.0 mmol). The reaction was allowed to warm to room temperature and stirred for 8 hours. The reaction mixture was quenched with NH$_4$Cl (5 mL, sat. aq.) and the product was extracted with Et$_2$O (15 mL×3). The organic layer was washed with water (20 mL), then brine (20 mL), then dried over MgSO$_4$ and concentrated under reduced pressure (100 torr). The crude product was purified by silica column chromatography with pentane to afford Compound 1r (1.76 g, 9.14 mmol, 91%). $^1$H NMR (400 MHz, CDCl$_3$) δ 7.92-7.86 (m, 1H), 7.86-7.79 (m, 1H), 7.53 (s, 1H), 7.38-7.30 (m, 2H), 4.63 (hept, J=3.7 Hz, 1H), 0.46 (d, J=3.7 Hz, 6H). $^{13}$C NMR (100 MHz, CDCl$_3$) δ 143.87, 141.08, 138.57, 132.18, 124.47, 124.20, 123.63, 122.32, −2.93. HRMS (FAB) m/z: 191.0354 (M−H$^-$); calc. for C$_{10}$H$_{12}$SSi: 191.0351.

Synthesis and Characterization of Authentic Organosilicon Products

Racemic standard references of organosilicon products were prepared using rhodium-catalyzed Si—H insertion reactions, following the general procedure described below as follows.

General Procedure for Rhodium-Catalyzed Si—H Insertion

To a 20 mL vial or 25 mL flask was added silane (1.0 mmol, 1.0 equiv.), Rh$_2$(OAc)$_4$ (4.4 mg, 1 mol %) and DCM (5 mL). The mixture was cooled to −78° C., after which diazo compound (1.0 mmol, 1.0 equiv.) was added dropwise to the solution. The reaction was allowed to slowly warm up to room temperature in 8 hours and stirred at room temperature for another 4 hours. Evaporation of the organic solvent and purification by silica column chromatography using EtOAc and hexane as eluents afforded organosilicon Compounds 3-20 in 20-70% yields.

Organosilicon compounds 21 and 22 were prepared by rhodium-catalyzed Si—H insertion between Me-EDA and the corresponding 0- or N-protected silane (Compounds 1 ks and 23s, respectively) to give Compounds 21a and 22a, followed by deprotection under standard palladium-catalyzed hydrogenation condition (10% Pd/C in ethanol under H$_2$ atmosphere at room temperature for 16 hours). The hydrogenation reaction afforded Compounds 21 and 22 in 96% and 88% yield, respectively. The chemical structures and NMR data for Compounds 3-20, 21a, 21, 22, and 22 are shown below:

Ethyl 2-(dimethyl(phenyl)silyl)propanoate (Compound 3)

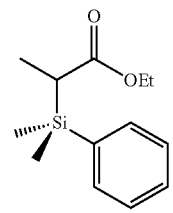

$^1$H NMR (400 MHz, CDCl$_3$) δ 7.55-7.46 (m, 2H), 7.43-7.32 (m, 3H), 4.02 (q, J=7.1 Hz, 2H), 2.25 (q, J=7.1 Hz, 1H), 1.17-1.11 (m, 6H), 0.37 (d, J=0.6 Hz, 6H). $^{13}$C NMR (100 MHz, CDCl$_3$) δ 176.13, 136.42, 133.99, 129.57, 127.92, 59.96, 30.14, 14.43, 11.42, −3.92, −4.77. HRMS (FAB) m/z: 236.1234 (M$^+$); calc. for C$_{13}$H$_{20}$O$_2$Si: 236.1233.

Ethyl 2-(dimethyl(p-tolyl)silyl)propanoate (Compound 4)

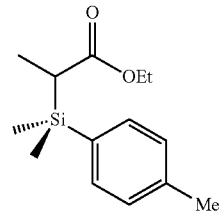

$^1$H NMR (400 MHz, CDCl$_3$) δ 7.40 (d, J=7.9 Hz, 2H), 7.18 (d, J=7.5 Hz, 2H), 4.03 (q, J=7.1 Hz, 2H), 2.35 (s, 3H), 2.24 (q, J=7.1 Hz, 1H), 1.19-1.11 (m, 6H), 0.35 (d, J=0.4 Hz, 6H). $^{13}$C NMR (100 MHz, CDCl$_3$) δ 176.21, 139.51, 134.04, 132.72, 128.77, 59.94, 30.22, 21.63, 14.47, 11.44, −3.75, −4.75. $^{29}$Si NMR (79 MHz, CDCl$_3$) δ 0.19. HRMS (FAB) m/z: 250.1391 (M$^+$); calc. for C$_{14}$H$_{22}$O$_2$Si: 250.1389.

Ethyl 2-(dimethyl(4-methoxyphenyl)silyl)propanoate (Compound 5)

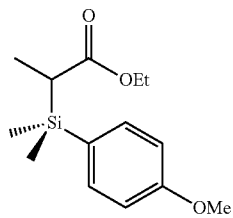

$^1$H NMR (400 MHz, CDCl$_3$) δ 7.43 (d, J=8.6 Hz, 2H), 6.91 (d, J=8.6 Hz, 2H), 4.03 (q, J=7.1 Hz, 2H), 3.81 (s, 3H), 2.22 (q, J=7.1 Hz, 1H), 1.20-1.10 (m, 6H), 0.35 (s, 6H). $^{13}$C NMR (100 MHz, CDCl$_3$) δ 176.24, 160.84, 135.49, 127.18, 113.70, 59.93, 55.18, 30.37, 14.49, 11.45, −3.72, −4.58. $^{29}$Si NMR (79 MHz, CDCl$_3$) δ −0.10. HRMS (FAB) m/z: 266.1332 (M$^+$); calc. for C$_{14}$H$_{22}$O$_3$Si: 266.1338.

Ethyl 2-(dimethyl(4-chlorophenyl)silyl)propanoate (Compound 6)

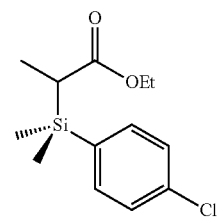

$^1$H NMR (400 MHz, CDCl$_3$) δ 7.43 (d, J=8.4 Hz, 2H), 7.34 (d, J=8.3, 1.9 Hz, 2H), 4.02 (q, J=7.1 Hz, 2H), 2.23 (q, J=7.1 Hz, 1H), 1.17-1.11 (m, 6H), 0.36 (s, 6H). $^{13}$C NMR (100 MHz, CDCl$_3$) δ 175.87, 135.98, 135.36, 134.75, 128.19, 60.06, 30.03, 14.45, 11.38, −4.02, −4.61. $^{29}$Si NMR (79 MHz, CDCl$_3$) δ 0.59. HRMS (FAB) m/z: 270.0847 (M$^+$); calc. for C$_{13}$H$_{19}$O$_2$SiCl: 270.0843.

Ethyl 2-(dimethyl(4-trifluoromethylphenyl)silyl)propanoate (Compound 7)

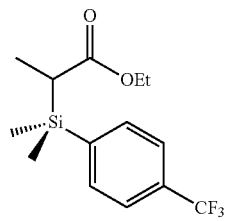

$^1$H NMR (400 MHz, CDCl$_3$) δ 7.61 (d, J=8.4 Hz, 4H), 4.01 (qd, J=7.2, 0.7 Hz, 2H), 2.27 (q, J=7.2 Hz, 1H), 1.16 (d, J=7.2 Hz, 3H), 1.12 (t, J=7.1 Hz, 3H), 0.40 (d, J=1.3 Hz, 6H). $^{13}$C NMR (100 MHz, CDCl$_3$) δ 141.49, 134.32, 131.52 (q, J$_{C-F}$=32.3 Hz), 124.26 (q, J$_{C-F}$=272.2 Hz), 124.43 (q, J$_{C-F}$=3.8 Hz), 60.16, 29.96, 14.39, 11.39, −4.18, −4.65. $^{29}$Si NMR (79 MHz, CDCl$_3$) δ 1.01. HRMS (FAB) m/z: 304.1119 (M$^+$); calc. for C$_{14}$H$_{19}$O$_2$SiF$_3$: 304.1106.

Ethyl 2-(dimethyl(4-chloromethylphenyl)silyl)propanoate (Compound 8)

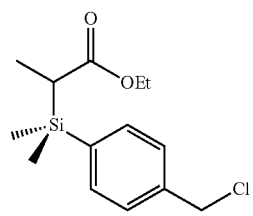

$^1$H NMR (400 MHz, CDCl$_3$) δ 7.51 (d, J=8.0 Hz, 2H), 7.38 (d, J=7.9 Hz, 2H), 4.58 (s, 2H), 4.02 (q, J=7.1 Hz, 2H), 2.25 (q, J=7.1 Hz, 1H), 1.18-1.08 (m, 6H), 0.37 (d, J=1.2 Hz, 6H). $^{13}$C NMR (100 MHz, CDCl$_3$) δ 175.98, 138.72, 136.92, 134.44, 128.02, 60.02, 46.23, 30.05, 14.44, 11.41, −3.97, −4.70. $^{29}$Si NMR (79 MHz, CDCl$_3$) δ 0.59. HRMS (FAB) m/z: 283.0927 ((M+H)−H$_2^+$); calc. for C$_{14}$H$_{20}$O$_2$SiCl: 283.0921.

Methyl 4-((1-ethoxy-1-oxopropan-2-yl)dimethylsilyl)benzoate (Compound 9)

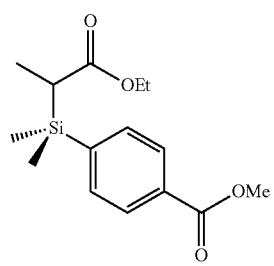

$^1$H NMR (400 MHz, CDCl$_3$) δ 8.00 (d, J=8.3 Hz, 2H), 7.58 (d, J=8.3 Hz, 2H), 4.01 (qd, J=7.1, 0.9 Hz, 2H), 3.92 (s, 3H), 2.27 (q, J=7.2 Hz, 1H), 1.19-1.05 (m, 6H), 0.39 (d,

Ethyl 2-((4-(dimethylcarbamoyl)phenyl)dimethylsilyl)propanoate (Compound 10)

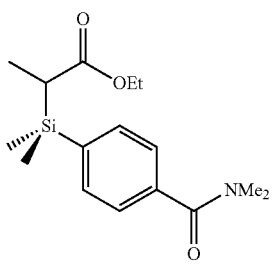

¹H NMR (400 MHz, CDCl₃) δ 7.54 (d, J=8.0 Hz, 2H), 7.39 (d, J=8.0 Hz, 2H), 4.03 (q, J=7.1 Hz, 2H), 3.11 (s, 3H), 2.97 (s, 3H), 2.26 (q, J=7.2 Hz, 1H), 1.20-1.10 (m, 6H), 0.37 (s, 6H). ¹³C NMR (100 MHz, CDCl₃) δ 175.94, 171.59, 138.39, 137.38, 134.01, 126.37, 60.05, 39.67, 35.45, 29.95, 14.49, 11.41, −3.92, −4.75. HRMS (FAB) m/z: 308.1689 (M+H⁺); calc. for C₁₆H₂₆NO₃Si: 308.1682.

Ethyl 2-((naphthalen-2-yl)dimethylsilyl)propanoate (Compound 11)

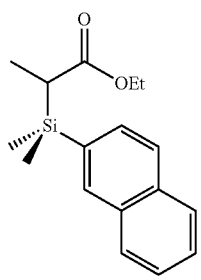

¹H NMR (400 MHz, CDCl₃) δ 8.00 (s, 1H), 7.87-7.80 (m, 3H), 7.57 (dd, J=8.2, 0.8 Hz, 1H), 7.53-7.46 (m, 2H), 4.02 (q, J=7.1 Hz, 2H), 2.34 (q, J=7.1 Hz, 1H), 1.18 (d, J=7.1 Hz, 3H), 1.11 (t, J=7.1 Hz, 3H), 0.46 (d, J=2.0 Hz, 6H). ¹³C NMR (100 MHz, CDCl₃) δ 176.14, 134.88, 133.99, 133.92, 132.92, 130.03, 128.23, 127.84, 127.16, 126.70, 126.15, 60.01, 30.18, 14.44, 11.50, −3.76, −4.71. ²⁹Si NMR (79 MHz, CDCl₃) δ 0.76. HRMS (FAB) m/z: 286.1395 (M⁺); calc. for C₁₇H₂₂O₂Si: 286.1389.

Ethyl 2-((benzofuran-2-yl)dimethylsilyl)propanoate (Compound 12)

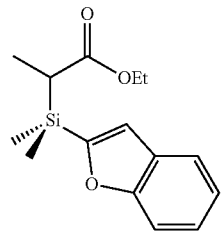

¹H NMR (400 MHz, CDCl₃) δ 7.58 (ddd, J=7.7, 1.3, 0.7 Hz, 1H), 7.50 (dd, J=8.2, 0.9 Hz, 1H), 7.29 (ddd, J=8.4, 7.2, 1.4 Hz, 1H), 7.21 (ddd, J=8.2, 7.8, 1.0 Hz, 1H), 7.05 (d, J=1.0 Hz, 1H), 4.07 (qd, J=7.2, 1.2 Hz, 2H), 2.38 (q, J=7.2 Hz, 1H), 1.24 (d, J=7.1 Hz, 3H), 1.14 (t, J=7.1 Hz, 3H), 0.44 (d, J=1.9 Hz, 6H). ¹³C NMR (100 MHz, CDCl₃) δ 175.57, 159.85, 158.31, 127.82, 124.84, 122.58, 121.29, 117.93, 111.48, 60.22, 29.42, 14.42, 11.24, −4.32, −5.05. ²⁹Si NMR (79 MHz, CDCl₃) δ −5.09. HRMS (FAB) m/z: 276.1182 (M⁺); calc. for C₁₅H₂₀O₃Si: 276.1169.

Ethyl 2-(benzothiophen-2-yldimethylsilyl)propanoate (Compound 13)

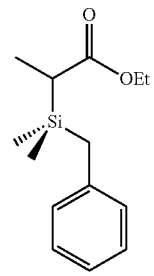

¹H NMR (400 MHz, CDCl₃) δ 7.93-7.85 (m, 1H), 7.85-7.79 (m, 1H), 7.52 (d, J=0.8 Hz, 1H), 7.39-7.30 (m, 2H), 4.08 (qd, J=7.1, 1.1 Hz, 2H), 2.33 (q, J=7.2 Hz, 1H), 1.24 (d, J=7.2 Hz, 3H), 1.17 (t, J=7.1 Hz, 3H), 0.47 (d, J=0.9 Hz, 6H). ¹³C NMR (100 MHz, CDCl₃) δ 175.61, 143.84, 140.93, 137.78, 132.56, 124.64, 124.25, 123.75, 122.30, 60.24, 30.46, 14.47, 11.43, −2.77, −3.64. ²⁹Si NMR (79 MHz, CDCl₃) δ −1.51. HRMS (FAB) m/z: 292.0963 (M⁺); calc. for C₁₅H₂₀O₂SiS: 292.0953.

Ethyl 2-(benzyldimethylsilyl)propanoate (Compound 14)

¹H NMR (400 MHz, CDCl₃) δ 7.25-7.17 (m, 2H), 7.11-7.06 (m, 1H), 7.06-6.96 (m, 2H), 4.24-4.02 (m, 2H), 2.24-2.14 (m, 2H), 2.10 (q, J=7.1 Hz, 1H), 1.26 (t, J=7.1 Hz, 3H), 1.19 (d, J=7.1 Hz, 3H), 0.06--0.12 (m, J=0.5 Hz, 6H). ¹³C NMR (100 MHz, CDCl₃) δ 176.19, 139.25, 128.44, 128.42, 124.44, 60.04, 28.95, 24.03, 14.66, 11.17, −4.76, −4.82. ²⁹Si NMR (79 MHz, CDCl₃) δ 5.96. HRMS (FAB) m/z: 251.1459 (M+H⁺); calc. for C₁₄H₂₃O₂Si: 251.1467.

Ethyl
2-(cyclohexa-2,5-dien-1-yldimethylsilyl)propanoate
(Compound 15)

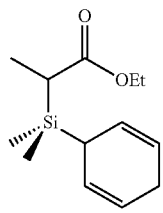

¹H NMR (400 MHz, CDCl₃) δ 5.81-5.52 (m, 4H), 4.17-4.05 (m, 2H), 2.81-2.56 (m, 2H), 2.48-2.36 (m, 1H), 2.19 (q, J=7.1 Hz, 1H), 1.24 (t, J=7.1 Hz, 3H), 1.21 (d, J=7.2 Hz, 3H), 0.08 (d, J=4.4 Hz, 6H). ¹³C NMR (100 MHz, CDCl₃) δ 176.24, 125.63, 125.53, 122.65, 122.52, 60.05, 29.47, 28.28, 26.52, 14.59, 11.33, −6.35, −6.70. HRMS (FAB) m/z: 237.1313 ((M+H)—H₂⁺); calc. for C₁₃H₂₁O₂Si: 237.1311.

Ethyl 2-((4-ethynylphenyl)dimethylsilyl)butanoate
(Compound 16)

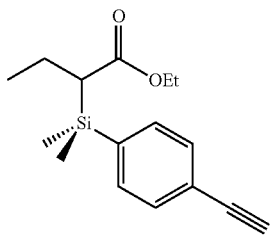

¹H NMR (400 MHz, CDCl₃) δ 7.53-7.42 (m, 4H), 4.13-3.93 (m, 2H), 3.11 (s, 1H), 2.08 (dd, J=11.7, 3.1 Hz, 1H), 1.78 (ddq, J=14.2, 11.7, 7.1 Hz, 1H), 1.40 (dqd, J=13.8, 7.3, 3.1 Hz, 1H), 1.13 (t, J=7.1 Hz, 3H), 0.89 (t, J=7.2 Hz, 3H), 0.35 (d, J=4.1 Hz, 6H). ¹³C NMR (100 MHz, CDCl₃) δ 175.05, 137.86, 133.87, 131.36, 123.17, 83.71, 78.06, 59.95, 39.53, 20.60, 15.13, 14.47, −3.96, −4.56. HRMS (FAB) m/z: 273.1316 ((M+H)—H₂⁺); calc. for C₁₆H₂₁O₂Si: 273.1311.

Isopropyl
2-((4-ethynylphenyl)dimethylsilyl)propanoate
(Compound 17)

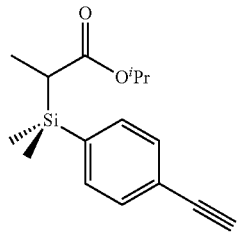

¹H NMR (400 MHz, CDCl₃) δ 7.47 (app s, 4H), 4.91 (hept, J=6.3 Hz, 1H), 3.11 (s, 1H), 2.21 (q, J=7.1 Hz, 1H), 1.16 (d, J=6.3 Hz, 3H), 1.13 (d, J=7.2 Hz, 3H), 1.08 (d, J=6.3 Hz, 3H), 0.36 (d, J=3.0 Hz, 6H). ¹³C NMR (100 MHz, CDCl₃) δ 175.39, 137.82, 133.93, 131.36, 123.15, 83.73, 78.03, 67.33, 30.02, 22.16, 22.01, 11.45, −3.95, −4.69. HRMS (FAB) m/z: 275.1479 (M+H⁺); calc. for C₁₆H₂₃O₂Si: 275.1467.

Ethyl 2-((3,4-dihydro-2H-pyran-6-yl)dimethylsilyl)
propanoate (Compound 18)

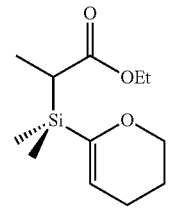

¹H NMR (400 MHz, CDCl₃) δ 5.02 (t, J=3.8, 1H), 4.16-4.02 (m, 2H), 3.90 (dd, J=5.8, 4.9 Hz, 2H), 2.17 (q, J=7.1 Hz, 1H), 2.05-1.98 (m, 2H), 1.87-1.78 (m, 2H), 1.23 (t, J=7.1 Hz, 3H), 1.18 (d, J=7.1 Hz, 3H), 0.14 (d, J=8.6 Hz, 6H). ¹³C NMR (100 MHz, CDCl₃) δ 176.26, 157.26, 112.83, 65.77, 59.91, 28.78, 22.79, 20.90, 14.61, 11.24, −4.96, −5.98. ²⁹Si NMR (79 MHz, CDCl₃) δ −4.02. HRMS (FAB) m/z: 243.1410 (M+H⁺); calc. for C₁₂H₂₃O₃Si: 243.1417.

Ethyl 2-((4-vinylphenyl)dimethylsilyl)propanoate
(Compound 19)

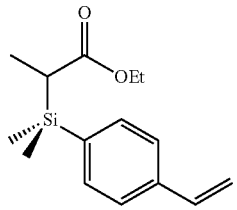

¹H NMR (400 MHz, CDCl₃) δ 7.47 (d, J=8.1 Hz, 2H), 7.40 (d, J=8.0 Hz, 2H), 6.71 (dd, J=17.6, 10.9 Hz, 1H), 5.79 (dd, J=17.6, 0.9 Hz, 1H), 5.27 (dd, J=10.9, 1.0 Hz, 1H), 4.03 (q, J=7.1 Hz, 2H), 2.25 (q, J=7.1 Hz, 1H), 1.16-1.13 (m, 6H), 0.37 (s, 6H). $^{13}$C NMR (100 MHz, CDCl$_3$) δ 176.09, 138.68, 136.85, 136.00, 134.26, 125.69, 114.65, 59.99, 30.14, 14.46, 11.42, −3.87, −4.75. $^{29}$Si NMR (79 MHz, CDCl$_3$) δ 0.26. HRMS (FAB) m/z: 262.1384 (M$^+$); calc. for C$_{15}$H$_{22}$O$_2$Si: 262.1389.

Ethyl 2-((4-ethynylphenyl)dimethylsilyl)propanoate (Compound 20)

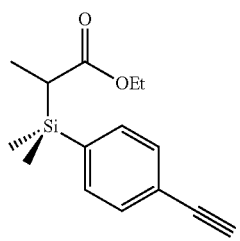

$^1$H NMR (400 MHz, CDCl$_3$) δ 7.50-7.44 (m, 4H), 4.01 (qd, J=7.2, 0.6 Hz, 2H), 3.11 (s, 1H), 2.24 (q, J=7.1 Hz, 1H), 1.17-1.10 (m, 6H), 0.37 (d, J=0.7 Hz, 6H). $^{13}$C NMR (100 MHz, CDCl$_3$) δ 175.89, 137.69, 133.87, 131.36, 123.20, 83.70, 78.08, 60.04, 29.98, 14.44, 11.38, −4.10, −4.75. $^{29}$Si NMR (79 MHz, CDCl$_3$) δ 0.79. HRMS (FAB) m/z: 259.1153 ((M+H)—H$_2$$^+$); calc. for C$_{15}$H$_{19}$O$_2$Si: 259.1154.

Ethyl 2-((4-(benzyloxy)phenyl)dimethylsilyl)propanoate (Compound 21a)

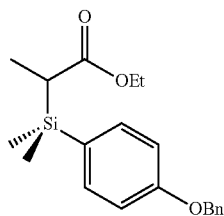

$^1$H NMR (400 MHz, CDCl$_3$) δ 7.46-7.30 (m, 7H), 7.05-6.93 (m, 2H), 5.08 (s, 2H), 4.02 (q, J=7.1 Hz, 2H), 2.22 (q, J=7.1 Hz, 1H), 1.20-1.10 (m, 6H), 0.35 (s, 6H). $^{13}$C NMR (100 MHz, CDCl$_3$) δ 176.22, 160.07, 137.01, 135.51, 128.74, 128.13, 127.61, 127.52, 114.56, 69.87, 59.93, 30.35, 14.48, 11.45, −3.75, −4.57. HRMS (FAB) m/z: 342.1665 (M$^+$); calc. for C$_{20}$H$_{26}$O$_3$Si: 342.1651.

Ethyl 2-((4-hydroxyphenyl)dimethylsilyl)propanoate (Compound 21)

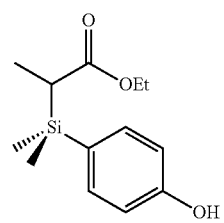

$^1$H NMR (400 MHz, CDCl$_3$) δ 7.36 (d, J=8.5 Hz, 2H), 6.81 (d, J=8.6 Hz, 2H), 5.49 (s, 1H), 4.03 (qd, J=7.1, 0.6 Hz, 2H), 2.23 (q, J=7.1 Hz, 1H), 1.19-1.12 (m, 6H), 0.35 (d, J=1.2 Hz, 6H). $^{13}$C NMR (100 MHz, CDCl$_3$) δ 176.67, 157.18, 135.68, 126.90, 115.16, 60.12, 30.51, 14.46, 11.43, −3.83, −4.33. HRMS (FAB) m/z: 252.1175 (M$^+$); calc. for C$_{13}$H$_{20}$O$_3$Si: 252.1182.

Ethyl 2-((4-(((benzyloxy)carbonyl)amino)phenyl)dimethylsilyl)propanoate (Compound 22a)

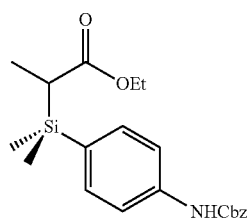

$^1$H NMR (400 MHz, CDCl$_3$) δ 7.49-7.30 (m, 9H), 6.70 (s, 1H), 5.20 (s, 2H), 4.02 (q, J=7.1 Hz, 2H), 2.22 (q, J=7.1 Hz, 1H), 1.18-1.10 (m, 6H), 0.35 (s, 6H). $^{13}$C NMR (100 MHz, CDCl$_3$) δ 176.13, 153.24, 139.07, 136.06, 134.98, 130.78, 128.78, 128.56, 128.48, 117.96, 67.24, 59.98, 30.21, 14.49, 11.41, −3.83, −4.68. HRMS (FAB) m/z: 385.1710 (M$^+$); calc. for C$_{21}$H$_{27}$NO$_4$Si: 385.1709.

Ethyl 2-((4-aminophenyl)dimethylsilyl)propanoate (Compound 22)

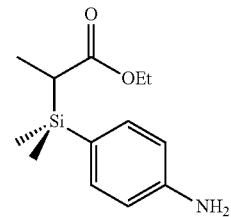

$^1$H NMR (400 MHz, CDCl$_3$) δ 7.29 (d, J=8.4 Hz, 2H), 6.70 (d, J=8.4 Hz, 2H), 4.03 (q, J=7.1 Hz, 2H), 3.64 (br s, 2H), 2.20 (q, J=7.1 Hz, 1H), 1.16 (t, J=7.1 Hz, 3H), 1.13 (d, J=7.1 Hz, 3H), 0.32 (s, 6H). $^{13}$C NMR (100 MHz, CDCl$_3$) δ 176.40, 147.40, 135.32, 124.37, 114.82, 59.87, 30.47, 14.48, 11.44, −3.68, −4.68. HRMS (FAB) m/z: 251.1339 (M$^+$); calc. for C$_{13}$H$_{21}$NO$_2$Si: 251.1342. $[\alpha_D]^{25}$=+46.1 (c 0.505 in cyclohexane, 98% ee).

Preparative-Scale Whole-Cell Biocatalytic Reaction

Figure 14A:
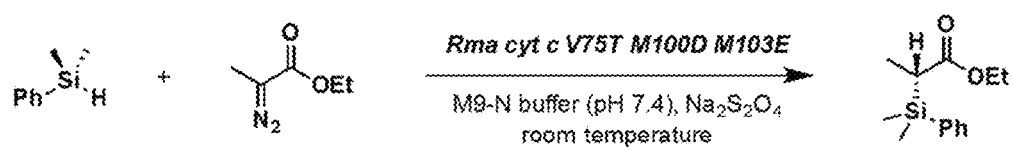
FIGS. 14A and 14B show an example of a reaction time course of a purified Rma cyt c M100D V75T M103E-catalyzed reaction between phenyldimethylsilane and Me-EDA.
Figure 14B:
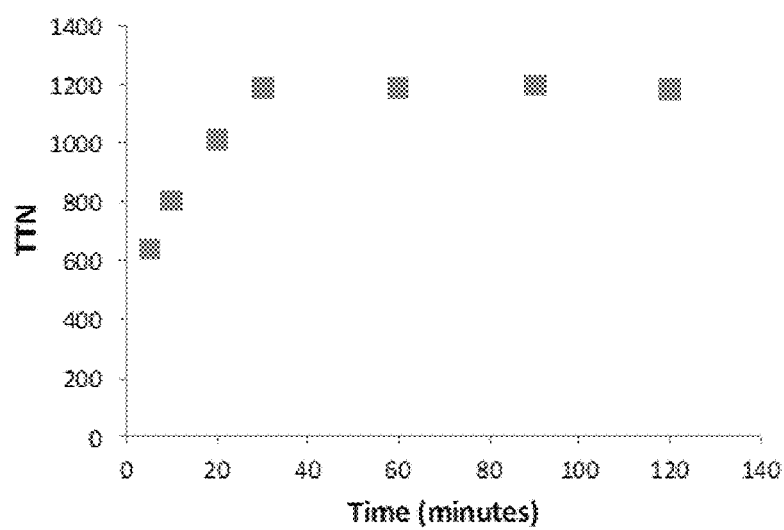
Figure 15:
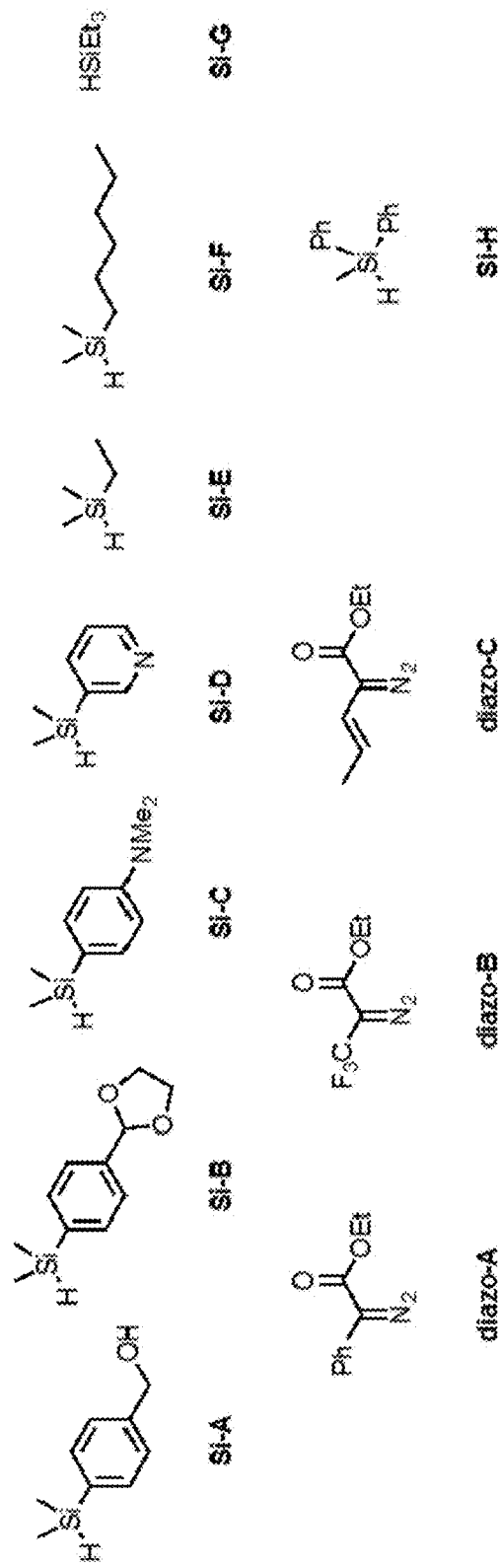
FIG. 15 shows additional substrates that were tested for Rma cyt c V75T M100D M103E-catalyzed carbon-silicon bond formation. Rma cyt c V75T M100D M103E-catalyzed reactions of silanes (Compounds Si-A-H) were tested with Me-EDA and that of diazo compounds (Compounds diazo-A-C) were tested with phenyldimethylsilane under standard in vitro biocatalytic reaction conditions. Product formation was analyzed by GC-MS. For Compounds Si-A-D and diazo-A, formation of organosilicon product was detected by GC-MS. For Compounds Si-E-H and diazo-B-C, formation of organosilicon product was not detected by GC-MS.
Figure 16A:
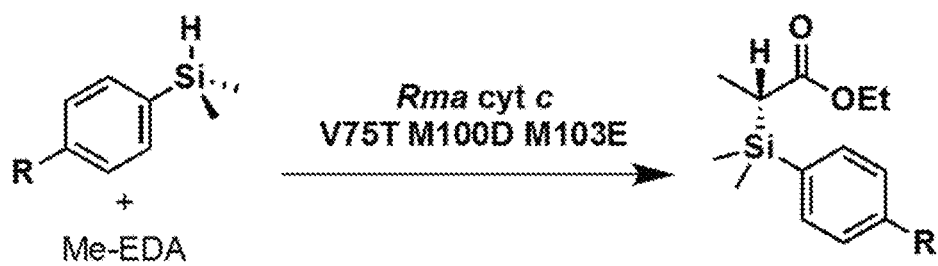
FIGS. 16A and 16B show Hammett analysis of Rma cyt c V75T M100D M103E-catalyzed carbon-silicon bond formation.
Figure 16B:
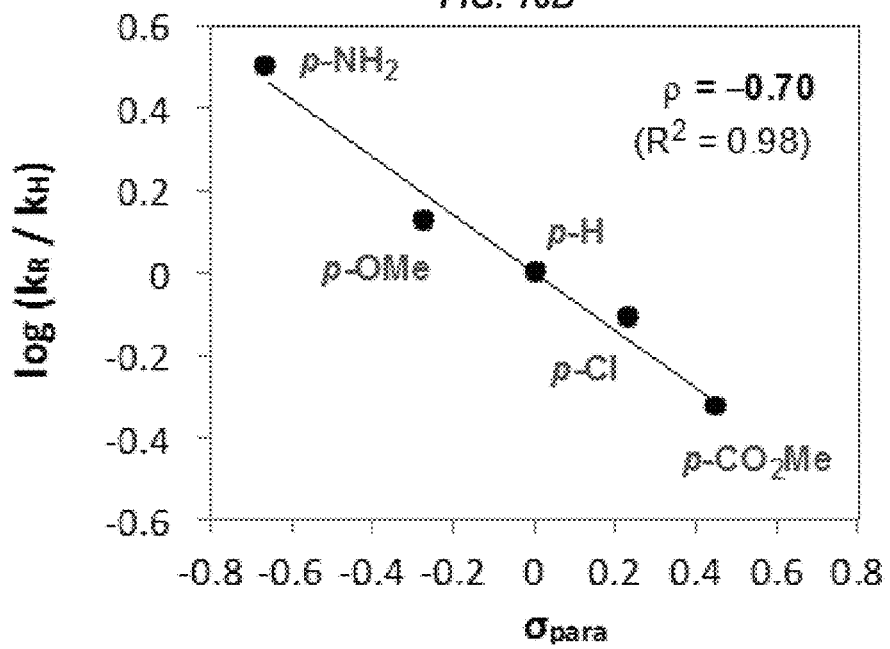

FIG. 14 shows a preparative-scale whole-cell biocatalytic reaction. HB$_{amp/chlor}$ (50 mL) in a 250 mL flask was inoculated with an overnight culture (1 mL, LB$_{amp/chlor}$) of recombinant E. Cloni® EXPRESS BL21(DE3) cells containing a pET22(b)+ plasmid encoding Rma cyt c V75T M100D M103D, and the pEC86 plasmid. The culture was shaken at 37° C. and 250 rpm (no humidity control) until the $OD_{600}$ was 0.6 (approximately 2 hours). The culture was placed on ice for 30 minutes, and IPTG and 5-ALA were added to final concentrations of 20 μM and 200 μM, respectively. The incubator temperature was reduced to 20° C., and the culture was allowed to shake for 20 hours at 140 rpm. Cells were pelleted by centrifugation (4° C., 5 minutes, 4,000×g), resuspended in M9-N buffer, and adjusted to $OD_{600}$=15. Under anaerobic conditions, to a 5 mL reaction vial was added 960 μL whole-cell solution, 40 μL glucose solution (250 mM in M9-N buffer), 15.8 μL 4-(dimethylsilyl)aniline (Compound 23, 0.1 mmol), and 4.9 μL Me-EDA (0.04 mmol) at room temperature. The reaction was shaken at 480 rpm. At 4 h intervals, two additional batches of whole cell (960 μL), glucose (40 μL) and Me-EDA (4.9 μL, 0.04 mmol) were added to the reaction. After the reaction was shaken for a total of 20 hours, the reaction mixture was divided between four 2 mL microcentrifuge tubes, and 0.6 mL EtOAc was added to each tube. The reaction mixtures were subjected to vortex (30 seconds) and centrifugation (14,000 rpm, 7 min) to completely separate the organic and aqueous layers. After removal of the organic layers, two addition rounds of extraction were carried out. The combined organic layers were dried over anhydrous $Na_2SO_4$, concentrated, and purified by silica column chromatography with EtOAc/hexane (1:4 to 1:2) to afford pure organosilicon product Compound 22 (17.6 mg, 0.0700 mmol, 70% yield), together with recovered silane 23 (4.0 mg, 0.0265 mmol, 26.5%). The stereoselectivity of the product was determined as 98% ee by chiral SFC. The protein concentration of $OD_{600}$=15 whole-cell solution was determined to be 7.43 μM by the ferrous assay after cell lysis by sonication. The total turnover number for this reaction was 3,410.

GC Standard Curves for Organosilicon Products

The analysis of product formation in enzymatic reactions was performed based on gas chromatography (GC) standard curves. The general procedure for preparing analytical samples for GC standard curves is described below.

Sample Preparation for GC Standard Curves

Stock solutions of chemically synthesized organosilicon products at various concentrations (20 to 200 mM in MeCN) were prepared. To a microcentrifuge tube was added 340 μL M9-N buffer, 40 μL $Na_2S_2O_4$ (100 mM in $dH_2O$), 20 μL organosilicon product, 20 μL internal standard (20 mM 2-phenylethanol in cyclohexane), and 1 mL cyclohexane. The mixture was vortexed (10 seconds, 3 times) then centrifuged (14,000×g, 5 minutes) to completely separate the organic and aqueous layers. The organic layer (750 μL) was removed for GC analysis.

Chiral Supercritical Fluid Chromatography (SFC) Analysis of Racemic and Enzymatically Synthesized Organosilicon Products All the ee values of enzymatically synthesized organosilicon products were determined using chiral SFC. The chiral SFC reports for racemic and enzymatic products are shown below. The absolute configuration of enzymatically synthesized organosilicon Compound 3 was determined to be (R) by comparing the HPLC retention times of Compound rac-3 and Compound 3 with that reported in the literature (84). The absolute configurations of other organosilicon products were inferred by analogy, assuming the facial selectivity of the diazo reagents remained the same in the biosyntheses of Compounds 3-22.

TABLE 9

Area % report for rac and R-3 (Chiralpak IC, 3% i-PrOH in $CO_2$, 3.5 mL/min, 210 nm)

rac or R-3

| Retention Time (min) | Area (mAU*s) | Area % |
|---|---|---|
| rac-3 | | |
| 2.224 | 842.723 | 50.03 |
| 2.390 | 841.657 | 49.97 |
| Total | 1684.380 | 100.00 |
| R-3 | | |
| 2.172 | 753.160 | 100.00 |
| — | — | |
| Total | 753.160 | 100.00 |

TABLE 10

Area % report for rac and R-4 (Chiralpak AD-H, 3% i-PrOH in $CO_2$, 2.5 mL/min, 210 nm)

rac or R-4

| Retention Time (min) | Area (mAU*s) | Area % |
|---|---|---|
| rac-4 | | |
| 2.097 | 124486 | 45.44 |
| 2.390 | 149493 | 54.56 |
| Total | 273979 | 100.00 |
| R-4 | | |
| 2.142 | 16934.0 | 100.00 |
| — | — | |
| Total | 16934.0 | 100.00 |

TABLE 11

Area % report for rac and R-5 (Chiralpak IC, 3% i-PrOH in $CO_2$, 3.5 mL/min, 210 nm)

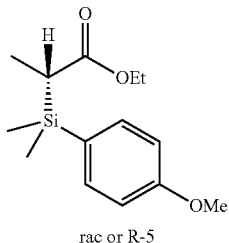

rac or R-5

| Retention Time (min) | Area (mAU*s) | Area % |
|---|---|---|
| rac-5 | | |
| 3.869 | 8651.07 | 49.14 |
| 4.349 | 8955.03 | 50.86 |
| Total | 17606.10 | 100.00 |
| R-5 | | |
| 3.873 | 1422.48 | 100.00 |
| — | — | |
| Total | 1422.48 | 100.00 |

TABLE 12

Area % report for rac and R-6 (Chiralpak AD-H, 3% i-PrOH in $CO_2$, 2.5 mL/min, 210 nm)

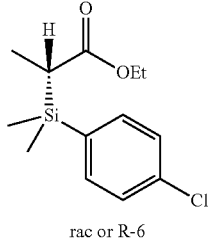

rac or R-6

| Retention Time (min) | Area (mAU*s) | Area % |
|---|---|---|
| rac-6 | | |
| 2.510 | 4898.62 | 49.48 |
| 2.746 | 5001.36 | 50.52 |
| Total | 9899.98 | 100.00 |
| R-6 | | |
| 2.477 | 455.973 | 100.00 |
| — | — | |
| Total | 455.973 | 100.00 |

TABLE 13

Area % report for rac and R-7 (Chiralcel OD-H, 2% i-PrOH in $CO_2$, 2.5 mL/min, 210 nm)

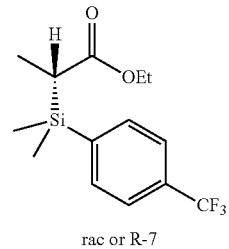

rac or R-7

| Retention Time (min) | Area (mAU*s) | Area % |
|---|---|---|
| rac-7 | | |
| 2.186 | 3895.65 | 49.54 |
| 2.431 | 3967.58 | 50.46 |
| Total | 7863.23 | 100.00 |
| R-7 | | |
| 2.182 | 1738.84 | 99.61 |
| 2.402 | 6.80 | 0.39 |
| Total | 1745.65 | 100.00 |

TABLE 14

Area % report for rac and R-8 (Chiralpak AD-H, 3% i-PrOH in $CO_2$, 2.5 mL/min, 210 nm)

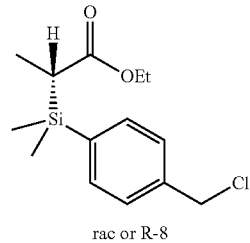

rac or R-8

| Retention Time (min) | Area (mAU*s) | Area % |
|---|---|---|
| rac-8 | | |
| 3.406 | 1698.74 | 49.77 |
| 3.914 | 1714.41 | 50.23 |
| Total | 3413.15 | 100.00 |
| R-8 | | |
| 3.409 | 2377.97 | 99.58 |
| 3.912 | 10.15 | 0.42 |
| Total | 2388.12 | 100.00 |

TABLE 15

Area % report for rac and R-9 (Chiralcel OD-H, 5% i-PrOH in $CO_2$, 2.5 mL/min, 210 nm)

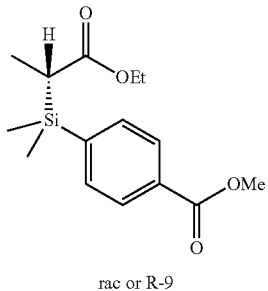

rac or R-9

| Retention Time (min) | Area (mAU*s) | Area % |
|---|---|---|
| rac-9 | | |
| 3.517 | 1773.21 | 50.00 |
| 3.824 | 1772.88 | 50.00 |
| Total | 3546.09 | 100.00 |
| R-9 | | |
| 3.507 | 582.064 | 100.00 |
| — | — | |
| Total | 582.064 | 100.00 |

TABLE 16

Area % report for rac and R-10 (Chiralpak IC, 30% i-PrOH in $CO_2$, 2.5 mL/min, 210 nm)

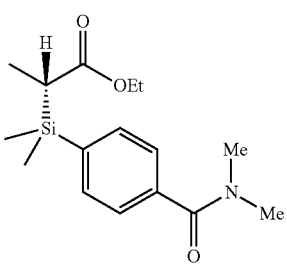

rac or R-10

| Retention Time (min) | Area (mAU*s) | Area % |
|---|---|---|
| rac-10 | | |
| 6.693 | 2779.93 | 49.38 |
| 7.000 | 2849.58 | 50.62 |
| Total | 5629.50 | 100.00 |
| R-10 | | |
| 6.665 | 987.666 | 99.63 |
| 7.005 | 3.594 | 0.36 |
| Total | 991.260 | 100.00 |

TABLE 17

Area % report for rac and R-11 (Chiralpak IC, 7% i-PrOH in $CO_2$, 3.5 mL/min, 210 nm)

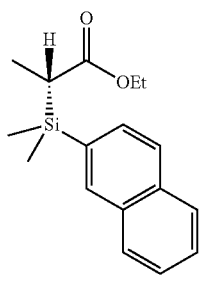

rac or R-11

| Retention Time (min) | Area (mAU*s) | Area % |
|---|---|---|
| rac-11 | | |
| 2.735 | 8677.04 | 47.45 |
| 3.183 | 9609.04 | 52.55 |
| Total | 18286.1 | 100.00 |
| R-11 | | |
| 2.760 | 3675.15 | 97.51 |
| 3.215 | 93.95 | 2.49 |
| Total | 3769.10 | 100.00 |

TABLE 18

Area % report for rac and R-12 (Chiralpak IC, 3% i-PrOH in $CO_2$, 3.5 mL/min, 210 nm)

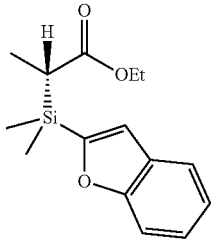

rac or R-12

| Retention Time (min) | Area (mAU*s) | Area % |
|---|---|---|
| rac-12 | | |
| 3.101 | 7145.58 | 49.41 |
| 3.624 | 7315.99 | 50.59 |
| Total | 14461.6 | 100.00 |
| R-12 | | |
| 3.034 | 1490.62 | 99.16 |
| 3.549 | 12.69 | 0.84 |
| Total | 1503.31 | 100.00 |

TABLE 19

Area % report for rac and R-13 (Chiralpak IC, 7% i-PrOH in $CO_2$, 3.5 mL/min, 210 nm)

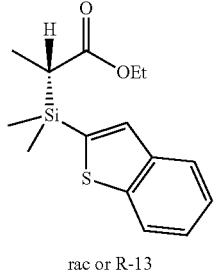

rac or R-13

| Retention Time (min) | Area (mAU*s) | Area % |
|---|---|---|
| rac-13 | | |
| 2.751 | 7136.78 | 48.49 |
| 3.209 | 7581.08 | 51.51 |
| Total | 14717.9 | 100.00 |
| R-13 | | |
| 2.764 | 801.009 | 98.78 |
| 3.219 | 9.889 | 1.22 |
| Total | 810.898 | 100.00 |

TABLE 20

Area % report for rac and R-14 (Chiralpak AD-H, 3% i-PrOH in $CO_2$, 2.5 mL/min, 210 nm)

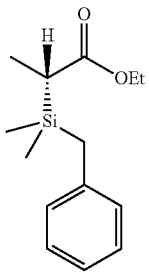

rac or R-14

| Retention Time (min) | Area (mAU*s) | Area % |
|---|---|---|
| rac-14 | | |
| 2.142 | 1384.73 | 49.85 |
| 2.351 | 1393.07 | 50.15 |
| Total | 2777.80 | 100.00 |
| R-14 | | |
| 2.191 | 1991.26 | 99.62 |
| 2.402 | 7.58 | 0.38 |
| Total | 1998.84 | 100.00 |

TABLE 21

Area % report for rac and R-15 (Chiralpak IC, 3% i-PrOH in $CO_2$, 3.5 mL/min, 210 nm)

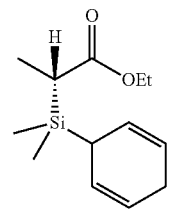

rac or R-15

| Retention Time (min) | Area (mAU*s) | Area % |
|---|---|---|
| rac-15 | | |
| 2.356 | 361.685 | 50.30 |
| 2.500 | 357.384 | 49.70 |
| Total | 719.070 | 100.00 |
| R-15 | | |
| 2.426 | 390.115 | 99.45 |
| 2.556 | 2.125 | 0.54 |
| Total | 392.240 | 100.00 |

TABLE 22

Area % report for rac and R-16 (Chiralpak AD-H, 3% i-PrOH in $CO_2$, 2.5 mL/min, 210 nm)

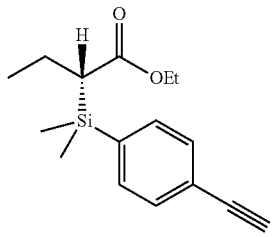

rac or R-16

| Retention Time (min) | Area (mAU*s) | Area % |
|---|---|---|
| rac-16 | | |
| 2.602 | 4276.04 | 49.44 |
| 3.526 | 4373.23 | 50.56 |
| Total | 8649.28 | 100.00 |
| R-16 | | |
| 2.607 | 2426.65 | 100.00 |
| Total | 2426.65 | 100.00 |

TABLE 23

Area % report for rac and R-17 (Chiralpak IC, 3% i-PrOH in $CO_2$, 2.5 mL/min, 210 nm)

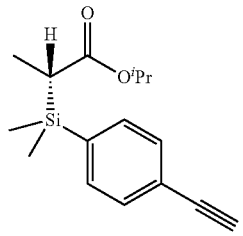

rac or R-17

| Retention Time (min) | Area (mAU*s) | Area % |
|---|---|---|
| rac-17 | | |
| 3.808 | 1442.74 | 49.78 |
| 4.074 | 1455.49 | 50.22 |
| Total | 2898.23 | 100.00 |
| R-17 | | |
| 3.829 | 2089.15 | 100.00 |
| Total | 2089.15 | 100.00 |

TABLE 24

Area % report for rac and R-18 (Chiralpak IC, 3% i-PrOH in $CO_2$, 3.5 mL/min, 210 nm)

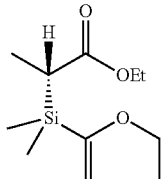

rac or R-18

| Retention Time (min) | Area (mAU*s) | Area % |
|---|---|---|
| rac-18 | | |
| 2.680 | 1366.02 | 50.54 |
| 2.887 | 1336.57 | 49.46 |
| Total | 2702.59 | 100.00 |
| R-18 | | |
| 2.628 | 813.657 | 99.63 |
| 2.922 | 2.984 | 0.37 |
| Total | 816.641 | 100.00 |

TABLE 25

Area % report for rac and R-19 (Chiralpak IC, 3% i-PrOH in $CO_2$, 3.5 mL/min, 210 nm)

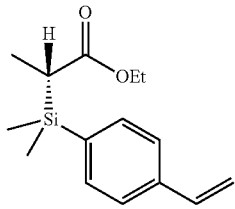

rac or R-19

| Retention Time (min) | Area (mAU*s) | Area % |
|---|---|---|
| rac-19 | | |
| 2.791 | 6332.09 | 49.69 |
| 3.001 | 6411.17 | 50.31 |
| Total | 12743.3 | 100.00 |
| R-19 | | |
| 2.758 | 1559.90 | 99.13 |
| 2.972 | 13.65 | 0.87 |
| Total | 1573.56 | 100.00 |

TABLE 26

Area % report for rac and R-20 (Chiralcel OD-H, 3% i-PrOH in $CO_2$, 2.5 mL/min, 210 nm)

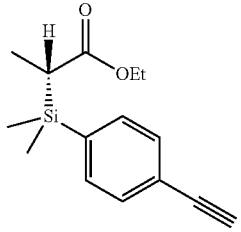

rac or R-20

| Retention Time (min) | Area (mAU*s) | Area % |
|---|---|---|
| rac-20 | | |
| 3.410 | 13436.2 | 48.40 |
| 3.774 | 14326.4 | 51.60 |
| Total | 27762.6 | 100.00 |
| R-20 | | |
| 3.406 | 1894.53 | 99.84 |
| 3.715 | 2.97 | 0.16 |
| Total | 1897.50 | 100.00 |

TABLE 27

Area % report for rac and R-21 (Chiralpak IC, 10% i-PrOH in CO₂, 2.5 mL/min, 210 nm)

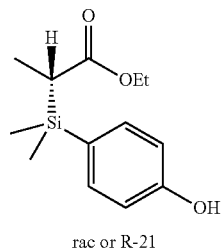

rac or R-21

| Retention Time (min) | Area (mAU*s) | Area % |
|---|---|---|
| rac-21 | | |
| 3.853 | 664.781 | 50.19 |
| 4.264 | 659.660 | 49.81 |
| Total | 1324.441 | 100.00 |
| R-21 | | |
| 3.883 | 3332.68 | 99.58 |
| 4.331 | 13.94 | 0.42 |
| Total | 3346.62 | 100.00 |

TABLE 28

Area % report for rac and R-22 (Chiralpak AD-H, 10% i-PrOH in CO₂, 2.5 mL/min, 210 nm)

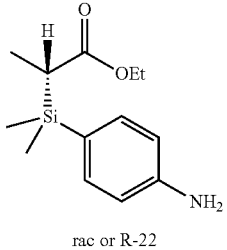

rac or R-22

| Retention Time (min) | Area (mAU*s) | Area % |
|---|---|---|
| rac-22 | | |
| 5.162 | 9214.41 | 48.50 |
| 5.617 | 9783.58 | 51.50 |
| Total | 18998.0 | 100.00 |
| R-22 | | |
| 5.638 | 195.47 | 100.00 |
| Total | 195.47 | 100.00 |

Preparative-Scale Reaction (0.1 Mmol):

TABLE 29

Area % report for R-22: R-22 (OD 15-whole cell)

| Retention Time (min) | Area (mAU*s) | Area % |
|---|---|---|
| 5.537 | 45.97 | 1.15 |
| 5.990 | 3935.62 | 98.85 |
| Total | 3981.59 | 100.00 |

REFERENCES

1. M. B. Frampton, P. M. Zelisko, Organosilicon biotechnology. Silicon 1, 147-163 (2009).
2. Z. Rappoport, Y. Apeloig, Ed., The Chemistry of Organic Silicon Compounds, Vol 3 (Wiley, 2003).
3. S. A. Ponomarenko, S. Kirchmeyer, Conjugated organosilicon materials for organic electronics and photonics. Adv. Polym. Sci. 235, 33-110 (2011).
4. G. A. Showell, J. S. Mills, Chemistry challenges in lead optimization: silicon isosteres in drug discovery. Drug Discov. Today 8, 551-556 (2003).
5. A. K. Franz, S. O. Wilson, Organosilicon molecules with medicinal applications. J. Med. Chem. 56, 388-405 (2013).
6. P. T. Anastas, J. Warner, Green Chemistry: Theory and Practice (Oxford University Press, New York, 1998).
7. A. M. Tondreau, C. C. H. Atienza, K. J. Weller, S. A. Nye, K. M. Lewis, J. G. P. Delis, P. J. Chirik, Iron catalysts for selective anti-Markovnikov alkene hydrosilylation using tertiary silanes. Science 335, 567-570 (2012).
8. A. A. Toutov, W.-B. Liu, K. N. Betz, A. Fedorov, B. M. Stoltz, R. H Grubbs, Silylation of C—H bonds in aromatic heterocycles by an Earth-abundant metal catalyst. Nature 518, 80-84 (2015).
9. B. Marciniec, Ed., Hydrosilylation: A Comprehensive Review on Recent Advances (Springer Netherlands, 2009).
10. T. Lee, J. F. Hartwig, Rhodium-catalyzed enantioselective silylation of cyclopropyl C—H bonds. Angew. Chem. Int. Ed. 128, 8723-8727 (2016) and references therein.
11. R. Sambasivan, Z. T. Ball, Metallopeptides for asymmetric dirhodium catalysis. J. Am. Chem. Soc. 132, 9289-9291 (2010).
12. D. Chen, D.-X. Zhu, M.-H. Xu, Rhodium(I)-catalyzed highly enantioselective insertion of carbenoid into Si—H: efficient access to functional chiral silanes. J. Am. Chem. Soc. 138, 1498-1501 (2016).
13. Y. Yasutomi, H. Suematsu, T. Katsuki, Iridium(III)-catalyzed enantioselective Si—H bond insertion and formation of an enantioenriched silicon center. J. Am. Chem. Soc. 132, 4510-4511 (2010).
14. Y.-Z. Zhang, S.-F. Zhu, L.-X. Wang, Q.-L. Zhou, Copper-catalyzed highly enantioselective carbenoid insertion into Si—H bonds. Angew. Chem. Int. Ed. 47, 8496-8498 (2008).
15. S. Hyde, J. Veliks, B. Liégault, D. Grassi, M. Taillefer, V. Gouverneur, Copper-catalyzed insertion into heteroatom-hydrogen bonds with trifluorodiazoalkanes. Angew. Chem. Int. Ed. 55, 3785-3789 (2016).
16. U. T. Bornscheuer, G. W. Huisman, R. J. Kazlauskas, S. Lutz, J. C. Moore, K. Robins, Engineering the third wave of biocatalysis. Nature 485, 185-194 (2012).

17. J. L. Tucker, M. M. Faul, Industrial research: Drug companies must adopt green chemistry. Nature 534, 27-29 (2016).
18. P. J. O'Brien, D. Herschlag, Catalytic promiscuity and the evolution of new enzymatic activities. Chem. Biol. 6, R91-R105 (1999).
19. S. D. Copley, Enzymes with extra talents: moonlighting functions and catalytic promiscuity. Curr. Opin. Chem. Biol. 7, 265-272 (2003).
20. O. Khersonsky, D. S. Tawfik, Enzyme promiscuity: a mechanistic and evolutionary perspective. Ann. Rev. Biochem. 79, 471-505 (2010).
21. P. S. Coelho, E M. Brustad, A. Kannan, F. H. Arnold, Olefin cyclopropanation via carbene transfer catalyzed by engineered cytochrome P450 enzymes. Science 339, 307-310 (2013).
22. Z. J. Wang, N. E. Peck, H. Renata, F. H. Arnold, Cytochrome P450-catalyzed insertion of carbenoids into N—H bonds. Chem. Sci. 5, 598-601 (2014).
23. V. Tyagi, R. B Bonn, R. Fasan, Intermolecular carbene S—H insertion catalysed by engineered myoglobin-based catalysts. Chem. Sci. 6, 2488-2494 (2015).
24. Only stoichiometric iron carbenoid insertion into Si—H bonds has been reported, see: E. Scharrer, M. Brookhart, Insertion reactions of electrophilic iron carbene complexes with organosilanes: a synthetic and mechanistic study. J. Organomet Chem. 497, 61-71 (1995) and references therein.
25. M. Stelter, A. M. P. Melo, M. M. Pereira, C. M. Gomes, G. O. Hreggvidsson, S. Hjorleifsdottir, L. M. Saraiva, M. Teixeira, M. Archer, A novel type of monoheme cytochrome c: biochemical and structural characterization at 1.23 Å resolution of *Rhodothermus marinus* cytochrome c. Biochemistry 47, 11953-11963 (2008).
26. J. G. Kleingardner, K. L. Bren, Biological significance and applications of heme c proteins and peptides. Acc. Chem. Res. 48, 1845-1852 (2015).
27. B. D. Levin, K. A. Walsh, K. K. Sullivan, K. L. Bren, S. J. Elliott, Methionine ligand lability of homologous monoheme cytochromes c. Inorg. Chem. 54, 38-46 (2015).
28. S. Zaidi, M. I. Hassan, A. Islam, F. Ahmad, The role of key residues in structure, function, and stability of cytochrome-c. Cell. Mol. Life Sci. 71, 229-255 (2014).
29. D. G. Gibson et al., Enzymatic assembly of DNA molecules up to several hundred kilobases. Nat. Meth. 6, 343-345 (2009).
30. E. Arslan, H. Schulz, R. Zufferey, P. Kiinzler, L. Thony-Meyer, Overproduction of the *Bradyrhizobium japonicum* c-type cytochrome subunits of the cbb3 oxidase in *Escherichia coli*. Biochem. Biophys. Res. Commun. 251, 744-747 (1998).
31. J. Sambrook, E. Frisch, T. Maniatis, Molecular Cloning: A Laboratory Manual (Cold Spring Harbor Laboratory Press, New York, 1989).
32. E. A. Berry, B. L. Trumpower, Simultaneous determination of hemes a, b, and c from pyridine hemochrome spectra. Anal. Biochem. 161, 1-15 (1987).
33. S. Kille et al., Reducing codon redundancy and screening effort of combinatorial protein libraries created by saturation mutagenesis. ACS Synth Biol. 2, 83-92 (2013).
34. S. Hyde, J. Veliks, B. Liégault, D. Grassi, M. Taillefer, V. Gouverneur, Copper-catalyzed insertion into heteroatom-hydrogen bonds with trifluorodiazoalkanes. Angew. Chem. Int. Ed. 55, 3785-3789 (2016).
35. J. Wu, J. S. Panek, Total synthesis of (−)-virginiamycin M2: application of crotylsilanes accessed by enantioselective Rh(II) or Cu(I) promoted carbenoid Si—H insertion. J. Org. Chem. 76, 9900-9918 (2011).
36. Y.-Z. Zhang, S.-F. Zhu, L.-X. Wang, Q.-L. Zhou, Copper-catalyzed highly enantioselective carbenoid insertion into Si—H bonds. Angew. Chem. Int. Ed. 47, 8496-8498 (2008).
37. L. A. Dakin, P. C. Ong, J. S. Panek, R. J. Staples, P. Stavropoulos, Speciation and mechanistic studies of chiral copper(I) Schiff base precursors mediating asymmetric carbenoid insertion reactions of diazoacetates into the Si—H bond of silanes. Organometallics 19, 2896-2908 (2000).
38. L. A. Dakin, S. E. Schaus, E. N. Jacobsen, J. S. Panek, Carbenoid insertions into the silicon-hydrogen bond catalyzed by chiral copper(I) Schiff base complexes. Tetrahedron Lett. 39, 8947-8950 (1998).
39. Y. Yasutomi, H. Suematsu, T. Katsuki, Iridium(III)-catalyzed enantioselective Si—H bond insertion and formation of an enantioenriched silicon center. J. Am. Chem. Soc. 132, 4510-4511 (2010).
40. J.-C. Wang et al., Highly enantioselective intermolecular carbene insertion to C—H and Si—H bonds catalyzed by a chiral iridium(III) complex of a D4-symmetric Halterman porphyrin ligand. Chem. Commun. 48, 4299-4301 (2012).
41. D. Chen, D.-X. Zhu, M.-H. Xu, Rhodium(I)-catalyzed highly enantioselective insertion of carbenoid into Si—H: efficient access to functional chiral silanes. J. Am. Chem. Soc. 138, 1498-1501 (2016).
42. R. Hrdina, L. Guénée, D. Moraleda, J. Lacour, Synthesis, structural analysis, and catalytic properties of tetrakis (binaphthyl or octahydrobinaphthyl phosphate) dirhodium(II,II) complexes. Organometallics 32, 473-479 (2013).
43. R. Sambasivan, Z. T. Ball, Metallopeptides for asymmetric dirhodium catalysis. J. Am. Chem. Soc. 132, 9289-9291 (2010).
44. M. Ge, E. J. Corey, A method for the catalytic enantioselective synthesis of 6-silylated 2-cyclohexenones. Tetrahedron Lett. 47, 2319-2321 (2006).
45. R. T. Buck et al., Asymmetric rhodium carbene insertion into the Si—H bond: identification of new dirhodium(II) carboxylate catalysts using parallel synthesis techniques. Tetrahedron: Asymmetry 14, 791-816 (2003).
46. R. T. Buck et al., Parallel synthesis techniques in the identification of new chiral dirhodium(II) carboxylates for asymmetric carbenoid insertion reactions. Tetrahedron Lett. 39, 7181-7184 (1998).
47. M. P. Doyle, W. Hu, I. M. Phillips, C. J. Moody, A. G. Pepper, A. M. Z. Slawin, Reactivity enhancement for chiral dirhodium(II) tetrakis(carboxamidates). Adv. Synth. Catal. 343, 112-117 (2001).
48. S. Kitagaki, M. Kinoshita, M. Takeba, M. Anada, S. Hashimoto, Enantioselective Si—H insertion of methyl phenyldiazoacetate catalyzed by dirhodium(II) carboxylates incorporating N-phthaloyl-(S)-amino acids as chiral bridging ligands. Tetrahedron: Asymmetry 11, 3855-3859 (2000).
49. H. M. L. Davies, T. Hansen, J. Rutberg, P. R. Bruzinski, Rhodium (II) (S)—N-(arylsulfonyl)prolinate catalyzed asymmetric insertions of vinyl- and phenylcarbenoids into the Si—H bond. Tetrahedron Lett. 38, 1741-1744 (1997).
50. R. T. Buck et al., Asymmetric rhodium carbenoid insertion into the Si—H bond, Tetrahedron Lett. 37, 7631-7634 (1996).

51. A. DeAngelis, R. Panish, J. M. Fox, Rh-catalyzed intermolecular reactions of α-alkyl-α-diazo carbonyl compounds with selectivity over β-hydride migration. Acc. Chem. Res. 49, 115-127 (2016).
52. P. S. Coelho, E. M. Brustad, A. Kannan, F. H. Arnold, Olefin cyclopropanation via carbene transfer catalyzed by engineered cytochrome P450 enzymes. Science 339, 307-310 (2013).
53. Z. J. Wang et al., Improved cyclopropanation activity of histidine-ligated cytochrome P450 enables the enantioselective formal synthesis of levomilnacipran. Angew. Chem. Int. Ed. 53, 6810-6813 (2014).
54. T. K. Hyster, C. C. Farwell, A. R. Buller, J. A. McIntosh, F. H. Arnold, Enzyme-controlled nitrogen-atom transfer enables regiodivergent C—H amination. J. Am. Chem. Soc. 136, 15505-15508 (2014).
55. P. S. Coelho et al., A serine-substituted P450 catalyzes highly efficient carbene transfer to olefins in vivo. Nat. Chem. Biol. 9, 485-487 (2013).
56. H. Renata, R. D. Lewis, J. Sweredoski, A. Moradian, Z. J. Wang, F. H. Arnold, Identification of mechanism-based inactivation in P450-catalyzed cyclopropanation facilitates engineering of improved enzymes. J. Am. Chem. Soc. (2016) doi: 10.1021/jacs.6b06823.
57. M. Bordeaux, V. Tyagi, R. Fasan, Highly diastereoselective and enantioselective olefin cyclopropanation using engineered myoglobin-based catalysts. Angew. Chem. Int. Ed. 54, 1744-1748 (2015).
58. Y. Landais, D. Planchenault, Preparation of optically active alpha-silylcarbonyl compounds using asymmetric alkylation of alpha-silylacetic esters and asymmetric metal-carbene insertion into the Si—H bond. Tetrahedron 53, 2855-2870 (1997).
59. M. Stelter, A. M. P. Melo, M. M. Pereira, C. M. Gomes, G. O. Hreggvidsson, S. Hjorleifsdottir, L. M. Saraiva, M. Teixeira, M. Archer, A novel type of monoheme cytochrome c: biochemical and structural characterization at 1.23 Å resolution of *Rhodothermus marinus* cytochrome c. Biochemistry 47, 11953-11963 (2008).
60. Y. Landais, L. Parra-Rapado, D. Planchenault, V. Weber, Mechanism of metal-carbenoid insertion into the Si—H bond. Tetrahedron Lett. 1997, 38, 229-232.
61. C. Peng, Y. Wang, J. Wang, Palladium-catalyzed cross-coupling of α-diazocarbonyl compounds with arylboronic acids. J. Am. Chem. Soc. 130, 1566-1567 (2008).
62. L. Huang, W. D. Wulff, Catalytic asymmetric synthesis of trisubstituted aziridines. J. Am. Chem. Soc. 133, 8892-8895 (2011).
63. E. J. Rayment, N. Summerhill, E. A. Anderson, Synthesis of phenols via fluoride-free oxidation of arylsilanes and arylmethoxysilanes. J. Org. Chem. 77, 7052-7060 (2012).
64. W.-C. Liao, W.-H. Chen, C.-H. Chen, T.-S. Lim, T.-Y. Luh, Photoinduced electron transfer as a probe for the folding behavior of dimethylsilylene-spaced alternating donor-acceptor oligomers and polymers. Macromolecules 46, 1305-1311 (2013).
65. F. T. Oakes, J. F. Sebastian, Direct observation of acyl anion equivalents by carbon-13 Fourier transform Nuclear Magnetic Resonance. J. Org. Chem. 45, 4959-4961 (1980).
66. H. Rosenberg, T. T. Tsai, N. K. Ngo, Synthesis of carbonate-containing high-temperature poly(arylene-siloxanylenes). J. Polym. Sci. A Polym. Chem. 20, 1-13 (1982).
67. T. K. Dougherty, Aromatic amine terminated silicone monomers, oligomers, and polymers therefrom. U.S. Pat. No. 5,286,890 (1994).
68. D. S. Kim, S. C. Shim, Synthesis and properties of poly(silylenephenylene-vinylene)s. J. Polym. Sci. A Polym. Chem. 37, 2263-2273 (1999).
69. B. Wang, H. W. Ma, Y. S. Wang, Y. Li, Synthesis and characterization of novel liquid crystalline polystyrene. Chem. Lett. 42, 915-917 (2013).
70. A. Simonneau, O. Martin, 3-Silylated cyclohexa-1,4-dienes as precursors for gaseous hydrosilanes: the B(C6F5)3-catalyzed transfer hydrosilylation of alkenes. Angew. Chem. Int. Ed. 52, 11905-11907 (2013).
71. C. M. Kisukuri, D. J. Palmeira, T. S. Rodrigues, P. H. C. Camargo, L. H. Andrade, Bimetallic nanoshells as platforms for metallo- and biometallo-catalytic applications. ChemCatChem 8, 171-179 (2016).
72. S. E. Denmark, R. C. Smith, W.-T. T. Chang, J. M. Muhuhi, Cross-coupling reactions of aromatic and heteroaromatic silanolates with aromatic and heteroaromatic halides. J. Am. Chem. Soc. 131, 3104-3118 (2009).
73. M. B. Frampton, P. M. Zelisko, Organosilicon biotechnology. Silicon 1, 147-163 (2009).
74. Z. Rappoport, Y. Apeloig, Eds., The Chemistry of Organic Silicon Compounds (Wiley, 2003), vol. 3.
75. S. A. Ponomarenko, S. Kirchmeyer, Conjugated organosilicon materials for organic electronics and photonics. Adv. Polym. Sci. 235, 33-110 (2011).
76. G. A. Showell, J. S. Mills, Chemistry challenges in lead optimization: Silicon isosteres in drug discovery. Drug Discov. Today 8, 551-556 (2003).
77. A. K. Franz, S. O. Wilson, Organosilicon molecules with medicinal applications. J. Med. Chem. 56, 388-405 (2013).
78. P. T. Anastas, J. Warner, Green Chemistry: Theory and Practice (Oxford Univ. Press, New York, 1998).
79. A. M. Tondreau, C. C. H. Atienza, K. J. Weller, S. A. Nye, K. M. Lewis, J. G. P. Delis, P. J. Chirik, Iron catalysts for selective anti-Markovnikov alkene hydrosilylation using tertiary silanes. Science 335, 567-570 (2012).
80. A. A. Toutov, W.-B. Liu, K. N. Betz, A. Fedorov, B. M. Stoltz, R. H. Grubbs, Silylation of C—H bonds in aromatic heterocycles by an Earth-abundant metal catalyst. Nature 518, 80-84 (2015).
81. B. Marciniec, Ed., Hydrosilylation: A Comprehensive Review on Recent Advances (Springer, Netherlands, 2009).
82. T. Lee, J. F. Hartwig, Rhodium-catalyzed enantioselective silylation of cyclopropyl C—H bonds. Angew. Chem. Int. Ed. 55, 8723-8727 (2016) and references therein.
83. R. Sambasivan, Z. T. Ball, Metallopeptides for asymmetric dirhodium catalysis. J. Am. Chem. Soc. 132, 9289-9291 (2010).
84. D. Chen, D.-X. Zhu, M.-H. Xu, Rhodium(I)-catalyzed highly enantioselective insertion of carbenoid into Si—H: Efficient access to functional chiral silanes. J. Am. Chem. Soc. 138, 1498-1501 (2016).
85. Y. Yasutomi, H. Suematsu, T. Katsuki, Iridium(III)-catalyzed enantioselective Si—H bond insertion and formation of an enantioenriched silicon center. J. Am. Chem. Soc. 132, 4510-4511 (2010).
86. Y.-Z. Zhang, S.-F. Zhu, L.-X. Wang, Q.-L. Zhou, Copper-catalyzed highly enantioselective carbenoid insertion into Si—H bonds. Angew. Chem. Int. Ed. 47, 8496-8498 (2008).

87. S. Hyde, J. Veliks, B. Liégault, D. Grassi, M. Taillefer, V. Gouverneur, Copper-catalyzed insertion into heteroatom-hydrogen bonds with trifluorodiazoalkanes. Angew. Chem. Int. Ed. 55, 3785-3789 (2016).
88. See below for details.
89. U. T. Bornscheuer, G. W. Huisman, R. J. Kazlauskas, S. Lutz, J. C. Moore, K. Robins, Engineering the third wave of biocatalysis. Nature 485, 185-194 (2012).
90. J. L. Tucker, M. M. Faul, Industrial research: Drug companies must adopt green chemistry. Nature 534, 27-29 (2016).
91. P. J. O'Brien, D. Herschlag, Catalytic promiscuity and the evolution of new enzymatic activities. Chem. Biol. 6, R91-R105 (1999).
92. S. D. Copley, Enzymes with extra talents: Moonlighting functions and catalytic promiscuity. Curr. Opin. Chem. Biol. 7, 265-272 (2003).
93. O. Khersonsky, D. S. Tawfik, Enzyme promiscuity: A mechanistic and evolutionary perspective. Annu. Rev. Biochem. 79, 471-505 (2010).
94. P. S. Coelho, E. M. Brustad, A. Kannan, F. H. Arnold, Olefin cyclopropanation via carbene transfer catalyzed by engineered cytochrome P450 enzymes. Science 339, 307-310 (2013).
95. Z. J. Wang, N. E. Peck, H. Renata, F. H. Arnold, Cytochrome P450-catalyzed insertion of carbenoids into N—H bonds. Chem. Sci. 5, 598-601 (2014).
96. V. Tyagi, R. B. Bonn, R. Fasan, Intermolecular carbene S—H insertion catalysed by engineered myoglobin-based catalysts. Chem. Sci. 6, 2488-2494 (2015).
97. Only stoichiometric iron carbenoid insertion into Si—H bonds has been reported (30).
98. M. Stelter, A. M. P. Melo, M. M. Pereira, C. M. Gomes, G. O. Hreggvidsson, S. Hjorleifsdottir, L. M. Saraiva, M. Teixeira, M. Archer, A novel type of monoheme cytochrome c: Biochemical and structural characterization at 1.23 A resolution of Rhodothermus marinus cytochrome c. Biochemistry 47, 11953-11963 (2008).
99. J. G. Kleingardner, K. L. Bren, Biological significance and applications of heme c proteins and peptides. Acc. Chem. Res. 48, 1845-1852 (2015).
100. B. D. Levin, K. A. Walsh, K. K. Sullivan, K. L. Bren, S. J. Elliott, Methionine ligand lability of homologous monoheme cytochromes c. Inorg. Chem. 54, 38-46 (2015).
101. S. Zaidi, M. I. Hassan, A. Islam, F. Ahmad, The role of key residues in structure, function, and stability of cytochrome-c. Cell. Mol. Life Sci. 71, 229-255 (2014).
102. E. Scharrer, M. Brookhart, Insertion reactions of electrophilic iron carbene complexes with organosilanes: A synthetic and mechanistic study. J. Organomet. Chem. 497, 61-71 (1995).
103. D. G. Gibson, L. Young, R. Y. Chuang, J. C. Venter, C. A. Hutchison 3rd, H. O. Smith, Enzymatic assembly of DNA molecules up to several hundred kilobases. Nat. Methods 6, 343-345 (2009).
104. E. Arslan, H. Schulz, R. Zufferey, P. Künzler, L. Thöny-Meyer, Overproduction of the Bradyrhizobium japonicum c-type cytochrome subunits of the cbb3 oxidase in Escherichia coli. Biochem. Biophys. Res. Commun. 251, 744-747 (1998).
105. J. Sambrook, E. Frisch, T. Maniatis, Molecular Cloning: A Laboratory Manual (Cold Spring Harbor Laboratory Press, New York, 1989).
106. E. A. Berry, B. L. Trumpower, Simultaneous determination of hemes a, b, and c from pyridine hemochrome spectra. Anal. Biochem. 161, 1-15 (1987).
107. S. Kille, C. G. Acevedo-Rocha, L. P. Parra, Z. G. Zhang, D. J. Opperman, M. T. Reetz, J. P. Acevedo, Reducing codon redundancy and screening effort of combinatorial protein libraries created by saturation mutagenesis. ACS Synth. Biol. 2, 83-92 (2013).
108. J. Wu, J. S. Panek, Total synthesis of (−)-virginiamycin M2: Application of crotylsilanes accessed by enantioselective Rh(II) or Cu(I) promoted carbenoid Si—H insertion. J. Org. Chem. 76, 9900-9918 (2011).
109. L. A. Dakin, P. C. Ong, J. S. Panek, R. J. Staples, P. Stavropoulos, Speciation and mechanistic studies of chiral copper(I) Schiff base precursors mediating asymmetric carbenoid insertion reactions of diazoacetates into the Si—H bond of silanes. Organometallics 19, 2896-2908 (2000).
110. L. A. Dakin, S. E. Schaus, E. N. Jacobsen, J. S. Panek, Carbenoid insertions into the silicon-hydrogen bond catalyzed by chiral copper(I) Schiff base complexes. Tetrahedron Lett. 39, 8947-8950 (1998).
111. J.-C. Wang, Z. J. Xu, Z. Guo, Q. H. Deng, C. Y. Zhou, X. L. Wan, C. M. Che, Highly enantioselective intermolecular carbene insertion to C—H and Si—H bonds catalyzed by a chiral iridium(III) complex of a D4-symmetric Halterman porphyrin ligand. Chem. Commun. (Camb.) 48, 4299-4301 (2012).
112. R. Hrdina, L. Guénée, D. Moraleda, J. Lacour, Synthesis, structural analysis, and catalytic properties of tetrakis(binaphthyl or octahydrobinaphthyl phosphate) dirhodium(II,II) complexes. Organometallics 32, 473-479 (2013).
113. M. Ge, E. J. Corey, A method for the catalytic enantioselective synthesis of 6-silylated 2-cyclohexenones. Tetrahedron Lett. 47, 2319-2321 (2006).
114. R. T. Buck, D. M. Coe, M. J. Drysdale, L. Ferris, D. Haigh, C. J. Moody, N. D. Pearson, J. B. Sanghera, Asymmetric rhodium carbene insertion into the Si—H bond: Identification of new dirhodium(II) carboxylate catalysts using parallel synthesis techniques. Tetrahedron Asymmetry 14, 791-816 (2003).
115. R. T. Buck, D. M. Coe, M. J. Drysdale, C. J. Moody, N. D. Pearson, Parallel synthesis techniques in the identification of new chiral dirhodium(II) carboxylates for asymmetric carbenoid insertion reactions. Tetrahedron Lett. 39, 7181-7184 (1998).
116. M. P. Doyle, W. Hu, I. M. Phillips, C. J. Moody, A. G. Pepper, A. M. Z. Slawin, Reactivity enhancement for chiral dirhodium(II) tetrakis(carboxamidates). Adv. Synth. Catal. 343, 112-117 (2001).
117. S. Kitagaki, M. Kinoshita, M. Takeba, M. Anada, S. Hashimoto, Enantioselective Si—H insertion of methyl phenyldiazoacetate catalyzed by dirhodium(II) carboxylates incorporating N-phthaloyl-(S)-amino acids as chiral bridging ligands. Tetrahedron Asymmetry 11, 3855-3859 (2000).
118. H. M. L. Davies, T. Hansen, J. Rutberg, P. R. Bruzinski, Rhodium (II) (S)—N-(arylsulfonyl)prolinate catalyzed asymmetric insertions of vinyl- and phenylcarbenoids into the Si—H bond. Tetrahedron Lett. 38, 1741-1744 (1997).
119. R. T. Buck, M. P. Doyle, M. J. Drysdale, L. Ferris, D. C. Forbes, D. Haigh, C. J. Moody, N. D. Pearson, Q.-L. Zhou, Asymmetric rhodium carbenoid insertion into the Si—H bond. Tetrahedron Lett. 37, 7631-7634 (1996).
120. A. DeAngelis, R. Panish, J. M. Fox, Rh-catalyzed intermolecular reactions of α-alkyl-α-diazo carbonyl compounds with selectivity over β-hydride migration. Acc. Chem. Res. 49, 115-127 (2016).

121. Z. J. Wang, H. Renata, N. E. Peck, C. C. Farwell, P. S. Coelho, F. H. Arnold, Improved cyclopropanation activity of histidine-ligated cytochrome P450 enables the enantioselective formal synthesis of levomilnacipran. Angew. Chem. Int. Ed. 53, 6810-6813 (2014).
122. T. K. Hyster, C. C. Farwell, A. R. Buller, J. A. McIntosh, F. H. Arnold, Enzyme-controlled nitrogen-atom transfer enables regiodivergent C—H amination. J. Am. Chem. Soc. 136, 15505-15508 (2014).
123. P. S. Coelho, Z. J. Wang, M. E. Ener, S. A. Baril, A. Kannan, F. H. Arnold, E. M. Brustad, A serine-substituted P450 catalyzes highly efficient carbene transfer to olefins in vivo. Nat. Chem. Biol. 9, 485-487 (2013).
124. H. Renata, R. D. Lewis, M. J. Sweredoski, A. Moradian, S. Hess, Z. J. Wang, F. H. Arnold, Identification of mechanism-based inactivation in P450-catalyzed cyclopropanation facilitates engineering of improved enzymes. J. Am. Chem. Soc. 138, 12527-12533 (2016).
125. M. Bordeaux, V. Tyagi, R. Fasan, Highly diastereoselective and enantioselective olefin cyclopropanation using engineered myoglobin-based catalysts. Angew. Chem. Int. Ed. 54, 1744-1748 (2015).
126. Y. Landais, D. Planchenault, Preparation of optically active alpha-silylcarbonyl compounds using asymmetric alkylation of alpha-silylacetic esters and asymmetric metal-carbene insertion into the Si—H bond. Tetrahedron 53, 2855-2870 (1997).
127. Y. Landais, L. Parra-Rapado, D. Planchenault, V. Weber, Mechanism of metal-carbenoid insertion into the Si—H bond. Tetrahedron Lett. 38, 229-232 (1997).
128. C. Peng, Y. Wang, J. Wang, Palladium-catalyzed cross-coupling of α-diazocarbonyl compounds with arylboronic acids. J. Am. Chem. Soc. 130, 1566-1567 (2008).
129. L. Huang, W. D. Wulff, Catalytic asymmetric synthesis of trisubstituted aziridines. J. Am. Chem. Soc. 133, 8892-8895 (2011).
130. E. J. Rayment, N. Summerhill, E. A. Anderson, Synthesis of phenols via fluoride-free oxidation of arylsilanes and arylmethoxysilanes. J. Org. Chem. 77, 7052-7060 (2012).
131. W.-C. Liao, W.-H. Chen, C.-H. Chen, T.-S. Lim, T.-Y. Luh, Photoinduced electron transfer as a probe for the folding behavior of dimethylsilylene-spaced alternating donor-acceptor oligomers and polymers. Macromolecules 46, 1305-1311 (2013).
132. F. T. Oakes, J. F. Sebastian, Direct observation of acyl anion equivalents by carbon-13 Fourier transform Nuclear Magnetic Resonance. J. Org. Chem. 45, 4959-4961 (1980).
133. H. Rosenberg, T. T. Tsai, N. K. Ngo, Synthesis of carbonate-containing high-temperature poly(arylene-siloxanylenes). J. Polym. Sci. A Polym. Chem. 20, 1-13 (1982).
134. T. K. Dougherty, Aromatic amine terminated silicone monomers, oligomers, and polymers therefrom. U.S. Pat. No. 5,286,890 (1994).
135. D. S. Kim, S. C. Shim, Synthesis and properties of poly(silylenephenylene-vinylene)s. J. Polym. Sci. A Polym. Chem. 37, 2263-2273 (1999).
136. B. Wang, H. W. Ma, Y. S. Wang, Y. Li, Synthesis and characterization of novel liquid crystalline polystyrene. Chem. Lett. 42, 915-917 (2013).
137. A. Simonneau, M. Oestreich, 3-Silylated cyclohexa-1,4-dienes as precursors for gaseous hydrosilanes: The B(C6F5)3-catalyzed transfer hydrosilylation of alkenes. Angew. Chem. Int. Ed. 52, 11905-11907 (2013).
138. C. M. Kisukuri, D. J. Palmeira, T. S. Rodrigues, P. H. C. Camargo, L. H. Andrade, Bimetallic nanoshells as platforms for metallo- and biometallo-catalytic applications. ChemCatChem 8, 171-179 (2016).
139. S. E. Denmark, R. C. Smith, W.-T. T. Chang, J. M. Muhuhi, Cross-coupling reactions of aromatic and heteroaromatic silanolates with aromatic and heteroaromatic halides. J. Am. Chem. Soc. 131, 3104-3118 (2009).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

| SEQ ID NO: | Sequence | Notes |
| --- | --- | --- |
| 1 | TESGTAAQDPEALAAEIGPVKQVSL GEQIDAALAQQGEQLFNTYCTACHR LDERFIGPALRDVTKRRGPVYIMNV MLNPNGMIQRHPVMKQLVQEYGTMM TDMALSEEQARAILEYLRQVAENQ | Rhodothermus marinus cytochrome c protein (mature) |
| 2 | MLLLSLTLAACGGGSSSSTPQPSGS AAQTESGTAAQDPEALAAEIGPVKQ VSLGEQIDAALAQQGEQLFNTYCTA CHRLDERFIGPALRDVTKRRGPVYI MNVMLNPNGMIQRHPVMKQLVQEYG TMMTDMALSEEQARAILEYLRQVAE NQ | Rhodothermus marinus cytochrome c protein (unprocessed) |
| 3 | MKYLLPTAAAGLLLLAAQPAMA | N-terminal pelB leader sequence |

What is claimed is:

1. A cytochrome c protein variant comprising the amino acid sequence set forth in SEQ ID NO:1 that enantioselectively catalyzes the formation of a carbon-silicon bond and comprises one or more mutations selected from the group consisting of V75, M100, and M103 relative to the amino acid sequence set forth in SEQ ID NO:1.

2. The cytochrome c protein variant of claim 1, wherein the one or more mutations comprise a V75 mutation and an M100 mutation relative to the amino acid sequence set forth in SEQ ID NO:1.

3. The cytochrome c protein variant of claim 1, wherein the one or more mutations comprise an M100 mutation and an M103 mutation relative to the amino acid sequence set forth in SEQ ID NO:1.

4. The cytochrome c protein variant of claim 1, wherein the one or more mutations comprise a V75 mutation, an M100 mutation, and an M103 mutation relative to the amino acid sequence set forth in SEQ ID NO:1.

5. The cytochrome c protein variant of claim 1, wherein the V75 mutation is a V75T mutation.

6. The cytochrome c protein variant of claim 1, wherein the M100 mutation is an M100D or M100E mutation.

7. The cytochrome c protein variant of claim 1, wherein the M103 mutation is an M103E mutation.

8. The cytochrome c protein variant of claim 1, wherein the protein variant comprises a heme cofactor that is a non-native cofactor.

9. The cytochrome c protein variant of claim 1, wherein the protein variant has a higher total turnover number (TTN) compared to a wild-type cytochrome c protein.

10. The cytochrome c protein variant of claim 9, wherein the protein variant has a TTN greater than about 70.

11. The cytochrome c protein variant of claim 10, wherein the protein variant has a TTN greater than about 1,800.

12. The cytochrome c protein variant of claim 1, wherein the protein variant has a higher turnover frequency (TOF) compared to a wild-type cytochrome c protein.

13. The cytochrome c protein variant of claim 12, wherein the TOF is at least about 2-fold greater than the wild-type protein.

14. The cytochrome c protein variant of claim 13, wherein the TOF is at least about 7-fold greater than the wild-type protein.

15. The cytochrome c protein variant of claim 12, wherein the TOF is at least about 10 $min^{-1}$.

16. The cytochrome c protein variant of claim 15, wherein the TOF is at least about 45 $min^{-1}$.

17. The cytochrome c protein variant of claim 1, wherein the protein variant produces an organosilicon product with a % ee of at least about 75%.

18. The cytochrome c protein variant of claim 17, wherein the protein variant produces an organosilicon product with a % ee of at least about 95%.

19. The cytochrome c protein variant of claim 18, wherein the protein variant produces an organosilicon product with a % ee of at least about 99%.

* * * * *

SEQUENCE LISTING

<160> NUMBER OF SEQ ID NOS: 3

<210> SEQ ID NO 1
<211> LENGTH: 124
<212> TYPE: PRT
<213> ORGANISM: Rhodothermus marinus

<400> SEQUENCE: 1

Thr Glu Ser Gly Thr Ala Ala Gln Asp Pro Glu Ala Leu Ala Ala Glu
1               5                   10                  15

Ile Gly Pro Val Lys Gln Val Ser Leu Gly Glu Gln Ile Asp Ala Ala
            20                  25                  30

```
Leu Ala Gln Gln Gly Glu Gln Leu Phe Asn Thr Tyr Cys Thr Ala Cys
        35                  40                  45

His Arg Leu Asp Glu Arg Phe Ile Gly Pro Ala Leu Arg Asp Val Thr
 50                  55                  60

Lys Arg Arg Gly Pro Val Tyr Ile Met Asn Val Met Leu Asn Pro Asn
 65                  70                  75                  80

Gly Met Ile Gln Arg His Pro Val Met Lys Gln Leu Val Gln Glu Tyr
                 85                  90                  95

Gly Thr Met Met Thr Asp Met Ala Leu Ser Glu Glu Gln Ala Arg Ala
                100                 105                 110

Ile Leu Glu Tyr Leu Arg Gln Val Ala Glu Asn Gln
                115                 120

<210> SEQ ID NO 2
<211> LENGTH: 152
<212> TYPE: PRT
<213> ORGANISM: Rhodothermus marinus

<400> SEQUENCE: 2

Met Leu Leu Leu Ser Leu Thr Leu Ala Ala Cys Gly Gly Gly Ser Ser
 1                5                  10                  15

Ser Ser Thr Pro Gln Pro Ser Gly Ser Ala Ala Gln Thr Glu Ser Gly
                 20                  25                  30

Thr Ala Ala Gln Asp Pro Glu Ala Leu Ala Ala Glu Ile Gly Pro Val
                 35                  40                  45

Lys Gln Val Ser Leu Gly Glu Gln Ile Asp Ala Leu Ala Gln Gln
 50                  55                  60

Gly Glu Gln Leu Phe Asn Thr Tyr Cys Thr Ala Cys His Arg Leu Asp
 65                  70                  75                  80

Glu Arg Phe Ile Gly Pro Ala Leu Arg Asp Val Thr Lys Arg Arg Gly
                 85                  90                  95

Pro Val Tyr Ile Met Asn Val Met Leu Asn Pro Asn Gly Met Ile Gln
                100                 105                 110

Arg His Pro Val Met Lys Gln Leu Val Gln Glu Tyr Gly Thr Met Met
                115                 120                 125

Thr Asp Met Ala Leu Ser Glu Glu Gln Ala Arg Ala Ile Leu Glu Tyr
                130                 135                 140

Leu Arg Gln Val Ala Glu Asn Gln
145                 150

<210> SEQ ID NO 3
<211> LENGTH: 22
<212> TYPE: PRT
<213> ORGANISM: Artificial Sequence
<220> FEATURE:
<223> OTHER INFORMATION: Syntehtic N-terminal pelB leader sequence

<400> SEQUENCE: 3

Met Lys Tyr Leu Leu Pro Thr Ala Ala Ala Gly Leu Leu Leu Leu Ala
 1                5                  10                  15

Ala Gln Pro Ala Met Ala
                 20
```